United States Patent [19]

Smale

[11] 4,289,696

[45] Sep. 15, 1981

[54] POLYCYCLIC COMPOUNDS

[75] Inventor: Terence C. Smale, Epsom Downs, England

[73] Assignee: Beecham Group Limited, England

[21] Appl. No.: 120,065

[22] Filed: Feb. 11, 1980

Related U.S. Application Data

[62] Division of Ser. No. 955,598, Oct. 30, 1978, Pat. No. 4,223,038.

[30] Foreign Application Priority Data

Dec. 11, 1977 [GB] United Kingdom ............... 47201/77

[51] Int. Cl.[3] ............................................ C07D 487/04

[52] U.S. Cl. .......................... 260/245.2 T; 260/239 A; 424/244

[58] Field of Search .................................. 260/245.2 T

[56] References Cited

U.S. PATENT DOCUMENTS 4,011,216 3/1977 Menard et al. ............... 260/245.2 T 4,123,547 10/1978 Christensen et al. ........ 260/245.2 T 4,150,145 4/1979 Christensen et al. ........ 260/245.2 T 4,203,902 5/1980 Shih ............................. 260/245.2 T

*Primary Examiner*—Mary C. Lee

*Attorney, Agent, or Firm*—Jacobs & Jacobs

[57] ABSTRACT

The present invention provides a compound of formula (1):

(I)

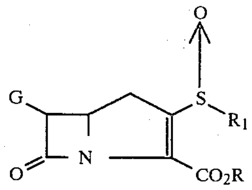

wherein G is hydrogen, alkyl, alkenyl, substituted alkyl or substituted alkenyl, $R_1$ is alkyl or aryl, substituted alkyl or substituted aryl, and R is an organic group such that —$CO_2R$ is an ester group. The compounds are useful as antibacterial and β-lactamase inhibitory agents.

19 Claims, No Drawings

POLYCYCLIC COMPOUNDS

This is a division of Ser. No. 955,598 filed Oct. 30, 1978, now U.S. Pat. No. 4,223,038.

This present invention relates to a novel series of β-lactam derivatives, to a method for their preparation, to their use as anti-bacterial and β-lactamase inhibitory agents.

We have discovered a new series of bicyclic β-lactam derivatives which have anti-bacterial activity, and inhibit β-lactamase enzymes. These enzymes are produced by certain bacteria which are resistant to penicillins and cephalosporins. The compounds are therefore of value in the treatment of bacterial infections in man and animals, particularly domestic animals such as cattle, pigs and poultry, especially where the infection is caused by a β-lactamase producing strain of bacteria. The compounds may be used with a penicillin or cephalosporin to enhance the activity of these latter antibiotics against resistant micro-organisms. The compounds may also be used as disinfectants for example in mineral oils.

Accordingly, the present invention provides a compound of formula (1):

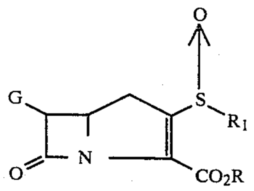

(I)

wherein G is hydrogen, alkyl, alkenyl, substituted alkyl or substituted alkenyl, $R_1$ is alkyl or aryl, substituted alkyl or substituted aryl, and R is an organic group such that $-CO_2R$ is an ester group. Typical alkyl and alkenyl groups which G represents are those which contain up to seven carbon atoms. Typical substituted alkyl groups which G represents are groups of formula (II)-

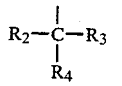

(II)

wherein $R_2$ is hydrogen or hydroxyl and $R_3$ and $R_4$ which may be the same or different represent hydrogen, $C_1$ to $C_6$ alkyl, phenyl, or phenyl substituted by one or more $C_1$ to $C_6$ alkyl groups, $C_1$ to $C_6$ alkoxy groups, nitro groups or halogen atoms, or $R_3$ and $R_4$ together represent an alkylene group containing from 4 to 6 carbon atoms.

Typical alkenyl groups which G represents are prop-2-en-1-yl,3-methylbut-2-en-1-yl, and pent-2-en-1-yl. Particular substituted alkenyl groups which G represents are 4-oxopent-2-en-1-yl and 3-methoxycarbonylprop-2-enyl.

$R_1$ typically represents $C_1$ to $C_6$ alkyl, $C_1$ to $C_6$ alkyl substituted with hydroxy, amino or protected amino group; phenyl or phenyl substituted with one or more halogen atoms, $C_1$ to $C_6$ alkyl groups, $C_1$ to $C_6$ alkoxy groups, amino or protected amino groups. Suitable amino protecting groups include $C_1$ to $C_6$ alkanoyl, benzyloxycarbonyl and p-nitrobenzyloxycarbonyl. Preferred values for $R_1$ are 2-acetamidoethyl, phenyl, p-acetamidophenyl; unbranched alkyl groups such as ethyl, propyl and butyl; and tertiary alkyl groups in which the tertiary centre is α to the sulphur atom e.g. t-butyl and 1,1-dimethyl propyl.

Suitable ester forming groups which R represents are $C_1$ to $C_6$ alkyl; benzyl; substituted benzyl, particularly p-nitrobenzyl and p-methoxybenzyl; phenacyl; substituted phenacyl, such as p-bromophenacyl; and 2,2,2-trichloroethyl; as well as groups such that $-CO_2R$ is readily hydrolysable in vivo particularly in man to yield the free carboxylic acid, for example, the phthalidyl, phthalimidomethyl, α-ethoxycarbonyloxyethyl and $C_1$ to $C_6$ alkanoyloxymethyl such as pivaloyloxymethyl and acetoxymethyl.

One particular subgroup of compounds falling within the general definition of formula (I) are those wherein G is hydrogen i.e. compounds of general formula (III):

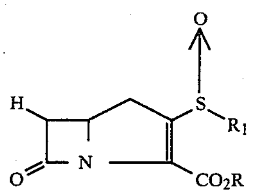

(III)

wherein R and $R_1$ are as previously defined, with reference to formula (I).

Examples of this class of compounds are:

Methyl 7-oxo-3-ethylsulphinyl-1-azabicyclo[3.2.0]hept-2-ene-2-carboxylate,

Benzyl 7-oxo-3-phenyl-sulphinyl-1-azabicyclo[3.2.0-]hept-2-ene-2-carboxylate,

Benzyl 7-oxo-3-ethylsulphinyl-1-azabicyclo[3.2.0]hept-2-ene-2-carboxylate,

Benzyl 3-acetylaminoethylsulphinyl-7-oxo-1-azabicyclo[3.2.0]hept-2-ene-2-carboxylate, Benzyl 3-(4-Acetylaminophenyl)sulphinyl-7-oxo-1-azabicyclo[3.2.0]hept-2-ene-2-carboxylate, Benzyl 3-t-butylsulphinyl-7-oxo-1-azabicyclo[3.2.0-]hept-2-ene-2-carboxylate, Benzyl 3-(2'-hydroxyethyl)sulphinyl-7-oxo-1-azabicyclo[3.2.0]hept-2-ene-2-carboxylate Benzyl 7-oxo-3-tritylsulphinyl-1-azabicyclo[3.2.0]hept-2-ene-2-carboxylate Benzyl 3-nitroethylsulphinyl-7-oxo-1-azabicyclo[3.2.0-]hept-2-ene-2-carboxylate, Benzyl 7-oxo-3-tritylaminoethylsulphinyl-1-azabicyclo[3.2.0]hept-2-ene-2-carboxylate, 4-Nitrobenzyl 3-ethylsulphinyl-7-oxo-1-azabicyclo[3.2.0]hept-2-ene-2-carboxylate, 4-Nitrobenzyl 3-acetylaminoethylsulphinyl-7-oxo-1-azabicyclo-[3.2.0]hept-2-ene-2-carboxylate, 4-Nitrobenzyl 7-oxo-3-tritylaminoethylsulphinyl-1-azabicyclo[3.2.0]hept-2-ene-2-carboxylate and 4-Nitrobenzyl 3-(4-nitrobenzyloxycarbonyl)aminoethylsulphinyl-7-oxo-1-azabicyclo[3.2.0]hept-2-ene-2-carboxylate.

A second subgroup of compounds falling within the general definition of formula (I) are those wherein G is a group of formula (II) above in which $R_2$ is hydroxyl, i.e. compounds of formula (IV):

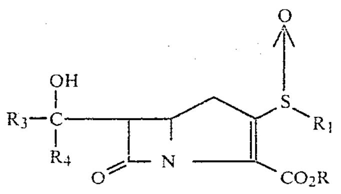

(IV)

wherein R and $R_1$ are as defined above with reference to formula (I) and $R_3$ and $R_4$ are as defined above with reference to formula (II).

Examples of compounds of this type are:

Benzyl 6-(2-hydroxy-2-propyl)-7-oxo-3-ethylsulphinyl-1-azabicyclo[3,2,0]hept-2-ene-2-carboxylate, Benzyl 6-(1-hydroxyethyl)-7-oxo-3-phenylsulphinyl-1-azabicyclo[3,2,0]hept-2-ene-2-carboxylate, and Phthalidyl 6-(1-hydroxyethyl)-7-oxo-3-phenylsulphinyl-1-azabicyclo[3,2,0]hept-2-ene-2-carboxylate.

A further subgroup of compounds falling within the general definition of formula (I) are those wherein G is methoxycarbonylprop-2-ene-1-yl.

Examples of such compounds are:

Benzyl 6-(3-methoxycarbonylprop-2-ene-1-yl)-7-oxo-3-phenylsulphinyl-1-azabicyclo[3,2,0]-hept-2-ene-2-carboxylate, p-Bromophenacyl 3-ethylsulphinyl-6-(3-methoxycarbonylprop-2-ene-1-yl)-7-oxo-1-azabicyclo[3,2,0]hept-2-ene-2-carboxylate, Phthalidyl 3-ethylsulphinyl-6-(3-methoxycarbonylprop-2-ene-1-yl)-7-oxo-1-azabicyclo[3,2,0]hept-2-ene-2-carboxylate, 2,2,2-Trichloroethyl 3-(2',4',5'-trichlorophenyl)sulphinyl-6-(3-methoxycarbonylprop-2-ene-1-yl)-7-oxo-1-azabicyclo[3,2,0]hept-2-ene-2-carboxylate, and p-Bromophenacyl 3-t-butylsulphinyl-6-(3-methoxycarbonylprop-2-ene-1-yl)-7-oxo-1-azabicyclo[3,2,0]hept-2-ene-2-carboxylate.

Compounds of formula (I) possess two principal chiral centres viz the carbon atom marked 5 below and the sulphur atom. When G is other than hydrogen the compounds have a third chiral centre, carbon 6.

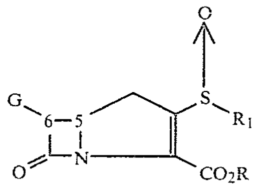

Thus, when we refer generally to compounds of formula (I) herein, we mean mixtures of stereochemical isomers as well as pure isomers. Compounds in which the C-5 carbon atom has the stereochemistry shown in (V) below are preferred.

Unless otherwise specified, reference to compounds (V) means enantiomeric mixtures. Within this group, the hydrogen atom attached to the C-6 carbon atom may be cis or trans to the hydrogen atom attached to the C-5 carbon atom. The cis and trans series both have advantageous levels of anti-bacterial and $\beta$-lactamase inhibitory activity but the activity of the cis compounds is marginally superior. The cis compounds have the stereochemistry of formula (V).

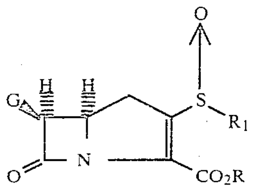

(V)

Compounds of general formula (I) are isomeric at the sulphur atom as shown in formulae (1a) and (1b) below:

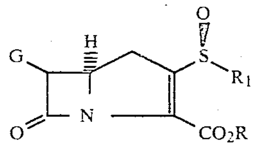

(1a)

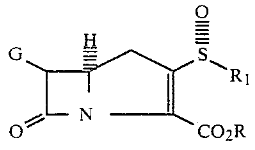

(1b)

where the wedge shaped bond and the hatched bond have their usual stereochemical significance. Compounds (1b) have marginally superior biological activity.

When using the compounds of this invention as medicinal agents they may be presented in a number of different dosage forms in accordance with standard pharmaceutical and veterinary practice.

Accordingly, the invention provides a pharmaceutical or veterinary composition comprising a compound of formula (I) as defined above together with a pharmaceutically or veterinary acceptable carrier.

Compounds of formula (I) which are active when given orally may be compounded in the form of syrups, tablets, capsules and lozenges. A syrup formulation will generally consist of a suspension or solution of the compound in a suitable liquid carrier such as ethyl alcohol, glycerine or water with a flavouring or colouring agent. Where the composition is in the form of a capsule the solid in granular form is encased in a gelatin shell. Where the composition is in the form of a tablet, any suitable pharmaceutical carrier routinely used for preparing solid formulations may be used. Examples of such carriers include magnesium stearate, starch, lactose, glucose, sucrose, rice flour and chalk. The compounds of this invention may be present in compositions for injection in a sterile aqueous carrier or parenterally acceptable oil. Alternatively, the compounds may be administered topically as a cream, or lotion, or as a pessary or suppository.

The effective dose of compound (I) depends upon the particular compound employed but in general is in the range of from 2.0 to 5.0 mg/kg/day, the exact dose depending upon the age, weight and condition of the patient and on the frequency and route of administration.

Where appropriate, other anti-bacterial agents such as penicillins or cephalosporins may be included. Particularly suitable penicillins include amoxycillin, ampicillin, talampicillin, pivampicillin and bacampicillin. As is common practice, the compositions will usually be accompanied by written or printed directions for use in the medical treatment concerned.

Compounds of formula (I) above are prepared by dehydrohalogenating a compound of formula (VI) below.

Accordingly, the invention further provides a method for preparing a compound of formula (I) which method comprises dehydrohalogenating a compound of formula (VI):

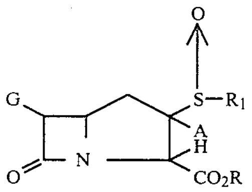
(VI)

wherein G, R and $R_1$ are as defined with reference to formula (I) and A represents chlorine, bromine or iodine; with a base of low nucleophilicity. By a base of low nucleophilicity is meant one which does not decompose the $\beta$-lactam ring of the intermediate (VI).

Examples of such bases include tertiary cyclic and acyclic amines, such as N-methylmorpholine and triethylamine; tertiary bicyclic diazalkanes and alkenes such as 1,5-diazabicyclo[4,3,0]non-5-ene, 1,5-diazabicyclo[5,4,0]undec-5-ene, and 1,4-diazabicyclo[2,2,2]octane; and alkali metal bases of low nucleophilicity such as sodium thiophenoxide. We have found that best results are obtained when one equivalent of base is used.

This reaction is suitably carried out in an organic solvent. The choice of solvent is not critical to the success of the reaction. We prefer alkyl alkanoate esters such as ethyl acetate, but other solvents such as ethers, NN-dimethylformamide and dimethylsulphoxide are equally acceptable. For convenience, we have used ethyl acetate.

We have found that the method produces acceptable yields of product when carried out at moderate, (i.e. −20° to 40° C.) temperatures; room temperature is chosen for convenience.

Although it is not essential for the success of the reaction, we have found that improved yields are obtained when the reaction is carried out under an inert atmosphere such as argon or nitrogen.

The invention further provides a compound of formula (VI) above wherein G, R and $R_1$ are as defined with reference to formula (I) and A represents chlorine, bromine or iodine.

Particular values for R, $R_1$ and G are as discussed above with reference to compounds of formula (I). A particularly suitable value for A is chlorine. Examples of compounds of formula (VI) include:

Methyl 3-chloro-7-oxo-3-ethylsulphinyl-1-azabicyclo[3,2,0]heptane-2-carboxylate.

Benzyl 3-chloro-7-oxo-3-phenylsulphinyl-1-azabicyclo[3,2,0]heptane-2-carboxylate, Benzyl 3-chloro-7-oxo-3-ethylsulphinyl-1-azabicyclo[3.2.0]heptane-2-carboxylate, Benzyl 3-acetylaminoethylsulphinyl-3-chloro-7-oxo-1-azabicyclo[3.2.0]heptane-2-carboxylate, Benzyl 3-(4'-acetamidophenyl)sulphinyl-3-chloro-7-oxo-1-azabicyclo-[3.2.0]heptane-2-carboxylate, Benzyl 3-t-butylsulphinyl-3-chloro-7-oxo-1-azabicyclo[3.2.0]heptane-2-carboxylate, Benzyl 3-chloro-3-nitroethylsulphinyl-7-oxo-1-azabicyclo[3.2.0]heptane-2-carboxylate, Benzyl 3-chloro-3-(2'-hydroxyethyl)sulphinyl-7-oxo-1-azabicyclo[3.2.0]heptane-2-carboxylate, Benzyl 3-chloro-7-oxo-3-tritylsulphinyl-1-azabicyclo[3.2.0]heptane-2-carboxylate, Benzyl 3-chloro-7-oxo-3-tritylaminoethylsulphinyl-1-azabicyclo[3.2.0]heptane-2-carboxylate, 4-Nitrobenzyl 3-chloro-3-ethylsulphinyl-7-oxo-1-azabicyclo[3.2.0]heptane-2-carboxylate, 4-Nitrobenzyl 3acetylaminoethylsulphinyl-3-chloro-7-oxo-1-azabicyclo[3.2.0]heptane-2-carboxylate, 4-Nitrobenzyl 3-chloro-7-oxo-3-tritylaminoethylsulphinyl-1-azabicyclo[3.2.0]heptane-2-carboxylate, 4-Nitrobenzyl 3-chloro-3-(4'-nitrobenzyloxycarbonylaminoethylsulphinyl)-7-oxo-1-azabicyclo[3.2.0-]heptane-2-carboxylate, Benzyl 3-chloro-6-(2-hydroxy-2-propyl)-3-ethylsulphinyl-7-oxo-1-azabicyclo[3.2.0]heptane-2-carboxylate, Benzyl 3-chloro-6-(1-hydroxyethyl)-7-oxo-3-phenylsulphinyl-1-azabicyclo[3.2.0]heptane-2-carboxylate, Phthalidyl 3-chloro-6-(1-hydroxyethyl)-7-oxo-3-phenylsulphinyl-1-azabicyclo[3.2.0]heptane-2-carboxylate, Benzyl 3-chloro-6-(3-methoxycarbonylprop-2-ene-1-yl)-7-oxo-3-phenylsulphinyl-1-azabicyclo[3.2.0]heptane-2-carboxylate, p-Bromophenacyl 3-chloro-3-ethylsulphinyl-6-(3-methoxycarbonylprop-2-ene-1-yl)-7-oxo-1-azabicyclo[3.2.0]heptane-2-carboxylate, Phthalidyl 3-chloro-3-ethylsulphinyl-6-(3-methoxycarbonylprop-2-ene-1-yl)-7-oxo-1-azabicyclo[3.2.0]heptane-2-carboxylate, 2,2,2-Trichloroethyl 3-chloro-3-(2',4',5'-trichlorophenylsulphinyl)-6-(3-methoxycarbonylprop-2-ene-1-yl)-7-oxo-1-azabicyclo[3.2.0]heptane-2-carboxylate, and p-Bromophenacyl 3-butylsulphinyl-3-chloro-6-(3-methoxycarbonylprop-2-ene-1-yl)-7-oxo-1-azabicyclo[3.2.0]heptane-2-carboxylate.

The compounds of formula (VI) are prepared by oxidative halogenation of a suitable 7-oxo-3-thio-1-azabicyclo[3,2,0]heptane carboxylate (VII) below. This oxidative halogenation is essentially a two-step reaction, but the whole preparation can be carried out as a concerted process without the need to isolate any intermediates.

Accordingly, in a further aspect, the invention provides a method for preparing a compound of formula (VI) above which process comprises reacting a compound of formula (VII):

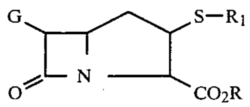
(VII)

wherein G, R and $R_1$ are as defined in formula (I), with an oxidizing agent known to convert sulphides to sulphoxides and thereafter reacting the sulphoxide so produced with a source of electrophilic halogen.

The preferred values of G, R and $R_1$ are discussed with reference to formula (I). Suitable halogens are discussed with reference to A above.

Examples of compounds of formula (VII) are:

Methyl 7-oxo-3-ethylthio-1-azabicyclo[3.2.0]heptane-2-carboxylate,

Benzyl 7-oxo-3-phenylthio-1-azabicyclo[3,2,0]heptane-2-carboxylate,

Benzyl 7-oxo-3-ethylthio-1-azabicyclo[3.2.0]heptane-2-carboxylate,

Benzyl 3-acetylaminoethylthio-7-oxo-1-azabicyclo[3.2.0]heptane-2-carboxylate,

Benzyl 3-(4'-acetamidophenyl)thio-7-oxo-1-azabicyclo[3,2,0]heptane-2-carboxylate, Benzyl 3-t-butylthio-7-oxo-1-azabicyclo[3.2.0]heptane-2-carboxylate, Benzyl 3-nitroethylthio-7-oxo-1-azabicyclo[3.2.0]heptane-2-carboxylate, Benzyl 3-(2'-hydroxyethyl)thio-7-oxo-1-azabicyclo[3.2.0]heptane-3-carboxylate, Benzyl 7-oxo-3-tritylthio-1-azabicyclo[3.2.0]heptane-2-carboxylate, Benzyl 7-oxo-3-tritylaminoethylamino-1-azabicyclo[3.2.0]heptane-2-carboxylate, 4-Nitrobenzyl 3-ethylthio-7-oxo-1-azabicyclo[3.2.0-]heptane-2-carboxylate, 4-Nitrobenzyl 3-acetylaminoethylthio-7-oxo-1-azabicyclo[3.2.0]heptane-2-carboxylate, 4-Nitrobenzyl 7-oxo-3-tritylaminoethylthio-1-azabicyclo[3.2.0]heptane-2-carboxylate, 4-Nitrobenzyl 3-(4'-nitrobenzyloxycarbonylaminoethylthio)-7-oxo-1-azabicyclo[3.2.0]heptane-2-carboxylate, Benzyl 6-(2-hydroxy-2-propyl)-3-ethylthio-7-oxo-1-azabicyclo[3.2.0]heptane-2-carboxylate, Benzyl 6-(1-hydroxyethyl)-7-oxo-3-phenylthio-1-azabicyclo[3.2.0]heptane-2-carboxylate, Phthalidyl 6-(1-hydroxyethyl)-7-oxo-3-phenylthio-1-azabicyclo[3.2.0]heptane-2-carboxylate, Benzyl 6-(3-methoxycarbonylprop-2-ene-1-yl)-7-oxo-3-phenylthio-1-azabicyclo[3.2.0]heptane-2-carboxylate, p-Bromophenacyl 3-ethylthio-6-(3-methoxycarbonyl-prop-2-ene-1-yl)-7-oxo-1-azabicyclo[3.2.0]heptane-2-carboxylate, Phthalidyl 3-ethylthio-6-(3-methoxycarbonylprop-2-ene-1-yl)-7-oxo-1-azabicyclo[3.2.0]heptane-2-carboxylate, 2,2,2-Trichloroethyl 3-(2',4',5',-trichlorophenyl)thio-6-(3-methoxycarbonylprop2-ene-1-yl)-7-oxo-1-azabicyclo[3.2.0]heptane-2-carboxylate, and p-Bromophenacyl 3-butylthio-6-(3-methoxycarbonyl-prop-2-ene-1-yl)-7-oxo-1-azabicyclo[3.2.0]heptane-2-carboxylate.

Standard reagents which are known to oxidize sulphides to sulphoxides include per-acids, in particular perbenzoic acid and m-chloroperbenzoic acid. Sources of electrophilic halogens include N-haloamides and N-haloimides, e.g. N-halosuccinimides; sulphuryl halides and elemental halogens.

We have found that both oxidation and halogenation can be conveniently carried out using approximately 2 molar proportions of iodobenzene dichloride and at least 1 molar proportion of water in an organic solvent in the presence of 3 molar proportions of an organic base. Organic bases which are suitable for use in the iodobenzene dichloride process include tertiary aliphatic amines such as triethylamine and aromatic bases such as pyridine.

The reaction is carried out in a organic solvent the choice of which is not critical to the success of these reactions. We have found that aprotic solvents such as halogenated hydrocarbons are most convenient.

The reactions are best carried out at moderate to low temperatures, i.e. not greater than 30° C. and not less than $\dot{-}20°$ C., 0° C. being convenient. Although it is not essential, the reaction may be usefully carried out under an inert atmosphere such as nitrogen or argon.

Intermediates of formula (VII) above may be prepared by reacting a suitable 7-oxo-1-azabicyclo [3.2.0]hept-2-ene-2-carboxylate derivative (VIII) below, with a thiol.

Accordingly, the invention provides a method for preparing a compound of formula (VII) which comprises the reaction of a compound of formula (VIII):

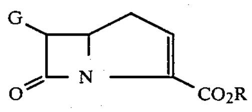

(VIII)

wherein G and R are as defined in formula (I) with a thiol of formula $R_1SH$, wherein $R_1$ is as defined in formula (I), in the presence of an inorganic base.

Particular values for G, R and $R_1$ are as discussed with reference to formula (I) above. Examples of compounds of formula (VIII) include:

Methyl 7-oxo-1-azabicyclo[3.2.0]hept-2-ene-2-carboxylate,

Benzyl 7-oxo-1-azabicyclo[3.2.0]hept-2-ene-2-carboxylate,

4-Nitrobenzyl 7-oxo-1-azabicyclo[3.2.0]hept-2-ene-2-carboxylate,

Benzyl 6-(2-hydroxy-2-propyl)-7-oxo-1-azabicyclo[3.2.0]hept-2-ene-2-carboxylate, Benzyl 6-(1-hydroxyethyl)-7-oxo-1-azabicyclo[3.2.0-]hept-2-ene-2-carboxylate, Phthalidyl 6-(1-hydroxyethyl)-7-oxo-1-azabicyclo[3.2.0]hept-2-ene-2-carboxylate, Benzyl 6-(3-methoxycarbonylprop-2-ene-1-yl)-7-oxo-1-azabicyclo[3.2.0]hept-2-ene-2-carboxylate, p-Bromophenacyl 6-(3-methoxycarbonylprop-2-ene-1-yl)-7-oxo-1-azabicyclo[3,2,0]hept-2-ene-2-carboxylate, Phthalidyl 6-(3-methoxycarbonylprop-2-ene-1-yl)-7-oxo-1-azabicyclo[3.2.0]hept-2-ene-2-carboxylate, 2,2,2-Trichloroethyl 6-(3-methoxycarbonylprop-2-ene-1-yl)-7-oxo-1-azabicyclo[3.2.0]hept-2-ene-2-carboxylate, and Suitably the inorganic base is a carbonate, in particular an alkaline earth metal carbonate or an alkali metal carbonate such as potassium carbonate.

The reaction is conveniently carried out in a polar organic solvent such as dimethylformamide at moderate temperatures i.e. not in excess of 40° C., room temperature (ca. 20° C.) being most appropriate.

The preparation of compounds (I) stereochemically pure about the sulphur atom may be understood with reference to the following scheme:

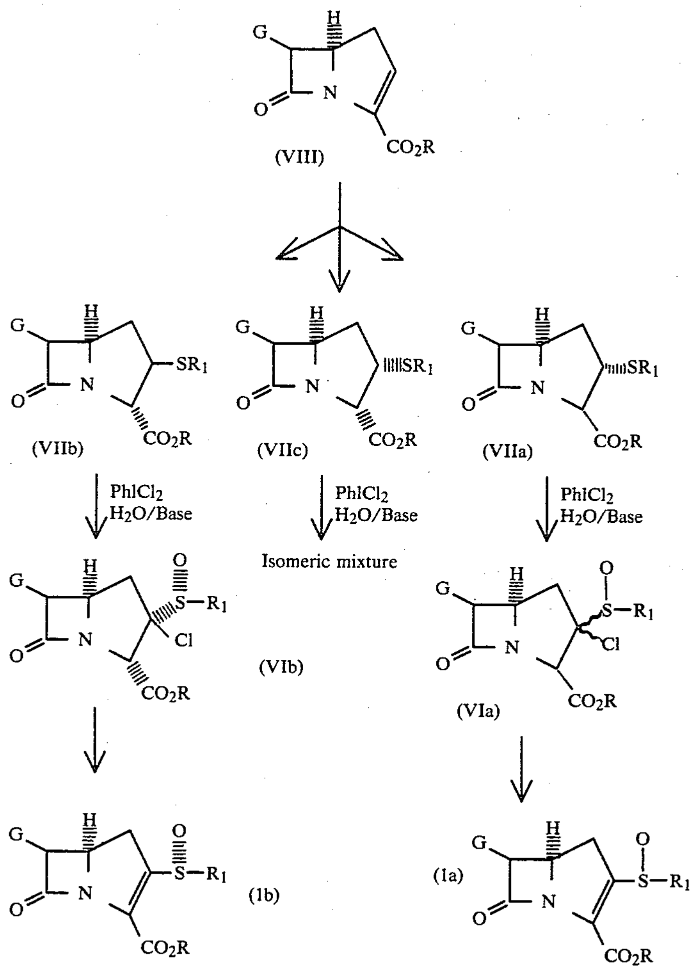

(VIII)

(VIIb) (VIIc) (VIIa)

(VIb) (VIa)

(Ib) (Ia)

When the thiol R'SH reacts with compounds (VIII) an isomeric mixture of (VIIa), (VIIb) and (VIIc) results in which (VIIa) and (VIIb) usually predominate.

These isomers are separable by physical techniques such as chromatography and crystallisation. Isomers (VIIa) and (VIIb) are transformed stereospecifically to (Ia) and (Ib) respectively in the subsequent reaction steps. Isomer (VIIc) produces isomeric mixtures. It is also found that where isomers (VIIb) are contaminated with minor amounts of isomers (VIIc) the impurity is lost during the subsequent process steps, giving pure (Ib).

Since the steps involve no inversion about the C-5 carbon atom optically pure (Ia) and (Ib) may be obtained by beginning with optically pure (VIII), prepared as described below.

Compounds of the formula (VIII) may be prepared by a process which comprises the ring closing elimination of the elements of $O=PA_1A_2A_3$ from a compound of the formula (IX):

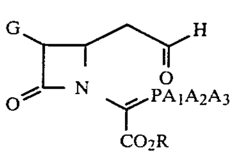

(IX)

wherein R and G are as defined in relation to formula (I) and $A_1$, $A_2$ and $A_3$ are $C_1$ to $C_6$ alkyl or phenyl groups.

Most suitably, $A_1$, $A_2$ and $A_3$ are each phenyl groups.

The elimination reaction tends to occur spontaneously at relatively low temperatures, for example −20° C. to 0° C.

The solvent used for the preceding process will be an inert organic solvent such as ethyl acetate, benzene or toluene.

The compounds of the formula (IX) may be prepared by a sequence such as:

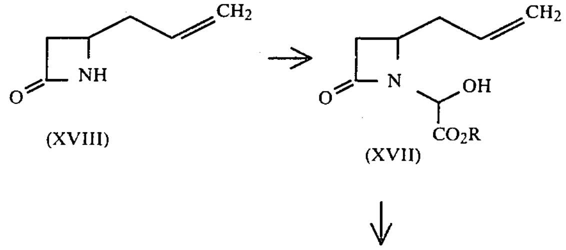

(XVIII) (XVII)

-continued

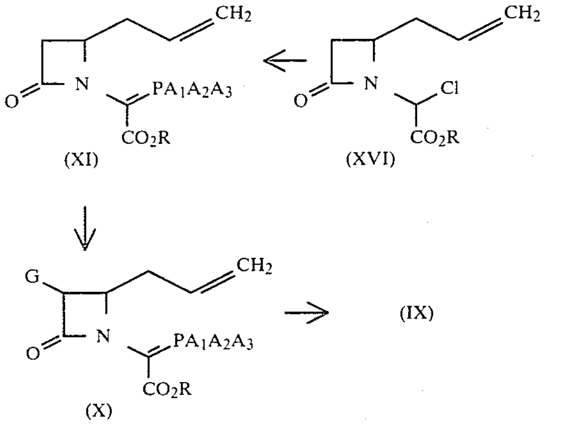

(XI) (XVI) (X) (IX)

Compounds of the formula (IX) are prepared in turn by a process which comprises the ozonolysis in the presence of excess trifluoroacetic acid of a compound of the formula (X):

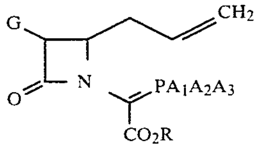

(X)

wherein R, G, $A_1$, $A_2$ and $A_3$ are as defined in relation to formula (IX) and thereafter neutralising the trifluoroacetic acid.

This ozonolysis is normally carried out in an inert solvent such as ethyl acetate.

The process is normally carried out at a depressed temperature, for example −80° to −20° C., more usually at about −70° to −50° C. In general ozone is passed through the solution until a light blue colour is produced. At this point excess ozone may be removed by passing through an inert gas. The intermediate ozonide may be reduced by the addition of a conventional reducing agent such as triphenylphosphine. The trifluoroacetic acid should be neutralised for example by the addition of a solution of a base such as sodium bicarbonate solution at about 0° C.

Once the neutralization is complete the reaction is usually allowed to warm to ambient temperature under which conditions the compound spontaneously cyclises.

Compounds of the formula (X) are prepared by a process which comprises reacting compound of formula (XI):

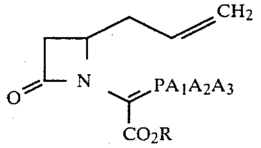

(XI)

wherein $A_1$, $A_2$, $A_3$ and R are as defined in relation to formula (IX) with a base to generate an anion of the formula (XII):

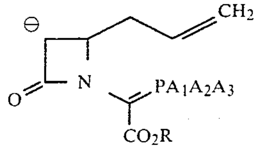

(XII)

wherein $A_1$, $A_2$, $A_3$ and R are as defined in relation to formula (IX) which is then reacted with a compound of the formula (XIII) or (XIV):

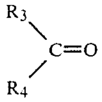

(XIII)

$G_1$—Y (XIV)

wherein $R_3$ and $R_4$ are as defined in relation to formula (II), $G_1$ is an alkyl, substituted alkyl, alkenyl or substituted alkenyl group and Y is a moiety readily displaced by a nucleophile.

Suitable values for Y include Cl, Br, I, $OSO_2CH_3$ $O.SO_2.C_6H_4CH_3$ or the like. Particularly suitable values for Y include Cl, Br and I.

The generation and reaction of the anion of the formula (XII) is brought about in an inert organic medium under aprotic conditions. Suitable solvents for the reaction include hydrocarbons such as hexane, tetrahydrofuran, dimethoxyethane, formdimethylamide, hexamethylphosphorustriamide or mixtures thereof.

Since the anion is a highly reactive species its generation and reaction are normally effected at a depressed temperature, for example below 0° C., more suitably −80° to −60° C.

The base used to generate the anion of the formula (XII) will be a strong base of low nucleophilicity. Suitable bases include lithium alkyls such as lithium butyl, lithium amides such as lithium diisopropylamide or lithium hexamethydisilylamide.

Once formed the anion may be quenched by the addition of the dry compound of the formula (XIII) or (XIV). The compound of the formula (XIII) or (XIV) may be added neat or dissolved in a dry inert solvent.

It is most suitable to carry out the preceding reactions under an inert atmosphere, for example under dry nitrogen or dry argon.

The preceding reaction normally produces a mixture of the cis- and trans- compounds of the formulae (XVa) and (XVb):

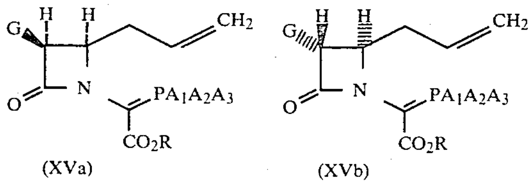

(XVa) (XVb)

in admixture with their enantiomers.

These cis- and trans-substituted compounds can generally be separated from each other by chromatography, for example over silica gel gradiently eluting with a solvent mixture such as ethyl acetate/hexane.

When the compound of the formula (XVa) is used in subsequent reactions, the cis isomer of compounds (I) is obtained.

The compounds of the formula (XI) may be prepared by the reaction of a compound of the formula (XVI):

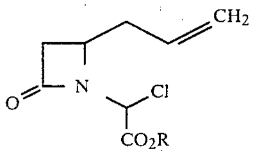

(XVI)

wherein R is as defined in relation to formula (I) with a phosphine of the formula $PA_1A_2A_3$ wherein $A_1$, $A_2$ and $A_3$ are as defined in relation to formula (IX).

This reaction is normally carried out in an inert solvent such as dioxane, tetrahydrofuran or the like in the presence of at least 1 equivalent of a base such as 2,6-lutidine or like base of relatively low nucleophilicity.

In general the reaction is carried out at a nonextreme temperature such as about 5°-35° C.

The compound of formula (XVI) may be prepared by the reaction of thionyl chloride on a corresponding compound of the formula (XVII):

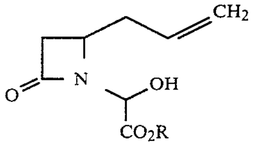

(XVII)

wherein R is as defined in relation to formula (I).

This reaction takes place under similar conditions to the preparation of the compound for the formula (XVI) except that a depressed temperature, for example −30° to −10° C., is used.

The compound of the formula (XVII) may be prepared by the reaction of a compound of the formula (XVIII):

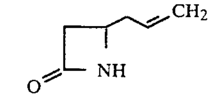

(XVIII)

and a compound of the formula (XIX):

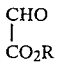

(XIX)

wherein R is as defined in relation to formula (I).

This preceding reaction is conveniently carried out by reacting the compound together in refluxing benzene in such a manner that any water present is continuously removed.

The azetidinone (XVIII) may be resolved by analogy with known methods [see for example British Patent Specification No. 1,273,278], and starting with optically pure azetidinone (XVIII) optically pure (VIII) may be obtained by the methods set out above.

The compounds of the formula (I) wherein G is an alkenyl or substituted alkenyl group, may also be prepared by the following reaction sequence in which $R_6$ and $R_7$ are the same or different and represent hydrogen atoms, alkyl groups or substituted alkyl groups. In particular $R_6$ represents hydrogen, and $R_7$ methyl, ethyl, acetyl propionyl and methoxycarbonyl; or $R_6$ and $R_7$ both may represent methyl.

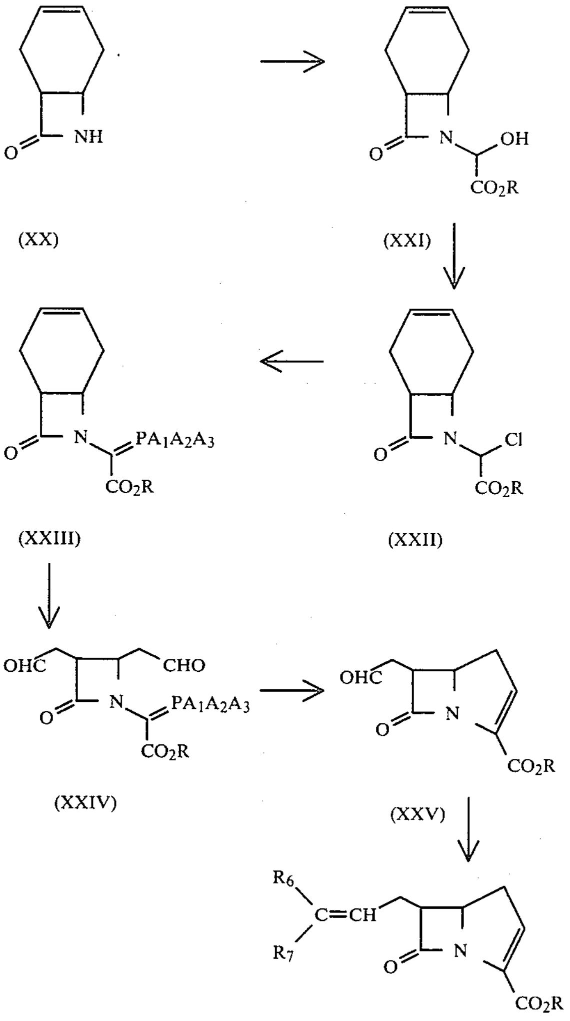

(XX) (XXI) (XXII) (XXIII) (XXIV) (XXV) (XXVI)

The compounds of the formula (XX) may be obtained by the method of Paquette et al, J. Amer. Chem. Soc., 90, 2897 (1968). Optically pure (XX) may be prepared by resolving a racemic mixture by analogy with known methods for resolving azetidinones. [see for example British Patent Specification No. 1,273,278].

The compounds of the formula (XX) prepared in this manner have the cis-configuration at the ring junction and this configuration is preserved in the compounds of the formulae (XXI)-(XXVI). Similarly if the starting material (XX) is optically pure, optically pure (XXVI) is obtained.

The compounds of the formula (XXI) may be prepared by the reaction of a compound of the formula (XX) with a compound of the formula (XIX) as hereinbefore defined under conditions similar to those described for the reaction of a compound of the formulae (XVIII) and (XIX).

Reaction of a compound of the formula (XXI) with thionyl chloride under conditions similar to those described for the reaction of thionyl chloride with a compound of the formula (XVII) may be used to prepare the compounds of the formula (XXII).

The compounds of the formula (XXII) may be converted into the compounds of the formula (XXIII) by reaction with a phosphine of the formula $PA_1A_2A_3$ under conditions similar to those used for the preparation of a compound of the formula (XI):

Compounds of the formula (XXIV):

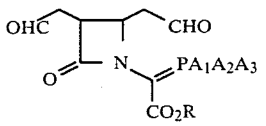

(XXIV)

wherein R, $A_1$, $A_2$ and $A_3$ are as defined in relation to formula (IX) are prepared by a process which comprises the ozonolysis of a compound of the formula (XXIII):

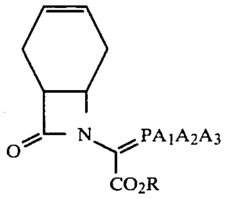

(XXIII)

wherein R, $A_1$, $A_2$ and $A_3$ are as defined in relation to formula (IX).

The ozonolysis reaction may be brought about under conditions similar to those described for the ozonolysis of the compounds of the formula (X).

Once formed the compounds of the formula (XXIV) undergo spontaneous cyclisation with elimination of the elements of a compound of the formula $O{=}PA_1A_2A_3$ and the formation of a compound of the formula (XXV).

The compounds of the formula (XXV) tend to be somewhat unstable so that it is often more suitable to react them in situ with an agent such as a compound of the formula (XXVII):

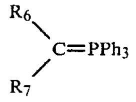

(XXVII)

or chemically equivalent agents wherein $R_6$ and $R_7$ are the same or different and represent hydrogen atoms, alkyl groups or substituted alkyl groups.

This reaction of the compounds of the formulae (XXV) and (XXVII) occurs under conventional reaction conditions for reaction of an aldehyde and a phosphorane and gives the olefins of formula (XXVI).

In the Examples below, the reaction of one $C_5$ enantiomer only is depicted but each reaction is carried out with racemic starting materials.

EXAMPLE 1

Benzyl 7-oxo-3-phenylsulphinyl-1-azabicyclo[3.2.0]hept-2-ene-2-carboxylate

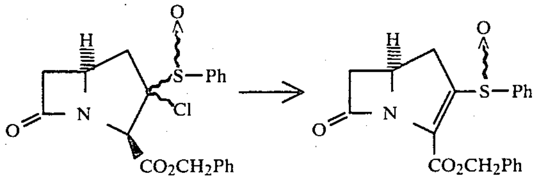

(1) (2)

A suspension of the α-chlorosulphoxide (1) (0.058 g.) in ethyl acetate (5 ml) was stirred under argon at room temperature and treated with 1,5-diazabicyclo[5,4,0]undec-5-ene (0.022 g). After 1 hour, the product was washed with brine and dried over sodium sulphate. The ethyl acetate solution was concentrated to small bulk (ca 0.5 ml) and set aside in the refrigerator to complete crystallisation. The solid was then filtered off and dried; yield 0.030 g. of a single sulphoxide isomer (2); m.p. 129°-131°; νmax($CHCl_3$) 3000, 1795, 1730 and 1040 $cm^{-1}$; λmax (EtOH) 297 nm (ε6,650): τ($CDCl_3$) 2.3-2.8 (10H, m, phenyls), 4.67 (2H, s, benzyl $CH_2$), 5.6-5.9 (1H, m, C5-H), 6.53 (1H, dd, J18 and 10 Hz, C4-H), 6.61 (1H, dd, J≠and 5 Hz, C6-H), 7.20 (1H, dd, J16 and 3 Hz, C6-H) and 7.55 (1H, dd, J18 and 8 Hz, C4-H); ($M^+$ at m/e 367.0847. $C_{20}H_{17}NO_4S$ requires 367.0878); (Found; C, 65.2; H, 4.8; N, 3.9%. $C_{20}H_{17}NO_4S$ requires C, 65.4; H, 4.7 and N, 3.8%).

EXAMPLE 2

Benzyl 7-oxo-3-phenylsulphinyl-1-azabicyclo[3,2,0]hept-2-ene-2-carboxylate

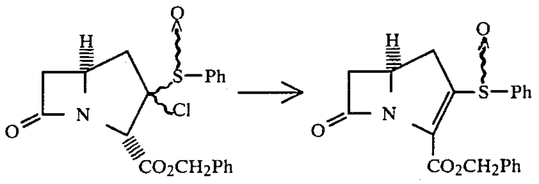

(3) (4)

A solution of the chlorosulphoxide (3) (0.020 g) in ethyl acetate (2 ml) was stirred under argon at room temperature and treated with 1,5-diazabicyclo[5,4,0]undec-5-ene (0.008 g) in one portion. After a period of 10 minutes, the reaction mixture was washed with brine and dried over sodium sulphate. The ethyl acetate solution was evaporated to a gum (0.018 g) which was substantially pure title compound (4), isomeric at sulphur to compound (2). The data for (4) were $\nu_{max}$($CHCl_3$) 3000, 2940, 1795, 1725 and 1040 $cm^{-1}$; τ($CDCl_3$) 2.3-2.8 (10H, m, phenyls), 4.67 (2H, s, benzyl $CH_2$), 5.8-6.1 (1H, m, C5-H), 6.55 (1H dd, J16 and 5 Hz, C6-H), 6.79 (1H, dd, J18 and 8 Hz, C4-H), 6.96 (1H, dd, J16 and 3 Hz, C6-H) and 7.26 (1H, dd, J18 and 10 Hz, C4-H): $\lambda_{max}$(EtOH) 298 nm (ε approx 8,000).

EXAMPLE 3

Benzyl 3-chloro-7-oxo-3-phenylsulphinyl-1-azabicyclo[3,2,0-]heptane-2-carboxylate

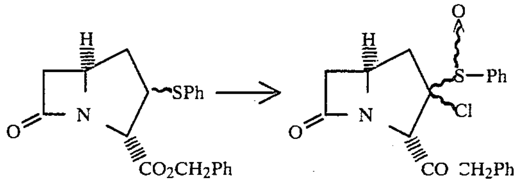

(5) and (6) (7)

A mixture of $C_3$ diastereoisomers of benzyl 7-oxo-3-phenylthio-1-azabicyclo[3,2,0]heptane-2α-carboxylate (5) and (6) (0.056 g) was dissolved in chloroform (3 ml). This solution was stirred under argon in an ice-bath and treated successively with water (0.003 g), pyridine (0.038 g) and iodobenzene dichloride (0.087 g). The ice-bath was removed after 15 minutes and 2 hours later the product was concentrated. This was chromatographed on silica gel 60 (<230 mesh), eluting with 60°-80° petroleum ether/ethyl acetate 1:1 to give one main fraction (0.036 g). Crystallization of this from ethyl acetate/60°-80° petroleum ether gave a single pure chlorosulphoxide isomer (7); m.p. 135°-140°; $\nu_{max}$ ($CHCl_3$) 3000, 1785 and 1745 $cm^{-1}$; τ($CDCl_3$) 2.3-2.8 (10H, m, phenyls), 4.76 (2H, s, benzyl $CH_2$), 4.94 (1H, s, C2-H), 5.7-5.9 (1H, m, C5-H), 6.64 (1H, dd, J16 and 5 Hz, C6-H), 6.95 (1H, dd, J16 and 3 Hz, C6-H), 7.10 (1H, dd, J15 and 8 Hz, C4-H), and 8.20 (1H, dd, J15 and 2 Hz, C4-H); (Found: C, 59.4; H, 4.4; N, 3.3%. $C_{20}H_{18}ClNO_4S$ requires, C, 59.5; H, 4.5 and N, 3.5%).

EXAMPLE 4

Benzyl 3-chloro-7-oxo-3-phenylsulphinyl-1-azabicyclo[3,2,0-]heptane-2-carboxylate

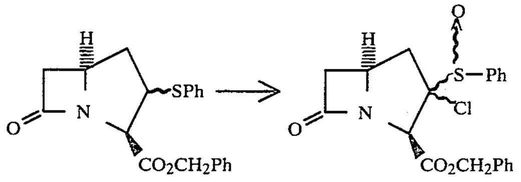

(8) (1)

Benzyl 7-oxo-3-phenylthio-1-azabicyclo[3,2,0]heptane-2β-carboxylate (8) (0.295 g) was stirred under argon in chloroform (15 ml) containing water (0.015 g) and pyridine (0.198 g). This solution was cooled in an ice bath and treated with iodobenzene dichloride (0.460 g) in one portion. After 15 minutes the ice bath was removed and after a further 2 hours the reaction mixture was concentrated. Only one major isomer of the chlorosulphoxide (1) was formed, and this was isolated by chromatography on silica gel 60 (<230 mesh) eluting with 60°-80° petroleum ether/ethyl acetate 1:1. The product was a colourless solid (0.135 g) which could be recrystallized from chloroform/60°-80° petroleum ether; m.p. 155°-165°; $\nu_{max}$($CHCl_3$) 2980, 1775 and 1735 $cm^{-1}$; τ($CDCl_3$) 2.3-2.8 (10H, m, phenyls), 4.71 (2H, s, benzyl $CH_2$), 5.58 (1H, s, C2-H), 5.8-6.1 (1H, m, C5-H), 6.81 (1H, dd, J16 and 5 Hz, C6-H), 7.13 (1H, dd, J16 and 2½ Hz, C6-H), 7.50 (1H, dd, J12 and 9 Hz, C4-H) and 8.30 (1H, dd, J12 and 5 Hz, C4-H); (Found: C, 59.1; H, 4.5; N, 3.4%. $C_{20}H_{18}ClNO_4S$ requires; C, 59.5; H, 4.5 and N, 3.5%).

EXAMPLE 5

Methyl 3-ethylthio-7-oxo-1-azabicyclo[3,2,0]heptane-2-carboxylate

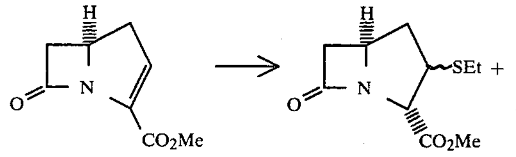

(9) (10) and (11)

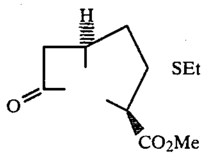

(12)

A stirred solution of methyl 7-oxo-1-azabicyclo[3,2,0-]hept-2-ene-2-carboxylate (9) (0.050 g) in dry dimethylformamide (1 ml) at room temperature was treated with ethane thiol (0.10 ml) followed by powdered potassium carbonate (0.023 g). After a period of 1 hour, the excess thiol was blown off in a stream of argon and the residue concentrated at 30° under reduced pressure. The residual gum was dissolved in ethyl acetate, washed with brine and dried over sodium sulphate. The ethyl acetate solution was concentrated and the three diastereoisomers (10, 11 and 12 in order of increasing polarity) were separated by column chromatography on silica gel 60 (<230 mesh), eluting with 60°-80° petroleum ether/ethyl acetate 7:3.

Isomer A

(10) (0.026 g) was a gum: $\nu_{max}$($CHCl_3$) 2980, 1770 and 1750 (sh)$cm^{-1}$; τ ($CDCl_3$) 5.30 (1H, d, J 7 Hz, C2-H). 5.91 (1H, tdd, J6,5 and 2½ Hz, C5-H), 6.30 (3H, s, $OCH_3$), 6.44 (1H, td, J8 and 7 Hz, C3-H), 6.66 (1H, dd, J16 and 5 Hz, C6-H), 7.29 (1H, dd, J16 and 2½ Hz, C6-H), 7.40 (2H, q, J7 Hz, S-$CH_2$-), 7.82 (2H, dd, J8 and 6 Hz, C4-Hs) and 8.75 (3H, t, J7 Hz, $CH_3$ of SEt); ($M^+$ at m/e 229.0765. $C_{10}H_{15}NO_3S$ requires 229.0773).

Isomer B

(11) (0.01 g) was a gum: $\nu_{max}$($CHCl_3$) 2960, 1770 and 1750 (sh)$cm^{-1}$; τ($CDCl_3$) 5.69 (1H, d, J6 Hz, C2-H), 6.1-6.3 (1H, m, C5-H), 6.28 (3H, s, $OCH_3$), 6.72 (1H, dd, J15 and 4½ Hz, C6-H), 7.26 (1H, dd, J15 and 2 Hz, C6-H), 7.41 (2H, q, J7 Hz, S—$CH_2$—), 7.45 (1H, q, J6 Hz, C3-H), 8.31 (1H, dd, J8 and 6 Hz, C4-H), 8.47 (1H, dd, J8 and 6 Hz, C4-H) and 8.76 (3H, t, J7 Hz, $CH_3$ of SEt); ($M^+$ at m/e 229.0768. $C_{10}H_{15}NO_3S$ requires 229.0773).

Isomer C

(12) (0.024 g) could be crystallized from ethyl acetate/60°-80° petroleum ether; m.p. 89°-90°; $\nu_{max}$($CHCl_3$) 2960, 1770 and 1745 $cm^{-1}$; τ($CDCl_3$) 5.92 (1H, d, J7

Hz, C2-H), 6.1-6.6 (2H, m, C3-H and C5-H), 6.25 (3H, s, $OCH_3$), 6.89 (1H, dd, J16 and 4 Hz, C6-H), 7.16 (1H, dd, J16 and 2½ Hz, C6-H), 7.40 (2H, q, J7 Hz, S-$CH_2$), 7.71 (1H, dt, J12 and 6 Hz, C4-H), 8.06 (1H, td, J12 and 10 Hz, C4-H) and 8.75 (3H, t, J7 Hz, $CH_3$ of SEt); (Found; C, 52.0; H, 6.5; N, 5.9%. $C_{10}H_{15}NO_3S$ requires C, 52.4; H, 6.6 and N, 6.1%).

EXAMPLE 6

Benzyl 3-ethylthio-7-oxo-1-azabicyclo[3,2,0]heptane-2-carboxylate

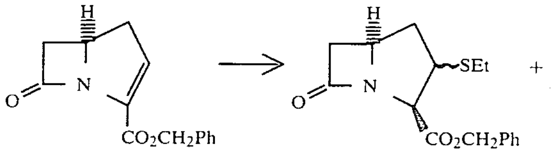

(13) (14) and (15)

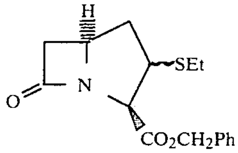

(16)

Benzyl 7-oxo-1-azabicyclo[3,2,0]hept-2-ene-2-carboxylate (13) (0.060 g) was stirred in dry dimethylformamide (1 ml) at ambient temperature and treated with ethane thiol (0.10 ml) and then potassium carbonate (0.019 g). The reaction mixture was concentrated in vacuo after 15 minutes and the residue was partitioned between ethyl acetate and brine. The organic phase was dried over sodium sulphate and then concentrated. The crude material was chromatographed on silica gel 60 (<230 mesh), eluting with 60°-80° petrol/ethyl acetate 7:3 to give two fractions containing the required compounds. The first fraction (0.038 g) was a mixture of isomers A (14) and B (15) in a 4:1 ratio; $\nu_{max}$($CHCl_3$) 2980, 1770 and 1750 $cm^{-1}$; $\tau$($CDCl_3$) for major isomer (14) 2.71 (5H, s, phenyl), 4.88 (2H, s, benzyl $CH_2$), 5.28 1H, d, J7 Hz, C2-H), 5.94 (1H, tdd, J6.5 and 2½ Hz, C5-H), 6.45 (1H, td, J9 and 7 Hz, C3-H), 6.67 (1H, dd, J16 and 5 Hz, C6-H), 7.30 (1H, dd, J16 and 2½ Hz, C6-H), 7.46 (2H, q, J7 Hz, S-$CH_2$), 7.84 (2H, dd, J9 and 6 Hz, C4-H's) and 8.83 (3H, t, J7 Hz, $CH_3$ of SEt); the only obvious signal for the minor isomer B (15) was 5.65 (d, J5 Hz, C2-H); (M+ for mixture at m/e 305.1057. $C_{16}H_{19}NO_3S$ requires 305.1085.)

The second fraction was the pure β-carboxylate isomer C (16) (0.017 g) which was obtained as colourless needles from ethyl acetate/60°-80° petroleum ether; m.p. 62°-64°; $\nu_{max}$($CHCl_3$) 2960, 1770 and 1740 $cm^{-1}$. $\tau$($CDCl_3$) 2.70 (5H, s, phenyl) 4.83 (2H, s, benzyl $CH_2$), 5.90 (1H, d, J7 Hz, C2-H), 6.2-6.5 (2H, m, C3-H and C5-H), 6.92 (1H, dd, J16 and 4 Hz, C6-H), 7.21 (1H, dd, J16 and 2½ Hz, C6-H), 7.46 (2H, q, J7 Hz, S-$CH_2$), 7.75 (1H, dt, J12 and 6 Hz, C4-H), 8.07 (1H, td, J12 and 10 Hz, C4-H) and 8.83 (3H, t, J7 Hz, $CH_3$ of SEt). (Found: C, 62.8; H, 6.2; N, 4.3%. $C_{16}H_{19}NO_3S$ requires C, 62.9; H, 6.3 and N, 4.6%.

EXAMPLE 7

Benzyl 7-oxo-3-phenylthio-1-azabicyclo[3,2,0]heptane-2-carboxylate

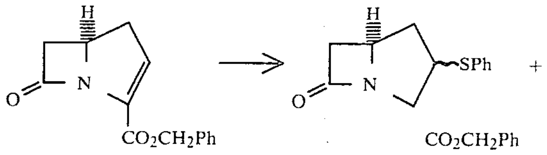

(13) (5) and (6)

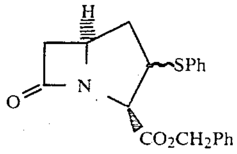

(8)

Crude benzyl 7-oxo-1-azabicyclo[3,2,0]hept-2-ene-2-carboxylate prepared from an ethyl acetate solution of 4-allyl-1-(1-benzyloxycarbonyl-1-triphenylphosphoranylidenemethyl)azetidin-2-one (1.00 g) by ozonolysis and cyclisation was dissolved in dry dimethylformamide (5 ml) treated successively with thiophenyl (0.20 ml) and potassium carbonate (0.133 g) with stirring. After a period of 1 hour the solution was concentrated under reduced pressure and the residue treated with ethyl acetate. It was then washed with brine, dried over sodium sulphate and concentrated. Chromatography on silica gel 60 (<230 mesh) eluting with 60°-80° petroleum ether/ethyl acetate 7:3 grading to 6:4 gave two fractions containing diastereoisomers of the title compound. The least polar fraction (0.183 g) was an approximately 4:1 mixture of isomers A (5) and B (6); $\nu_{max}$($CHCl_3$) 3000, 1760 and 1740 (sh); $\tau$($CDCl_3$) for major isomer A (5), 2.6-2.9 (10H, m, phenyls), 4.88 (2H, s, benzyl $CH_2$), 5.26 (1H, d, J7 Hz, C2-H), ca 5.90 (1H, br m, C5-H), 6.10 (1H, td, J9 and 7 Hz, C3-H), 6.69 (1H, dd, J16 and 5 Hz, C6-H), 7.32 (1H, dd, J16 and 2½ Hz, C6-H), 7.73 (1H, dd, J9 and 7 Hz, C4-H) and 7.77 (1H, dd, J9 and 4 Hz, C4-H); minor isomer B (6) had 5.62 (d, J 5 Hz, C2-H); (M+ for mixture at m/e 353.1102. $C_{20}H_{19}NO_3S$ requires 353.1085). The more polar fraction (0.102 g) was isomer C (8) which could be crystallized from diethyl ether; m.p. 84°-85°; $\hat{\nu}_{max}$ ($CHCl_3$) 3000, 1765 an d 1740 $cm^{-1}$; $\tau$($CDCl_3$) 2.6-2.9 (10H, m, phenyls), 4.81 (2H, s, benzyl $CH_2$), 5.84 (1H, d, J7 Hz, C2-H), 6.04 (1H, ddd, J12, 7 and 5 Hz, $C_3$-H), 6.2-6.5 (1H, m, C5-H), 6.90 (1H, dd, J16 and 4 Hz, C6-H), 7.19 (1H, dd, J16 and 2½ Hz, C6-H), 7.64 (1H, dt, J12 and 5 Hz, C4-H) and 7.95 (1H, td, J12 and 10 Hz, C4-H); (Found; C, 68.1; H, 5.6; N, 3.9% $C_{20}H_{19}NO_3S$ requires C, 68.0; H, 5.4 and N, 4.0%).

EXAMPLE 8

2,2,2-Trichloroethyl 6-(3-methoxycarbonyl-2-propen-1-yl)-7-oxo-3-(2,4,5-trichlorophenylthio)-1-azabicyclo[3,2,0]heptane-2-carboxylate

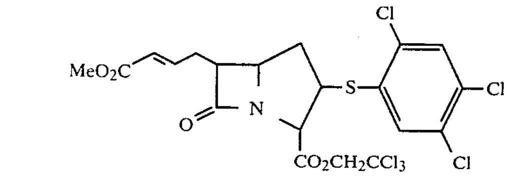

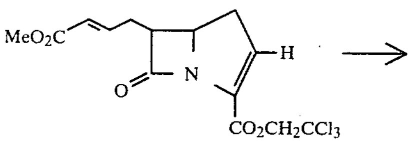

(17)

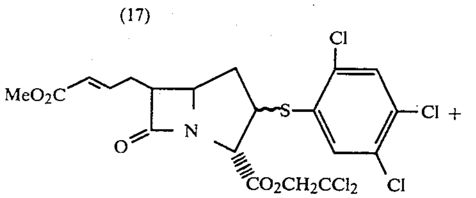

(18) and (19)

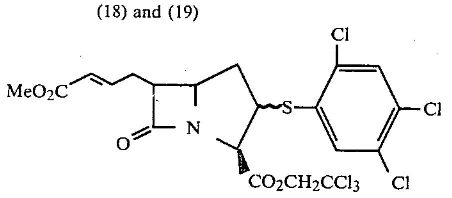

(20)

2,2,2-Trichloroethyl 6-(3-methoxycarbonyl-2-propen-1-yl)-7-oxo-1-azabicyclo[3,2,0]hept-2-ene-2-carboxylate (17) (0.05 g) was dissolved in dry dimethylformamide (1 ml). Potassium carbonate (0.013 g) was added followed by 2,4,5-trichlorophenylthiol (0.1 g). After stirring at room temperature for 4 hr. the reaction mixture was diluted with ethyl acetate (30 ml), washed with brine, dried ($MgSO_4$) and evaporated to give a gum (0.1 g). Chromatography on Merck Kieselgel 60 (<230 mesh) eluting with ethyl acetate-petroleum ether (3:7) gave three separable isomers (18), (19) and (20) of the title compound. Isomer A (18), (0.021 g), m.p. 102°-104° (ex $Et_2O$) $\nu_{max}$($CHCl_3$) 1770, 1720, 1655 $cm^{-1}$. δppm ($CDCl_3$) 2.00-2.80 (4H, m, C4-$H_2$, C6 side-chain $CH_2$). 3.70 (3H, s, OMe), 3.52-3.80 (2H, m, C6-H, C3-H), 4.33 (1H, dt, J5 and 8 Hz, C5-H), 4.64 and 4.83 (2H, ABq, J12 Hz, $\underline{CH_2}CCl_3$), 4.80 (1H, d, J6 Hz, C2-H), 5.85 (1H, d, J15 Hz with further slight coupling $MeO_2C—\underline{CH}=CH$—trans), 6.87 (1H, dt, J15, 9 Hz, $MeO_2C—CH=\underline{CH}—CH_2$) 7.47-7.52 (2H, Ar). (Found; M, 592,8898. $C_{20}H_{17}Cl_6NO_5S$ requires M, 592.8958). Isomer B (19) (0.023 g), m.p. 104°-105° (ex. $Et_2O$), $\nu_{max}$($CHCl_3$) 1770, 1720, 1660 $cm^{-1}$. δ ppm ($CDCl_3$) 2.00-2.80 (4H, m, C4-$H_2$, C6-side chain $CH_2$), 3.70 (3H, s, OMe), 3.55-3.88 (1H, m, C3-H), 3.90-4.32 (2H, m, C5-H, C6-H), 4.44 (1H, d, J4 Hz, C2-H), 4.70 (2H, s, $\underline{CH_2}CCl_3$) 5.83 (1H, d, J15 Hz, $MeO_2C—\underline{CH}=CH$—trans), 6.86 (1H, dt, J15 and 8 Hz, $CH=\underline{CH}—CH_2$), 7.49-7.58 (2H, Ar). (Found; M, 592.8990. $C_{20}H_{17}Cl_6NO_5S$ requires M, 592.8958). Isomer C (20) (0.021 g), $\nu_{max}$($CHCl_3$) 1775, 1760 (sh), 1720 1660 $cm^{-1}$. δ ppm ($CDCl_3$) 2.00-2.80 (4H, m, C4-$H_2$, C6-side-chain $CH_2$), 3.30-3.55 (1H, m, C3-H), 3.70 (3H, s, OMe), 3.84-4.15 (2H, m, C5-H, C6-H), 4.31 (1H, d, J8 Hz, C2-H), 4.70 and 4.89 (2H, ABq, J12 Hz, $CH_2CCl_3$), 5.84 (1H, d, J15 Hz, $MeO_2C—\underline{CH}=CH$ trans), 6.86 (1H, dt, J15 and 8 Hz, $CH=\underline{CH}—CH_2$), 7.47-7.48 (2H, Ar.). (Found: M, 592.8931. $C_{20}H_{17}Cl_6NO_5S$ requires M, 592,8958).

EXAMPLE 9 p-Bromophenacyl 6-(3-methoxycarbonyl-2-propen-1-yl)-3-ethylthio-7-oxo-1-azabicyclo[3,2,0]heptane-2-carboxylate

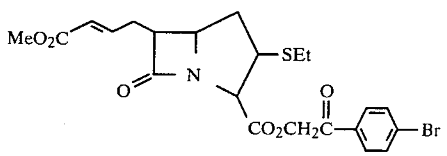

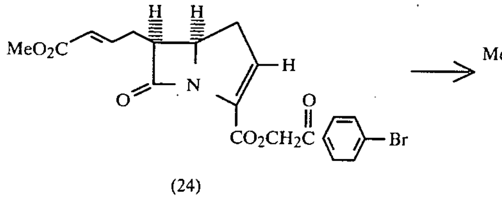

(24)

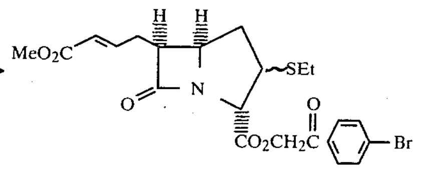

(25) and (26)

+

-continued

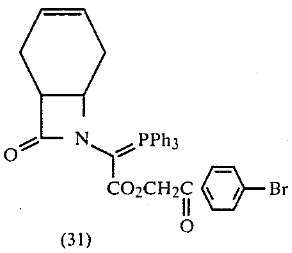

(31)

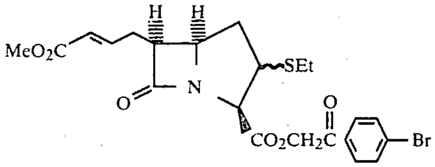

(27)

p-Bromophenacyl 6-(3-methoxycarbonyl-2-propen-1-yl)-7-oxo-1-azabicyclo[3,2,0]hept-2-ene-2-carboxylate (24) was prepared as in Example 10 from the phosphorane (31) (0.7 g). The crude ester (24) in anhydrous dimethylformamide (2 ml) was treated with ethanethiol (0.075 g, 90 $\mu$l) in the presence of potassium carbonate (0.167 g). The reaction mixture was stirred at room temperature for 40 min. Removal of the dimethylformamide in vacuo (oil pump; room temperature) gave an oil (1.25 g) which was chromatographed on Kieselgel 60 (Merck; <230 mesh). Elution of the column with ethyl acetate-petroleum ether (7:13) gave three isomers (25), (26) and (27) of the title compound. Leading fractions gave gummy crystals (0.21 g) shown (n.m.r. spectrum) to be a mixture of isomers (25) and (26) in ca 2:1 ratio. Crystallisation (chloroform-petroleum ether afforded:

Isomer A

(25) (0.125 g) m.p. 133°-134°, $\nu_{max}(CHCl_3)$ 1760, 1720 (sh) 1710, 1660, 1590 $cm^{-1}$; $\delta(CDCl_3)$ 1.24 (3H, t, J7 Hz), 2.05-2.30 (2H, m, C4-$H_2$), 2.4-2.8 (2H, m, C6 side-chain $CH_2$) 2.64 (2H, q, J7 Hz, —S—$\underline{CH_2}CH_3$), 3.27-3.65 (2H, m, C3-H and C6-H), 3.69 (3H, s), 4.05 (1H, m, C5-H), 4.80 (1H, d, J 7 Hz, C2-H), 5.20 and 5.41 (2H, ABq, J 17 Hz) 5.83 (1H, d, J15 Hz), 6.87 (1H, dt, J15, 6 Hz), 7.56 (2H, d, J8 Hz) and 7.74 (2H, d, J8 Hz). (Found; C, 51.8; H, 4.5; N, 2.7. $C_{22}H_{24}BrNO_6S$ requires C, 51.8; H, 4.7; N, 2.7%). Evaporation of the mother liquors of the leading fractions yielded:

Isomer B

(26) as a gum (0.068 g), $\nu_{max}(CHCl_3)$ 1760 (st), 1720, 1710, 1660, 1590 $cm^{-1}$; $\delta(CDCl_3)$ 1.28 (3H, t, J 7 Hz), 1.2-2.3 (2H, m), 2.4-2.8 (2H, m, C6 side-chain $CH_2$), 2.72 (2H, q, J 7 Hz, S—$\underline{CH_2}CH_3$), ca 3.6 br (1H, C6-H), 3.72 (3H, s), 4.1 br (2H, m, C5-H and C3-H), 4.46 (1H, d, J 5 Hz, C2-H), 5.20 and 5.41 (2H, ABq, J 17 Hz) 5.83 (1H, d, J 15 Hz), 6.87 (1H, dt, J 15, 6 Hz), 7.58 (2H, d, J 8 Hz) and 7.72 (2H, d, J 8 Hz). Later fractions from the column gave:

Isomer C

(27) as a white foam (0.1 g), $\nu_{max}(CHCl_3)$ 1765, 1750, 1720 (sh), 1710, 1660 and 1590 $cm^{-1}$; $\delta(CDCl_3)$ 1.25 (3H, t, J 7 Hz), 2.10 (2H, t, J 9 Hz, C4-$H_2$), 2.64 (4H, m, S—$\underline{CH_2}CH_3$ and C6 side-chain $CH_2$), 3.36 (1H, m, C6-H), 3.5-4.0 (2H, m, C3-H and C5-H), 3.69 (3H, s), 4.23 (1H, d, J 8 Hz, C2-H), 5.25 and 5.45 (2H, ABq, J 16 Hz), 5.82 (1H, d, J 15 Hz), 6.87 (1H, dt, J 15, 6 Hz), 7.55 (2H, d, J 8 Hz) and 7.75 (2H, d, J 8 Hz).

EXAMPLE 10

(a) 7-(1-Hydroxy-1-p-bromophenacyloxycarbonylmethyl)-8-oxo-7-azabicyclo[4,2,0]oct-3-ene

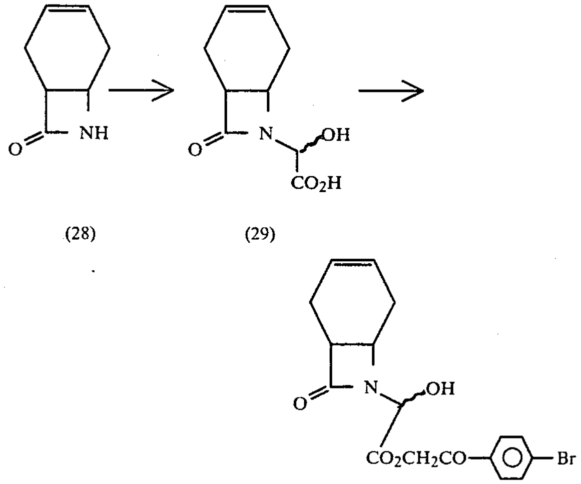

(28) (29) (30)

The azetidinone (28) (0.4 g) in anhydrous dimethylformamide (2 ml) was stirred with glyoxylic acid hydrate (0.32 g) in the presence of hexamethylphosphorictriamide (0.1 ml) and molecular sieves (3A; 4 pieces) for 5h. Potassium carbonate (0.226 g) was added, and the solution stirred until effervescence had ceased (5 min). p-Bromophenacylbromide (1.00 g; 1.05 equiv.) in dimethylformamide (1.0 ml) and hexamethylphosphorictriamide (0.25 ml) was added, and the solution stirred overnight. The solution was diluted with ethyl acetate, washed with saturated aqueous sodium chloride solution (x 3), dried ($Na_2SO_4$) and evaporated to give a gum (1.9 g) which was chromatographed on Kieselgel. Elution of the column with ethyl acetate-petroleum ether (1:1) gave the glyoxylate ester (30). Isomer I as a foam, which slowly crystallised (ethyl acetate-petroleum ether) as needles (0.60 g) (47%) m.p. 135°-136°, $\nu_{max}(CHCl_3)$ 3250br, 1760sh, 1750, 1710, 1590, 970 $cm^{-1}$; $\delta(d_6$ DMSO) 1.9-2.8 (4H, m), 3.35 (1H, m), 4.17 (1H, m) 5.51 (1H, d, J 6.5 Hz; sharpens to a singlet on $D_2O$ exchange) 5.55 (2H, s, phenacyl $CH_2$), 5.72br (2H, s), 6.81 (1H, d, J 6.5H, $D_2O$ exchangeable), 7.75 (2H, d, J 9 Hz) and 7.90 (2H, d, J 9 Hz) (Found; C, 51.9; H, 4.2; N, 3.6; Br, 20.00. $C_{17}H_{16}BrNO_5$ requires C, 51.8; H, 4.1; N, 3.6; Br, 20.3%).

Continued elution of the column gave the more polar Isomer II, which crystallised (ethyl acetate-petroleum ether) as platelets (0.55 g) (43%) m.p. 144°-146°, $\nu_{max}$($CHCl_3$) 3200br, 1760sh, 1750, 1710, 1590, 965 $cm^{-1}$; δ($d_6$ DMSO) 1.9–2.8 (4H, m), 3.33 (1H, m) 4.15 (1H, m), 5.47 (1H, d, sharpens to a singlet on $D_2O$ exchange), 5.51 (2H, s, phenacyl $CH_2$), 5.71br (2H, s), 6.90 (1H, d, J 7 Hz, $D_2O$ exchangeable), 7.73 (2H, d, J 9 Hz), and 7.91 (2H, d, J 9 Hz). (Found; C, 51.7; H, 4.3; N, 3.3; Br, 20.6 $C_{17}H_{16}BrNO_5$ requires C, 51.8; H, 4.1; N, 3.6; Br, 20.3%).

(b)

7-(1-p-bromophenacyloxycarbonyl-1-triphenylphosphoranylidenemethyl)-8-oxo-7-azabicyclo[4,2,0]oct-3-ene

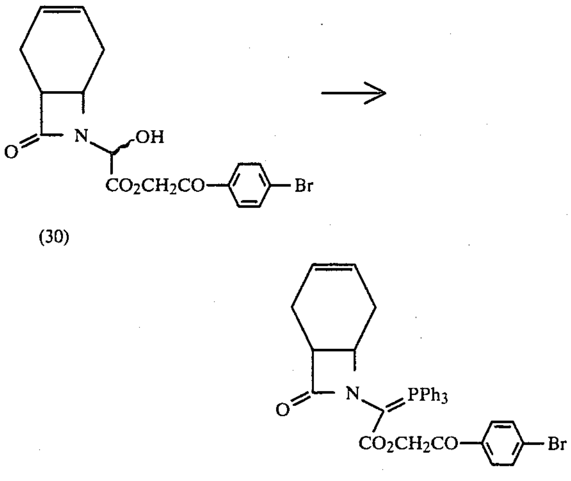

(30)

(31)

The glyoxylate p-bromophenacyl ester (30) (0.383 g; 1:1 isomer ratio) in THF (8 ml) was treated with lutidine (230 μl), followed by thionyl chloride (139 μl) at −20° for 3.5 hr. The material was rapidly filtered through celite, washed with ethyl acetate, and the filtrate and washings evaporated in vacuo. The residue in dioxan (4 ml, anhydrous) was treated with triphenylphosphine (0.51 g) and lutidine (230 μl) at room temperature overnight. Chromatography on Kieselgel (elution with ethyl acetate petroleum ether, 7:3) gave the phosphorane (31) as a gum (0.536 g) which crystallised from ethyl acetate-ether-petroleum ether as small rods (0.499 g) (80%) m.p. 200°–202°, $\nu_{max}$ ($CHCl_3$) 1740st, 1710, 1620, 1590, 1480 $cm^{-1}$. (Found: C, 65.7; H, 4.7; N, 2.0; Br, 12.1. $C_{35}H_{29}BrNO_4P$ requires C, 65.8; H, 4.6; N, 2.2; Br, 12.5%).

(c) p-Bromophenacyl 6-(3-methoxycarbonyl-2-propen-1-yl)-7-oxo-1-azabicyclo[3,2,0]hept-2-ene-carboxylate

(24) was prepared from the phosphorane (31) (0.104 g) and isolated by the method described in Example 12.

The bicyclic ester (24) (35 mg) (50%) crystallised from ethyl acetate-ether-petroleum ether (31 mg) m.p. 134°–136°, $\nu_{max}$ 1785, 1725sh, 1715, 1700, 1660, 1610, 1590 $cm^{-1}$; $\lambda_{max}$ (EtOH) infl 275, 258 (ε21900), 210 (26,000); δ($CDCl_3$) 2.45–2.9 (2H, m, C6 side-chain $CH_2$), 2.74 (2H, dd, J 9, 3 Hz, C4-$H_2$), 3.68 (3H, s), 3.6–3.9 (1H, m, $C_6$-H), 4.40 (1H, dt, J 9, 6 Hz, C5-H), 5.36 (2H, s), 5.80 (1H, dt, J 15, 1 Hz), 6.60 (1H, t, J 3 Hz, C3-H), 6.86 (1H, dt, J 15, 6 Hz), 7.55 (2H, d, J 9 Hz) and 7.74 (2H, d, J 9 Hz). (Found; C, 53.4; H, 4.1; N, 3.2; Br, 17.9. $C_{20}H_{18}BrNO_6$ requires C, 53.6; H, 4.0; N, 3.1; Br, 17.8%).

EXAMPLE 11

Benzyl 6-(2-oxoethyl)-7-oxo-1-azabicyclo[3,2,0]hept-2-ene-2-carboxylate

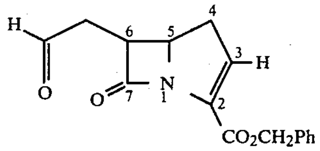

(i)

7-(1-Hydroxy-1-benzyloxycarbonylmethyl)-8-oxo-7-azabicyclo[4,2,0]oct-3-ene

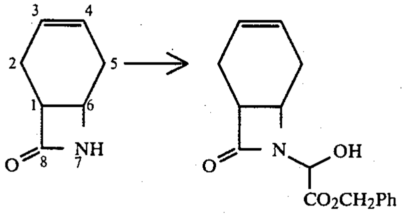

(28) (32)

Benzyl glyoxylate (2.73 g) was refluxed in benzene (25 ml) with provision for the removal of water. After 45 minutes 8-oxo-7-azabicyclo[4,2,0]oct-3-ene (28) (ref: I. A. Paquette and T. Kakihana, *J. Amer. Chem. Soc.*, 1968, 20, 2897) (1.23 g) was added and refluxing continued for 3 hours. Removal of solvent under reduced pressure followed by chromatography gave two separate isomers of the alcohol (32) (90%) Isomer I, m.p. 92°–93°, $\nu_{max}$ ($CHCl_3$) 3450, 1750 (b) $cm^{-1}$. δ ppm ($CDCl_3$) 1.76–2.73 (4H, m, 2-$CH_2$), 3.12–3.33 (1H, m, β-lactam proton), 3.76–3.93 (1H, m, β-lactam proton), 4.40 (1H, d, J6 Hz, exch. $D_2O$), 5.16 (2H, s, $CH_2$), 5.47 (1H, d, J 6 Hz collapsing to s on $D_2O$ exch. CH-OH), 5.67–5.83 (2H, m, CH=CH), 7.34 (5H, Ar). $M^+$ at m/e 287 (Found: C, 66.2; H, 5.9; N, 4.9. $C_{16}H_{17}NO_4$ requires C, 66.9; H, 6.0; N, 4.9%). Isomer II, m.p. 100°–101°, $\nu_{max}$ ($CHCl_3$) 3450, 1750 (b), δ ppm ($CDCl_3$) 1.80–2.63 (4H, m, 2-$CH_2$), 3.13–3.36 (1H, m, β-lactam proton), 3.93–4.13 (1H, m, β-lactam proton), 4.20 (1H, bs, exch, $D_2O$), 5.16 (2H, s, $CH_2$), 5.50 (1H, b, sharpening to s on $D_2O$ exchange), 5.50–6.00 (2H, m, CH=CH), 7.34 (5H, Ar). (Found; C, 67.2; H, 6.0; N, 4.8. $C_{16}H_{17}NO_4$ requires C, 66.9; H, 6.0; N, 4.9%).

(ii)
7-(1-Benzyloxycarbonyl-1-triphenylphosphoranylidenemethyl)-8-oxo-7-azabicyclo[4,2,0]oct-3-ene

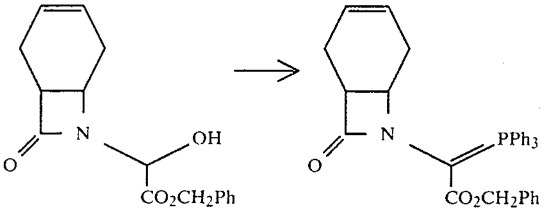

(32) (33)

The alcohol (32) as mixture of isomers, (2.2 g) in THF (50 ml) was cooled to −20°. Lutidine (1.5 g) was added followed by thionyl chloride (1.0 ml). After stirring at −20° for 20 min, the solution was filtered and evaporated to dryness; final removal of the last traces of excess thionyl chloride was by evaporation twice from toluene. The residue in dioxan (20 ml) was treated with triphenylphosphine (4.02 g) and lutidine (1.64 g) and left stirring overnight at room temperature. The lutidine hydrochloride was separated by filtration, and the filtrate evaporated to dryness and chromatographed to give (33, 1.5 g) as an amorphous solid, $\nu_{max}$ ($CHCl_3$) 1730, 1620 $cm^{-1}$.

(iii) Benzyl
6-(2-oxoethyl)-7-oxo-1-azabicyclo[3,2,0]hept-2-ene-2-carboxylate

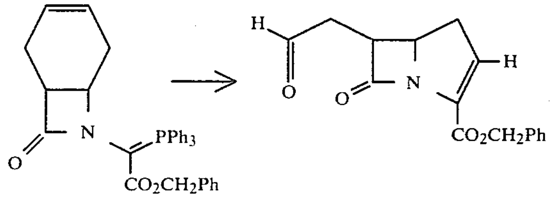

(33) (34)

The phosphorane (33, 0.2 g) in ethyl acetate (10 ml) was treated with trifluoroacetic acid (0.25 ml). The solution was cooled (−65°) and treated with ozone until the reaction solution showed a slight blue colouration. Argon was blown through the solution to remove excess ozone, and then triphenylphosphine (0.1 g) was added. After five minutes the reaction was transferred to an ice-bath and stirred vigorously with aqueous (5%) sodium bicarbonate solution (10 ml) for 45 minutes. The organic phase was separated, dried, evaporated and chromatographed to give the product (34, 42 mg) as a gum $\nu_{max}$ ($CHCl_3$) 1780, 1725, 1610 $cm^{-1}$. δ ppm ($CDCl_3$) 2.50–3.00 (4H, m, 2×$CH_2$), 3.87–4.11 (1H, m, C6-H), 4.46 (1H, dt, J 6 Hz, 9 Hz C5-H; collapses to d, J 6 Hz on irradiation at δ 2.60); 5.21 (2H, s, benzyl $CH_2$), 6.45 (1H, t, J 2 Hz, C3-H), 7.30 (5H, s, Ar), 9.70 (1H, s, CHO). $M^+$ at m/e 285.

EXAMPLE 12

Benzyl
6-(3-methoxycarbonyl-2-propen-1-yl)-7-oxo-1-azabicyclo[3,2,0]hept-2-ene-2-carboxylate

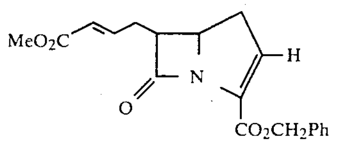

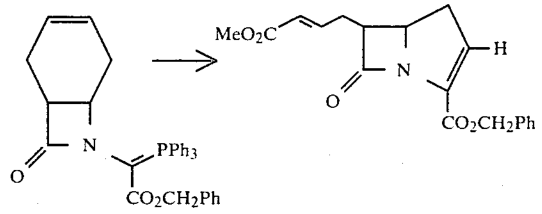

(33) (34a)

The phosphorane (33,0.2 g) in ethyl acetate (10 ml) was treated with trifluoroacetic acid (0.25 ml) and subjected to ozonolysis and work up as in Example 11 (iii) the crude product containing (34a) was dissolved in chloroform (5 ml) and treated with methoxycarbonylmethylene triphenylphosphorane (0.124 g) and left for 1 hour at room temperature. The solution was evaporated to dryness and chromatographed to give the product (34a) (45 mg), m.p. 81°–82° (from ether), $\nu_{max}$ ($CHCl_3$) 1780, 1720, 1650, 1610 $cm^{-1}$. δ ppm ($CDCl_3$) 2.68 (2H, dd, J 9 Hz, 3 Hz, C4-$CH_2$; collapsing to d J 3 Hz on irradiation at δ 4.3); 2.40–2.90 (2H, m, C6 sidechain $CH_2$), 3.67 (3H, s, OMe), 3.67–3.74 (1H, m, C6-H), 4.35 (1H, dt, J 6 Hz, 9 Hz, C5-H, collapsing to d J 6 Hz on irradiation at δ 2.6); 5.20 (2H, s, benzyl $CH_2$), 5.80 (1H, d, J 15 Hz, trans $MeO_2C\underline{CH}{=}CH$—), 6.45 (1H, t, J 3 Hz, C3-H, collapsing to s on irradiation at δ 2.6), 6.84 (1H, dt, J 15 Hz, 6 Hz, trans —$CH{=}\underline{CH}$—$CH_2$), 7.32 (5H, s, Ar). (Found; M, 341.1270. $C_{19}H_{19}NO_5$ requires M, 341.1263).

EXAMPLE 13

2,2,2-Trichloroethyl-6-(3-methoxycarbonyl-2-propen-1-yl)-7-oxo-1-azabicyclo[3,2,0]hept-2-ene-2-carboxylate

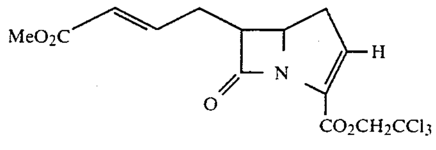

(i)

7-(1-Hydroxy-1-2,2,2-trichloroethoxycarbonylmethyl)-8-oxo-7-azabicyclo[4,2,0]oct-3-ene

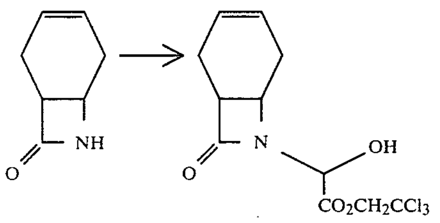

(28) (35)

2,2,2-Trichloroethylglyoxylate (0.78 g) was refluxed in benzene (15 ml) with provision for the removal of water (0.5 hrs). The azetidinone (28) (0.287 g) was added and refluxing continued for 1 hour. Removal of the solvent and chromatography gave the alcohol (35) (80%). Isomer I m.p. 85°-88°, $\nu_{max}$ ($CHCl_3$) 3500, 1770 (ester); 1750 ($\beta$-lactam) $cm^{-1}$. $\delta$ ppm ($CDCl_3$) 2.00-2.80 (4H, m, $2\times CH_3$), 3.30-3.40 (1H, m, $\beta$-lactam proton), ca 3.70 (1H, bs, exch, $D_2O$, OH), 4.10-4.25 (1H, m, $\beta$-lactam proton), 4.80 (2H, s, $CH_2$), 5.50 (1H, s, CH), 5.72-5.91 (2H, m, CH=CH). (Found; C, 40.3; H, 3.7; N, 4.2. $C_{11}H_{12}Cl_3NO_4$ requires C, 40.2; H, 3.7 N, 4.3%). Isomer II m.p. 119°-121°, had similar spectroscopic properties.

(ii)

7-(1-Trichloroethoxycarbonyl-1-triphenylphosphoranyl idenemethyl)-8-oxo-7-azabicyclo[4,2,0]oct-3-ene

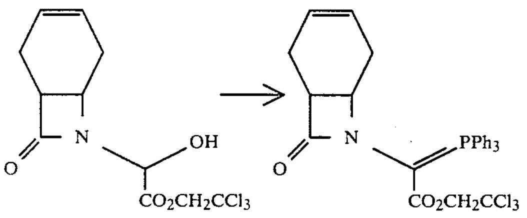

(35) (36)

The alcohol (35) (6.0 g as a mixture of isomers) in THF (75 ml) was converted to the chloride as in example 11 (ii) using thionyl chloride (2.61 ml) and lutidine (4.25 ml). The crude chloride in dioxan (75 ml) was reacted with triphenylphosphine (9.6 g) and lutidine (4.25 ml) as for the benzyl ester to give the phosphorane (36) (6.0 g) as a foam, $\nu_{max}$ ($CHCl_3$) 1740 1630 $cm^{-1}$.

(iii)

2,2,2-Trichloroethyl-6-(3-methoxycarbonyl-2-propen-1-yl)-7-oxo-1-azabicyclo[3,2,0]hept-2-ene-2-carboxylate

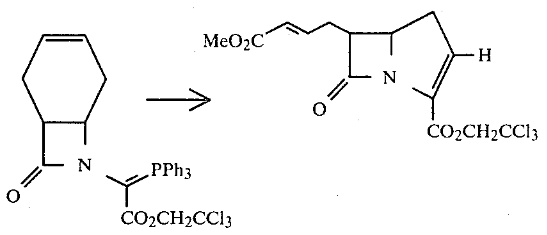

(36) (17)

The phosphorane (36) (0.2 g) was dissolved in EtAc (10 ml) and trifluoroacetic acid (1 ml) and subjected to ozonolysis and work up as for the benzyl ester in example 11 (iii) The crude reaction product in chloroform (3 ml) was treated with carbomethoxymethylene triphenylphosphorane (117 mg) and left at R.T. for 0.5 hours. Evaporation and chromatography gave (17) (40 mg) m.p. 101°-102°, $\nu_{max}$ ($CHCl_3$) 1785, 1735, 1720, 1660, 1615 $cm^{-1}$ $\delta$ ppm ($CDCl_3$) 2.74 (2H, dd, J 10 Hz, 3 Hz, C4-$CH_2$), 2.30-2.90 (2H, m, $CH_2$), 3.65 (3H, s, OMe), 3.60-3.90 (1H, m, C6-H), 3.38 (1H, dt, J 6 Hz, 10 Hz, C5-H), 4.70 and 4.86 (2H, ABq, J 12 Hz, $CH_2CCl_3$), 5.80 (1H, d, J 15 Hz plus further slight coupling, trans $MeO_2C$—CH=CH—$CH_2$), 6.60 (1H, t, J 3 Hz, C3-H), 6.84 (1H, dt, J 15 Hz, 6 Hz, trans CH=CH—$CH_2$). $\lambda_{max}$ (EtOH) 209 nm ($\epsilon$12,100), 273 nm ($\epsilon$3110).

EXAMPLE 14

Benzyl 6-(2-hydroxy-2-propyl)-7-oxo-1-azabicyclo[3,2,0]hept-2-ene-2-carboxylate

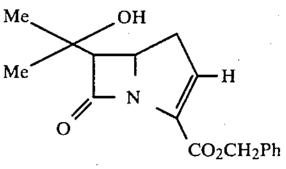

(i)

4-Allyl-1-(1-benzyloxycarbonyl-1-triphenylphosphoranyl idenemethyl)-3-(2-hydroxy-2-propyl)azetidin-2-one

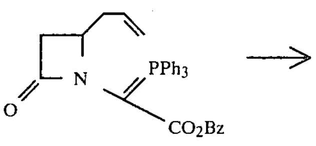

(37)

-continued

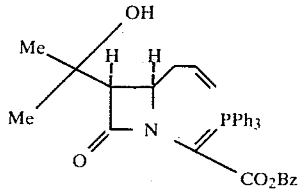

(38)

+

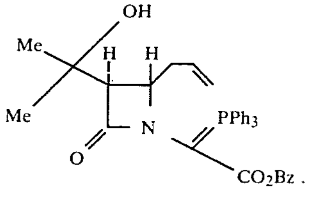

(39)

A solution of N-isopropylcyclohexylamine (0.60 g) in dry tetrahydrofuran (10 ml) was stirred under argon and cooled to −78° C. This was treated with a 2.5 M solution of n-butyl lithium in n-hexane (1.70 ml). After ten minutes, a solution of 4-allyl-1-(1-benzyloxycarbonyl-1-triphenylphosphoraylidenemethyl)azetidin-2-one (37) (1.00 g) in dry tetrahydrofuran (10 ml) was added. Five minutes was allowed for the formation of the C(3) carbanion which was then quenched by the addition of dry acetone (0.71 ml). The cooling bath was then removed and the mixture stirred for a further ten minutes before it was neutralised with acetic acid (0.56 g). The solvent was evaporated under reduced pressure and the residue chromatographed on silica gel 60 (<230 mesh), eluting with ethyl acetate/60°-80° petroleum ether mixtures grading from 1:1 to 7:3. This gave a mixture of the cis and trans-isomers of 4-allyl-1-(1-benzyloxycarbonyl-1-triphenylphosphoranylidenemethyl)-3-(2-hydroxy-2-propyl)azetidin-2-one (0.76 g; 71%) (38) and (39), $\nu_{max}$ ($CHCl_3$) 3000, 1735 and 1620 $cm^{-1}$.

It was possible to obtain a substantial separation of the cis- and trans-isomers by further chromatography on silica gel 60 (<230 mesh), eluting with ethyl acetate/60°-80° petroleum ether mixtures grading from 1:1 to 7:3.

(ii) Benzyl 6-(2-hydroxy-2-propyl)-7-oxo-1-azabicyclo [3,2,0]hept-2-ene-2-carboxylate (a)

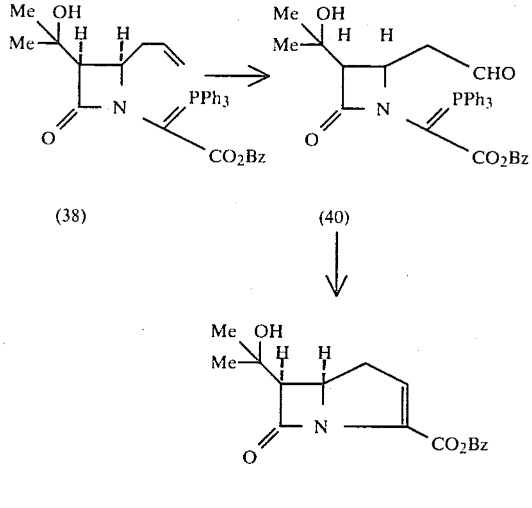

(38) (40) (41)

The cis-isomer of 4-allyl-1-(1-benzyloxycarbonyl-1-triphenylphosphoranylidenemethyl)-3-(2-hydroxy-2-propyl)azetidin-2-one (38) (0.188 g) was dissolved in ethyl acetate (14 ml). An excess of trifluoroacetic acid (0.37 g) was added and the mixture cooled to −78° C. Ozone was passed into the reaction mixture until it was pale blue in colour. Argon was then bubbled through the solution until all the excess ozone had been removed. A solution of triphenylphosphine (0.085 g) in ethyl acetate was added and argon bubbled through the mixture for a further ten minutes. The reaction flask was then transferred to an ice bath and a saturated aqueous solution of sodium bicarbonate (20 ml) was added and the mixture stirred vigourously under argon for thirty minutes. The ethyl acetate layer was separated, washed with brine and dried.

The solution containing (40) was left at room temperature for thirty-six hours. During this time, the cyclisation reaction was followed by thin layer chromatography and it was seen that a slow moving spot gradually decreased in intensity along with an increase in the intensity of a faster moving spot which corresponded to the required cis-product. (41). The ethyl acetate was evaporated off under reduced pressure and the residue was purified by chromatography on silica gel 60 (<230 mesh), eluting with ethyl acetate/60°-80° petroleum ether 1:1. The product was a crystalline material (0.048 g; 49%), which could be recrystallised from ethyl acetate/60°-80° petroleum ether; m.p. 122°-124°. $\nu_{max}$ ($CHCl_3$) 2950, 1770 and 1720 $cm^{-1}$; $\lambda_{max}$ (EtOH) 273 nm (ε4800); δ ppm ($CDCl_3$) 7.36 (5H, br. s, phenyl) 6.59 (1H, t, J 2½ Hz, C3-H), 5.28 and 5.30 (2H, inside signals of ABq, —$CH_2$—Ph), 4.35 (1H, dt, J 6½ and 9 Hz, C5-H), 3.83 (1H, ddd, J 18, 9 and 2½ Hz, C4-H), 3.59 (1H, d J 6½ Hz, C6-H), 2.68(1H, ddd, J 18, 9 and 2½ Hz, C4-H), 1.74 (1H, br. s, —OH), 1.30 and 1.54 (6H, two singlets, C-$CH_3$'s). ($M^+$ at m/e 301. 1315 $C_{17}H_{19}NO_4$ requires 301.1314. Found: C, 67.7; H, 6.5; N, 4.5%. $C_{17}H_{19}NO_4$ requires; C, 67.8; H, 6.4; N, 4.7%).

(b)

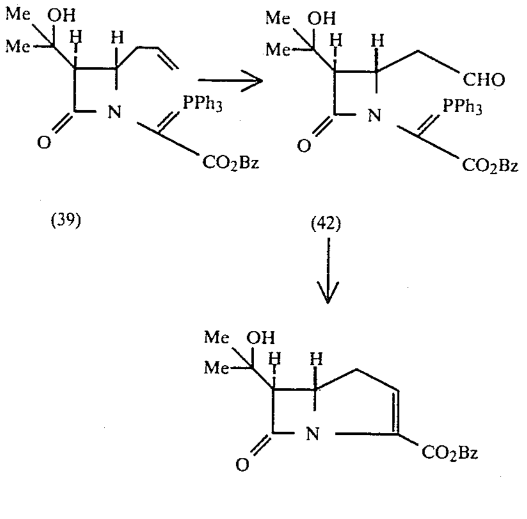

(39) (42) (43)

The trans-isomer of 4-alkyl-1-(1-benzyloxycarbonyl-1-triphenylphosphoranylidenemethyl)-3-(2-hydroxy-2-propyl)azetidin-2-one (39) (0.365 g) was treated as in (a) above. In this case, however, the formation of the bicyclic system (43) was complete after stirring the basified reaction mixture from the ozonolysis for thirty minutes. The required product (0.048 g; 25%) was obtained after chromatography; $\nu_{max}$ ($CHCl_3$) 2950, 1780 and 1720 $cm^{-1}$; δ ppm ($CDCl_3$) 7.28 (5H, br, phenyl), 6.36 (1H, t, J 2 Hz, C3-H), 5.20 (2H, s, —$CH_2$Ph), 4.20 (1H, dt J 3 and 8 Hz, C5-H), 3.16 (1H, d J 3 Hz, C6-trans H), 2.95 and 2.65 (2H, two ddd's J 18, 8 and 2 Hz, C4-H's), 1.78 (1H, br. s, —OH), 1.30 and 1.37 (6H, two singlets, C—$CH_3$'s); ($M^+$ at m/e 301.1303. $C_{17}H_{19}NO_4$ requires 301.1314).

(c) The procedure described in section ii (a) was carried out on the mixture of the cis- and trans-isomers of 4-allyl-1-(1-benzyloxycarbonyl-1-triphenylphosphoranylidenemethyl)-3-(2-hydroxy-2-propyl)azetidin-2-one (0.76 g) as obtained in Example 14 (i) After work-up and chromatographic separation, pure cis (0.045 g; 11%) and trans (0.100 g; 25%) isomers of benzyl 6-(2-hydroxy-2-propyl)-7-oxo-1-azabicyclo [3,2,0]hept-2-ene-2-carboxylate were obtained.

(iii) Preparation of 4-allyl azetidin-2-one

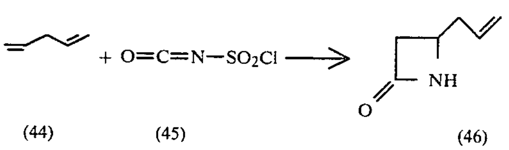

(44) (45) (46)

1,4 Pentadiene (44) (30 g) and chlorosulphenyl isocyanate (45) (35.4 ml) were mixed and allowed to stand at room temperature for 3 days, in a pressure bottle. The thick, dark syrup, obtained was diluted with methylene chloride (500 ml) and added dropwise to a stirred solution of sodium sulphite (66 g) in water (240 ml). The pH was maintained between 6.5 and 7.5 by the addition of 10% aqueous potassium hydroxide (600 ml in total). The lower organic phase was separated and the aqueous phase extracted (×2) with ethyl acetate. The combined organic extracts were dried over magnesium sulphate, filtered, and evaporated to give the crude azetidinone (46) as a red oil (16.05 g). This was sufficiently pure for use in subsequent reactions but could be further purified by distillation b.p. 76°-80°/0.2 mm. $\nu_{max}$ ($CHCl_3$) 3490, 1770 (strong) 1650 (weak) $cm^{-1}$; δ ppm ($CDCl_3$) 2.39 (2H, t, J 6 Hz, $CH_2$) 2.61 (1H, ddd, J 14 Hz, 1.5 Hz, collapsing with $D_2O$ to dd, J 14 Hz, 2 Hz, C3-H), 3.10 (1H, ddd, J 14 Hz, 5 Hz, 2 Hz, collapsing with $D_2O$ to dd, J 14 Hz, 5 Hz, C3-H), 3.55-3.91 (1H, m, C4-H), 4.98-6.21 (3H, complex pattern, CH=$CH_2$), 6.67 (1H, broad s, exch. $D_2O$); (Found: M, 111.0683. $C_6H_9NO$ requires M, 111.0684).

(iv) Preparation of 4-allyl-1-(1-hydroxy-1-benzyloxycarbonylmethyl)azetidin-2-one

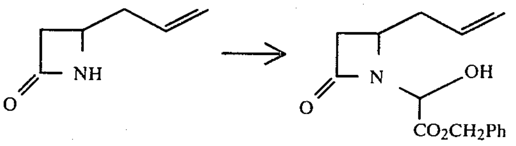

(46) (47)

Benzyl glyoxylate hydrate (6 g) in benzene (120 ml) was refluxed for 0.5 hours in a Dean-Stark apparatus to remove the water. The azetidinone (46) (2.13 g) was added and the reaction mixture refluxed for 4 hours. The solution was cooled, evaporated, and chromatographed on silica gel, eluting with ethyl acetate-petroleum ether mixtures to give a colourless oil (5.6 g) consisting mainly of the isomers of (47) and sufficiently pure for use in subsequent reactions. Rechromatography of a small portion of this oil, eluting with chloroform gave (47) as an oil. $\nu_{max}$($CHCl_3$) 3420, 1750 (strong) 1640 (weak) $cm^{-1}$. δ ppm ($CDCl_3$) 1.90-3.05 [4H, m, including δ 2.53 (1H, dd, J 15 Hz, 2 Hz, C3-H), 2.92 (1H, dd, J 15 Hz, 5 Hz, C3-H), obscuring 2H, $CH_2$], 4.52 (1H, broad, s, exch. $D_2O$, —OH), 4.85-5.90 [6H, m, including δ 5.40 (1H, broad, collapsing with $D_2O$ to singlet, H-C-OH)+complex pattern for $CH_2$Ph and CH=$CH_2$], 7.29 (5H, s).

(v) Preparation of 4-allyl-1-(1-benzloxycarbonyl-1-triphenylphosphoranylidenemethyl)azetidin-2-one

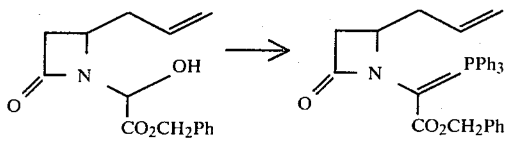

(47) (37)

A stirred solution of the alcohol (47) (6.6 g) in dry tetrahydrofuran (200 ml), under argon, was cooled to −20°, and treated with lutidine (5.13 g) in tetrahydrofuran (10 ml). Thionyl chloride (5.70 g) in tetrahydrofuran (20 ml) was added dropwise. After allowing to reach 0° over 20 minutes, the precipitated solid was filtered off, washed with dry toluene.

The combined filtrate and washings were evaporated to dryness and the residue taken up in dry toluene, filtered and evaporated. The gum obtained was taken up in dioxan (200 ml) and treated with triphenylphosphine (12.6 g) and lutidine (5.53 ml). After stirring under argon at room temperature for 3 hours and standing overnight, the precipitated solid was filtered off. The filtrate was evaporated to dryness. Chromatography on silica gel eluting with ethyl acetate-petroleum ether mixtures, gave the required phosphorane, initially as a foam, which crystallised from ether (5.70 g) m.p. 150°-6°. $\nu_{max}$($CHCl_3$) 1730, 1638, 1610 $cm^{-1}$.

EXAMPLE 15

Benzyl 6-(1-hydroxyethyl)-7-oxo-1-azabicyclo[3,2,0]hept-2-ene-2-carboxylate

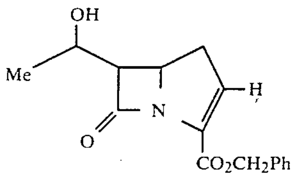

(i) 4-Allyl-1-(1-benzyloxycarbonyl-1-triphenylphosphoranylidenemethyl)-3-(1-hydroxyethyl)azetidin-2-one

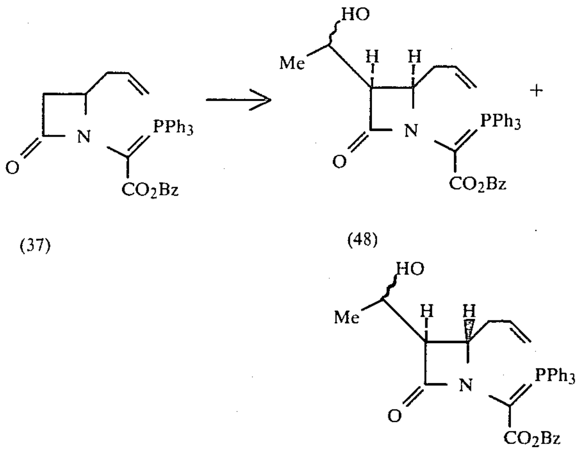

(37) (48) (49)

A solution of N-isopropylcyclohexylamine (0.60 g) in dry tetrahydrofuran (10 ml) was stirred under argon and cooled to −78° C. This was treated with a 2.5 M solution of n-butyl lithium in n-hexane (1.70 ml). After ten minutes, a solution of 4-allyl-1-(1-benzyloxycarbonyl-1-triphenylphosphoranylidenemethyl)azetidin-2-one (37) (1.00 g) in dry tetrahydrofuran (10 ml) was added. Five minutes was allowed for the formation of the C(3) carbanion which was then quenched by the addition of acetaldehyde (0.54 ml). The mixture was stirred under argon for a further ten minutes before it was neutralized with acetic acid (0.56 g). The solvent was evaporated under reduced pressure and the residue chromatographed on silica gel 60 (<230 mesh) eluting with ethyl acetate/cyclohexane mixtures grading from 1:1 to pure ethyl acetate. This gave a mixture of the cis and trans-isomers of 4-allyl-1-(1-benzyloxycarbonyl-1-triphenylphosphoranylidenemethyl)-3-(1-hydroxyethyl) azetidin-2-one (0.71 g; 65%) (48) and (49); $\nu_{max}$ ($CHCl_3$) 3000, 1735 and 1620 $cm^{-1}$.

(ii) Benzyl 6-(1-hydroxyethyl)-7-oxo-1-azabicyclo[3,2,0]hept-2-ene-2-carboxylate

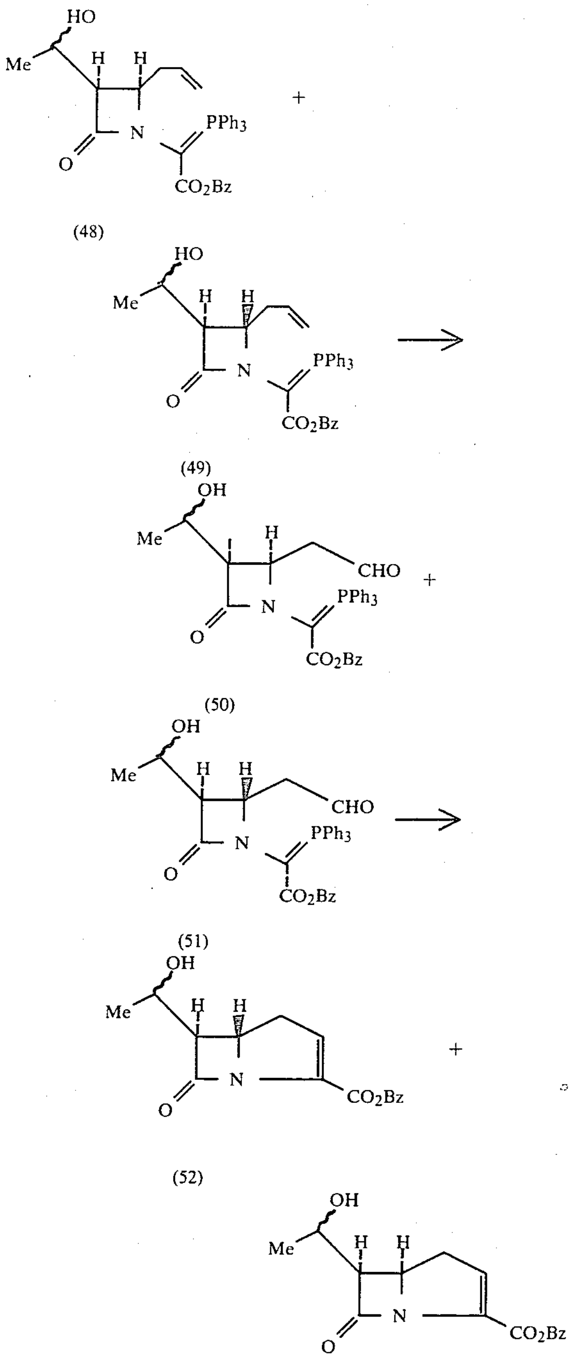

(48) (49) (50) (51) (52) (53)

A mixture of cis and trans-isomers of 4-allyl-1-(1-benzyloxycarbonyl-1-triphenylphosphoranylidenemethyl)-3-(1-hydroxyethyl)azetidin-2-one (0.79 g) as obtained in section (i) was dissolved in redistilled ethyl acetate (70 ml). An excess of trifluoroacetic acid (1.60 g) was added and the mixture cooled to −78° C. Ozone was passed into the reaction mixture until it was pale blue in color. Argon was then bubbled through the solution until all the excess ozone had been removed. A solution of triphenylphosphine (0.37 g) in ethyl acetate was added and argon bubbled through the mixture for a further ten minutes. The reaction flask was then transferred to an ice bath and a saturated aqueous solution of sodium bicarbonate (104 ml) was added to generate the phosphoranes (50) and (51). The mixture was stirred vigourously under argon for thirty minutes. The ethyl acetate layer was separated, washed with brine and dried over sodium sulphate.

The solution was left to stand at room temperature for three days to allow the cyclisation reactions to proceed to completion. The ethyl acetate was then evaporated off under vacuum and the residue chromatographed on silica gel 60 (<230 mesh) (80 g), eluting with ethyl acetate/60°-80° petroleum ether mixtures grading from 3:7 to 7:3. Only two of the four possible diastereoisimers of benzyl 6-(1-hydroxyethyl)-7-oxo-1-azabicyclo[3,2,0]hept-2-ene-2-carboxylate could be isolated from the reaction mixture; these were one cis and one trans-isomer about the $\beta$-lactam ring. The pure cis-isomer (53) 0.030 g; 7.4%) was a crystalline material which could be recrystallised from ethyl acetate/60°-80° petroleum ether; m.p. 94°-99° C. $\nu_{max}$ ($CHCl_3$) 3000, 1775, 1725 and 1615 $cm^{-1}$; $\delta$ ppm ($(CD_3)_2CO$) 7.22-7.40 (5H, m, phenyl), 6.46 (1H, t J 2½ Hz, C3-H), 5.17 (2H, s, $-CH_2$-Ph), 4.25 (1H, ddd J 10, 8 and 6 Hz, —C5-H) overlapping with 3.94-4.23 (1H, m, side-chain —CH), 3.51 (1H, dd J 6 and 6 Hz, C6-H), 3.25 (1H, ddd J 18, 8 and 2½ Hz, C4-H), 2.63 (1H, ddd J 18, 10 and 2½ Hz, C4-H), 1.25 (3H, d J 6 Hz, $-CH_3$) (M+ at m/e 287.1150. $C_{16}H_{17}NO_4$ requires 287.1157).

The pure trans-isomer (52) (0.07 g; 17.4%) had $\nu_{max}$ ($CHCl_3$) 3000, 1780, 1725 and 1610 $cm^{-1}$; $\delta$ ppm ($(CD_3)_2CO$) 7.2-7.5 (5H, m, phenyl), 6.36 (1H, t, J 2½ Hz, C3-H), 5.17 (2H, s, $-CH_2$-Ph), 4.20 (1H, dd J 9 and 3 Hz, C5-H) overlapping with 3.94-4.23 (1H, m, side-chain —CH), 3.31 (1H, dd J 3½ and 3 Hz, C6-H), 2.96 (1H, s, —OH), 2.77 (2H, dd J 9 and 2½ Hz, C4-H's), 1.25 (3H, d J 6 Hz, $-CH_3$) (M+ at m/e 287.1156. $C_{16}H_{17}NO_4$ requires 287.1157).

EXAMPLE 16

Benzyl 3-ethylsulphinyl-7-oxo-1-azabicyclo[3.2.0]hept-2-ene-2-carboxylate

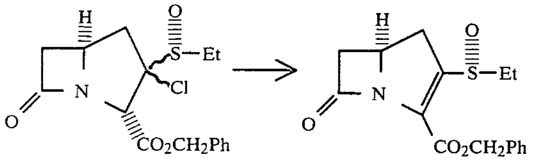

(54) (55)

A suspension of benzyl 3-chloro-3-ethylsulphinyl-7-oxo-1-azabicyclo[3.2.0]heptane-2-carboxylate (54) (0.020 g) in ethylacetate (2 ml) was stirred at room temperature under argon and treated with 1,5-diazabicyclo[5.4.0]undec-5-ene (0.009 g). After a period of 15 minutes the reaction mixture was washed with brine and dried over sodium sulphate. It was concentrated to give a single diastereoisomer of benzyl 3-ethylsulphinyl-7-oxo-1-azabicyclo[3.2.0]hept-2-ene-2-carboxylate (55) (0.017 g) as a gum; νmax ($CHCl_3$) 2980, 1795 and 1730 $cm^{-1}$; $\tau$($d_6$-acetone) 2.5-2.8 (5H, m, phenyl), 4.78 (2H, s, benzyl $CH_2$), 5.71 (1H, tdd J9,5 and 3 Hz, C5-H), 6.49 (1H, dd J17 and 5Hz, C6-H), 6.82 (2H, d J 9 Hz, C4-$H_2$), 6.84 (1H, dd J17 and 3 Hz, C6-H), 7.13 and 7.15 (2H, 2q J7½Hz, $SCH_2$) and 8.80 (3H, t J7½ Hz, $CH_3$).

EXAMPLE 17

Benzyl 3-ethylsulphinyl-7-oxo-1-azabicyclo[3.2.0]hept-2-ene-2-carboxylate

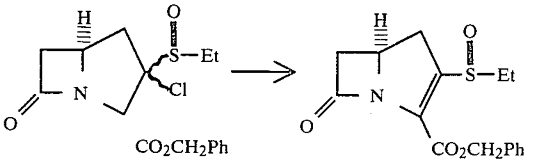

(56) (57)

Benzyl 3-chloro-3-ethylsulphinyl-7-oxo-1-azabicyclo[3.2.0]heptane-2$\beta$-carboxylate (56) (0.037 g) was dissolved in ethylacetate (2 ml) and treated with 1,5-diazabicyclo[5.4.0]undec-5-ene (0.016 g). The mixture was stirred for ½ hour at room temperature and the ethyl acetate solution was then washed with brine and dried over sodium sulphate. It was concentrated and the residue crystallized from ethyl acetate/petrol to give a single diastereoisomer of benzyl 3-ethylsulphinyl-7-oxo-1-azabicyclo[3.2.0]hept-2-ene-2-carboxylate (57) (0.020 g), which was different to that obtained in example 16. The product had m.p. 121°-126° (decomp.); νmax ($CHCl_3$) 2970, 1790, 1720 $cm^{-1}$; $\lambda_{max}$ (ethanol) 307 nm ($\epsilon$5,900); $\tau$($CDCl_3$) 2.66 (5H, s, phenyl), 4.74 (2H, s, benzyl $CH_2$), 5.64 (1H, dddd J10, 8, 5½ and 3½ Hz, C5-H), 6.41 (1H, dd J18 and 10 Hz, C4-H), 6.43 (1H, dd J17 and 5½ Hz, C6-H), 6.94 (1H, dd J17 and 3½ Hz, C6-H) 7.06 (1H, dd J18 and 8 Hz, C4-H), 7.07 and 7.09 (2H, 2q J 7½ Hz, $SCH_2$) and 8.70 (3H, t J 7½ Hz, $CH_3$).

EXAMPLE 18 p-Nitrobenzyl 3-ethylsulphinyl-1-azabicyclo[3.2.0]hept-2-ene-2-carboxylate

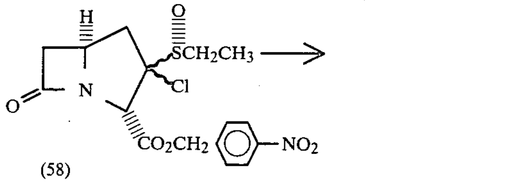

(58)

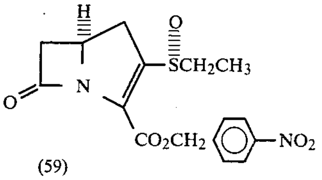

(59)

A stirred solution of the chlorosulphoxide (58) (147 mg) in ethyl acetate (30 ml) was treated with 1,5-diazabicyclo[5.4.0]undec-5-ene (56 mg), added in 1 portion. After 10 minutes the cloudy reaction mixture was washed with water then brine, dried over magnesium sulphate, filtered and the filtrate evaporated to a gum. Trituration of this gum with ether gave a single isomer of the sulphoxide (59) as a white solid (114 mg). This was obtained as white crystals (ex ethyl acetate/60°-80° petroleum ether) m.p. 111°-2° (dec); λmax (EtOH) 268 nm (ε, 12,200), ca 310 nm (inflexion (ε, 6,500); νmax ($CHCl_3$) 1790 (strong), 1718 (weak), 1522, 1350, 1322 $cm^{-1}$; δ($CDCl_3$) 1.36 (3H, t, J7 Hz, $CH_3$), 2.92 (2H,q, J7.5 Hz, $CH_2CH_3$), 3.09 (1H, dd, J16.5 and 2.5 Hz, C6-H), 3.21 (2H, d, J8 Hz, C4-H), 3.56 (1H, dd, J16.5 and 5.5 Hz, C6-H), 4.11-4.45 (1H, m, C3-H), 5.22 and 5.42 (2H, ABq, J14 Hz, benzyl $CH_2$), 7.57 (2H, d, J8 Hz, Ar), 8.16 (2H, d, J8 Hz, Ar). (Found: C, 52.45; H, 4.60; N, 7.75. $C_{16}H_{16}N_2O_6S$ requires C, 52.75; H, 4.40; N, 7.69%).

EXAMPLE 19 p-Nitrobenzyl 3-ethylsulphinyl-1-azabicyclo[3.2.0]hept-2-ene-2-carboxylate

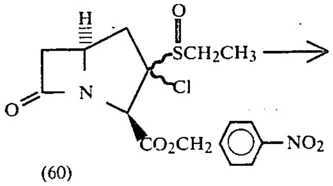

(60)

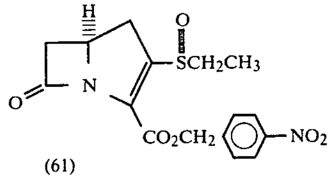

(61)

Treatment of the chlorosulphoxide (60) (77 mg) in ethyl acetate (20 ml), with 1,5-diazabicyclo[5.4.0]undec-5-ene (29.5 mg), as in Example 18, gave after work-up a single isomer of the sulphoxide (61) as an off-white solid (48.8 mg). This product was the other isomer to that obtained in Example (18), and after recrystallisation from ethyl acetate/60°-80° petroleum ether was obtained as white crystals m.p. 110°-113.5°; λmax (EtOH) 269 nm (ε, 11,300), ca 310 nm (inflexion ε, 6,500); νmax ($CHCl_3$) 1795, 1720 (weak, broad), 1525, 1350, 1320 $cm^{-1}$; δ($CDCl_3$) 1.35 (3H, t, J7.5 Hz, $CH_3$), 2.93 (2H, q, J7.5 Hz, $CH_2CH_3$), 3.03 (1H, dd, J16 and 2.5 Hz, C6-H), 3.07 (1H, dd, J19 and 7.5 Hz, CH-H), 3.57 (1H, dd, J16.5 and 5.5 Hz, C6-H), 3.59 (1H, dd, J19 and 9.5 Hz, C4-H), 4.20-4.53 (1H, m, C3-H), 5.21 and 5.45 (2H, ABq, J14 Hz, benzyl $CH_2$), 7.55 (2H, d, J8 Hz, Ar), 8.17 (2H, d, J8 Hz, Ar). (Found C, 52.49; H, 4.43; N, 7.63. $C_{16}H_{16}N_2O_6S$ requires C, 52.75; H, 4.40; N, 7.69%)

EXAMPLE 20

Benzyl 3-(2-acetamidoethylsulphinyl)-7-oxo-1-azabicyclo[3.2.0]hept-2-ene-2-carboxylate

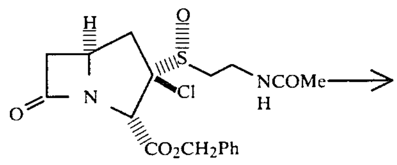

(62)

-continued

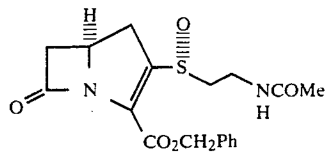

(63)

A solution of benzyl 3-(2-acetamidoethylsulphinyl)-3-chloro-7-oxo-1-azabicyclo[3.2.0]heptane-2-carboxylate (62) (0.010 g) in ethyl acetate (1 ml) was treated with 1,5-diazabicyclo[5.4.0]undec-5-ene (0.0037 g) under an argon atmosphere. It was stirred at room temperature for 15 minutes and then washed with brine and dried over sodium sulphate. The solution was concentrated to give benzyl 3-(2-acetamidoethylsulphinyl)-7-oxo-1-azabicyclo[3.2.0]hept-2-ene-2-carboxylate (63) (0.007 g) as a colourless gum; $\nu_{max}$ ($CHCl_3$) 3400, 2980, 2920, 1795, 1920, 1670, 1600 and 1515 $cm^{-1}$; $\lambda_{max}$ (ethanol) 305 nm; τ ($CDCl_3$) 2.5-2.8 (5H, m, phenyl), 4.76 (2H, s, benzyl $CH_2$), 5.6-5.9 (1H, m, C5-H), 6.3-7.3 (8H, m, C4-$H_2$, C6-$H_2$, $NCH_2CH_2S$) and 8.14 (3H, s, $COCH_3$).

EXAMPLE 21

Benzyl 3-acetamidophenylsulphinyl-7-oxo-1-azabicyclo[3.2.0-]hept-2-ene-2-carboxylate

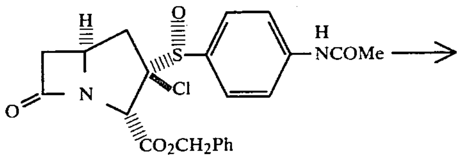

(64)

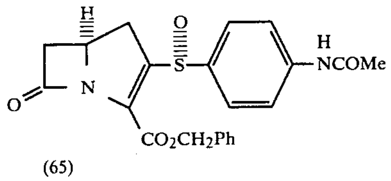

(65)

A solution of benzyl 3-p-acetamidophenylsulphinyl-3-chloro-7-oxo-1-azabicyclo[3.2.0]heptane-2α-carboxylate (64) (0.020 g) in ethyl acetate (2 ml) was stirred under argon at room temperature and treated with 1,5-diazabicyclo[5.4.0]undec-5-ene (0.007 g). After 30 minutes the solution was washed with brine and dried over sodium sulphate. Concentration of the solution gave benzyl 3-p-acetamidophenylsulphinyl-7-oxo-1-azabicyclo[3.2.0]hept-2-ene-2-carboxylate (65) (0.012 g) as a gum; $\nu_{max}$ ($CHCl_3$) 3460, 3000, 1795, 1725, 1705, 1590 and 1505 $cm^{-1}$; $\lambda_{max}$ (ethanol) 297 and 259 nm; τ($CDCl_3$) 2.3-2.7 (10H, m, phenyls and NH), 4.65 (2H, s, benzyl $CH_2$), 5.7-6.1 (1H, m, C5-H), 6.50 (1H, dd J17 and 5½ Hz, C6-H), 6.76 (1H, dd J18 and 9 Hz, C4-H), 6.94 (1H, dd J17 and 3 Hz, C6-H) 7.20 (1H, dd, J18 and 10 Hz, C4-H) and 7.81(3H, s, $COCH_3$).

EXAMPLE 22

Benzyl 3-p-acetamidophenylsulphinyl-7-oxo-1-azabicyclo[3.2.0]hept-2-ene-2-carboxylate

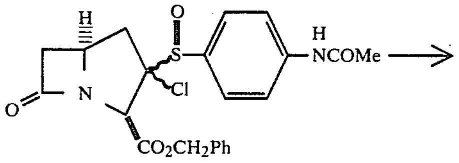

(66)

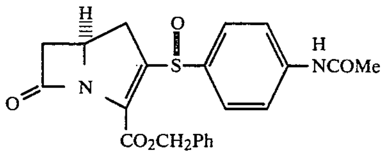

(67)

Benzyl 3-p-acetamidophenylsulphinyl-3-chloro-7-oxo-1-azabicyclo[3.2.0]heptane-2β-carboxylate (66) (0.020 g) was suspended in ethyl acetate (2 ml). It was treated with 1,5-diazabicyclo[5.4.0]undec-5-ene (0.007 g) and stirred at room temperature under argon for 30 mins. The ethyl acetate solution was then washed with brine and dried over sodium sulphate. Evaporation of the solvent gave benzyl 3-p-acetamidophenylsulphinyl-7-oxo-1-azabicyclo[3,2,0]hept-2-ene-2-carboxylate (67) (0.010 g) as a gum; $\nu_{max}$($CHCl_3$) 3460, 3320, 3000, 1795, 1730, 1705, 1590 and 1510 $cm^{-1}$; $\lambda_{max}$(ethanol) 298 sh and 262 nm; τ($CDCl_3$) 2.03 (1H, brs, NH), 2.2–2.8 (9H, m, phenyls), 4.65 (2H, s, benzyl $CH_2$), 5.5–6.0 (1H, m, C5-H), 6.52 (1H, dd J 18 and 9 Hz, C4-H), 6.56 (1H, dd J 17 and 5½ Hz, C6-H), 7.14 (1H, dd J 17 and 3 Hz, C6-H), 7.47 (1H, dd J 18 and 8 Hz, C4-H) and 7.83 (3H, s, $COCH_3$).

EXAMPLE 23

Benzyl 6-(3-methoxycarbonylprop-2-en-1-yl)-7-oxo-3-phenylsulphnyl-1-azabicyclo [3.2.0]hept-2-ene-2-carboxylate

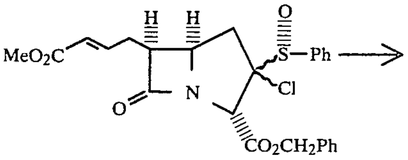

(68)

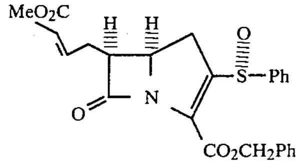

(69)

Benzyl 3-chloro-6-(3-methoxycarbonylprop-2-en-1-yl)-7-oxo-3-phenylsulphinyl-1-azabicyclo[3.2.0]heptane-2-carboxylate (68) (0.015 g) was stirred in ethyl acetate (2 ml) at room temperature under argon and treated with 1,5-diazabicyclo[5,4,0]undec-5-ene (0.005 g). After a period of 15 mins. the reaction mixture was washed with brine and dried over sodium sulphate. Removal of the solvent gave a single diastereoisomer of benzyl 6-(3-methoxycarbonylprop-2-ene-1-yl)-7-oxo-3-phenylsulphinyl-1-azabicyclo[3.2.0]-hept-2-ene-2-carboxylate (69)(0.013 g) as a gum; $\nu_{max}$ ($CHCl_3$) 2980, 1795, 1730, 1720, 1660 and 1045 $cm^{-1}$; τ($d_6$-acetone) 2.3–2.8 (10H, m, phenyls), 3.12 (1H, dt J 16 and 6 Hz, $CH_2$—C<u>H</u>=), 4.12 (1H, dt J 16 and 1 Hz, =C<u>H</u>—CO), 4.68 (2H, s, benzyl $CH_2$), 5.72 (1H, ddd J 10, 9 and 6 Hz, C5-H), 5.9–6.3 (1H, m, C6-H), 6.39 (3H, s, $OCH_3$), 6.81 (1H, dd J 18 and 9 Hz, C4-H), 7.25 (1H, dd J 18 and 10 Hz, C4-H) and 6.9–7.4 (2H, m, C<u>H</u>$_2$-CH=).

EXAMPLE 24

Benzyl 6-(3-methoxy carbonyl prop-2-en-1-yl)-7-oxo-3-phenylsulphinyl-1-azabicyclo [3.2.0]hept-2-ene-2-carboxylate

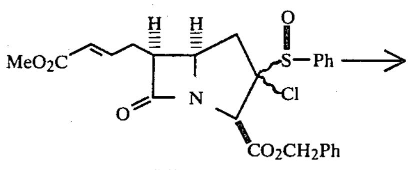

(70)

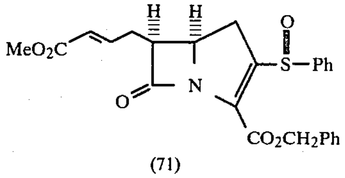

(71)

A solution of benzyl 3-chloro-6-(3-methoxycarbonyl-prop-2-en-1-yl)-7-oxo-3-phenylsulphinyl-1-azabicyclo[3.2.0]heptane-2β-carboxylate (70) (0.020 g) in ethyl acetate (2 ml) was stirred under argon and treated with 1,5-diazabicyclo[5.4.0]undec-5-ene (0.006 g). After a period of 15 mins. the reaction mixture was washed with brine and then dried over sodium sulphate. It was concentrated to a gum which was substantially pure benzyl 6-(3-methoxycarbonylprop-2-en-1-yl)-7-oxo-3-phenylsulphinyl-1-azabicyclo[3.2.0]hept-2-ene-2-carboxylate (71) (0.015 g); $\nu_{max}$ ($CHCl_3$) 2980, 1795, 1720 and 1660 $cm^{-1}$; τ($d_6$-acetone) 2.2–2.8 (10H, m, phenyls), 3.29 (1H, dt J 16 and 6 Hz, $CH_2$—C<u>H</u>=), 4.35 (1H, dt J 16 and 1 Hz, =CH—CO), 4.64 (2H, s, benzyl $CH_2$), 5.46 (1H, ddd J 10, 8 and 6 Hz, C5-H), 5.9–6.3 (1H, m, C6-H), 6.39 (3H, s, $OCH_3$), 6.77 (1H, dd J 18 and 10 Hz, C4-H), 7.47 (1H, dd J 18 and 8 Hz, C4-H) and 7.4–7.8 (2H, m, $CH_2$—C<u>H</u>=).

EXAMPLE 25 p-Bromophenacyl 3-ethylsulphinyl-6-(3-methoxycarbonyl prop-2-en-1-yl)-7-oxo-1-azabicyclo[3.2.0]hept-2-ene-2-carboxylate

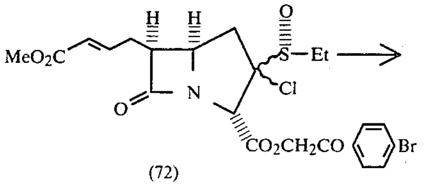

(72)

-continued

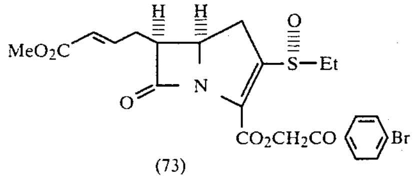

(73)

(i) Dehydrohalogenation with 1,5-diazabicyclo[5,4,0]undec-5-ene

The α-chlorosulphoxide (72) (0.030 g) in dry ethyl acetate (2 ml) was treated with 1,5-diazabicyclo[5,4,-0]undec-5-ene (0.0085 g) (1 equiv.) at 0° in an atmosphere of argon. An immediate precipitate of DBU. HCl was observed. Tlc analysis indicated that the reaction was complete within 5 minutes. The reaction mixture was washed with saturated aqueous sodium chloride solution and dried ($Na_2SO_4$). Recovery gave a $\Delta^2$-sulphoxide (73; of single chirality at sulphur) as a gum (0.023 g) (ca 95% purity; hplc analysis) which could not be induced to crystallise, $\nu_{max}$($CHCl_3$) 1790, 1725, 1710, 1660, 1630, 1590 $cm^{-1}$; $\lambda_{max}$(EtOH) 305 nm (ε=2,900), 290 infl. (3,600), 258 (18,000); δ($d_6$-acetone) 1.28 (3H, t, J 8 Hz), 1.65 br (2H, C4-$H_2$), 2.3–3.3 (m), 3.15 (2H, q, J 8 Hz), 3.63 (3H, s), 3.97 (1H, m, $W_{\frac{1}{2}}$ 13 Hz, C6-H), 4.53 (1H, m, $W_{\frac{1}{2}}$ 13 Hz, C5-H), 5.60 (2H, s), 5.93 br (1H, d, J 15 Hz), 6.92 (1H, dt, J 15, 6 Hz), 7.68 and 7.90 (4H, AA'BB', J 8 Hz).

(ii) Thermal dehydrohalogenation (solid phase)

On heating the α-chlorosulphoxide (72) (0.005 g) in vacuo at 80° for 1 day, the crystals were observed to collapse to a gum. T.l.c analysis of the material [development with ethyl acetate-light petroleum (7:3)] showed the presence of the Δ-2-sulphoxide (73), together with unchanged α-chlorosulphoxide (ca 3:2 ratio). Continued heating in vacuo over NaOH pellets effected complete conversion to the product, which was identified by its i.r. spectrum (identical with that of material prepared).

(iii) Dehydrohalogenation with sodium thiophenoxide

The α-chlorosulphoxide (72) (0.010 g) in dimethylformamide (0.2 ml) was treated with sodium thiophenoxide (0.0025 g) (1 equiv.) at 0° in an atmosphere of argon. After 30 mins. complete conversion to the Δ-2 sulphoxide (73) was observed (t.l.c. analysis), and the product shown (i.r. spectrum) to be identical with material previously prepared.

EXAMPLE 26 p-Bromophenacyl 3-ethylsulphinyl-6-(3-methoxycarbonylprop-2-en-1-yl)-7-oxo-1-azabicyclo[3,2,0]hept-2-ene-2-carboxylate

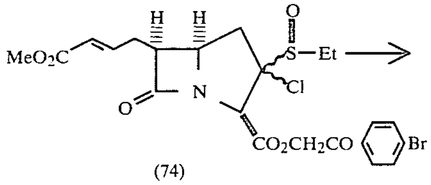

(74)

-continued

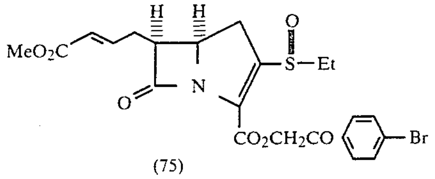

(75)

The C2β-substituted α-chlorosulphoxide (material from example 44) (0.065 g) in ethyl acetate (5 ml) was treated with 1,5-diazabicyclo[5,4,0]undec-5-ene at 0° for 5 mins. Recovery in ethyl acetate as previously described (example 25) gave a Δ-2 unsaturated sulphoxide (75) (0.060 g) as a gum; $\nu_{max}$($CCl_4$) 1795, 1730, 1720sh, 1660, 1590 $cm^{-1}$. This was less stable than the sulphoxide epimer (73) described in Example 25, and was shown to be different to it (h.p.l.c. analysis).

EXAMPLE 27 p-Bromophenacyl 3-ethylsulphinyl-6-(3-methoxycarbonylprop-2-en-1-yl)-7-oxo-1-azabicyclo[3,2,0]hept-2-ene-2-carboxylate

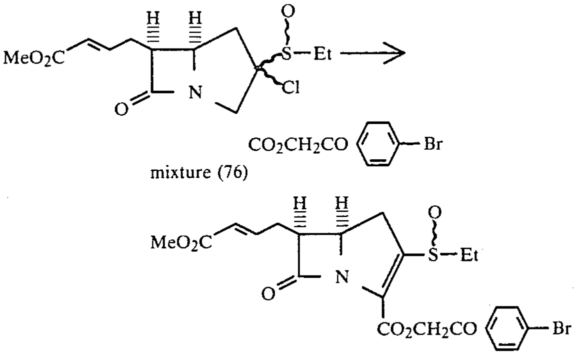

mixture (76)

(73) and (75)

The mixture of R and S sulphoxide epimers of the α-chlorosulphoxide (76) obtained in Example 45 (0.026 g) in ethyl acetate (2 ml), was treated with 1,5-diazabicyclo[5,4,0]undec-5-ene (0.007 g) (1 equiv.) in the usual manner (0°, 15 min). Recovery in ethyl acetate as previously described (Example 25) gave a mixture of R and S sulphoxide epimers of the Δ-2 sulphoxide (73) and (75) as a gum (0.022 g) which foamed in vacuo, $\nu_{max}$($CHCl_3$) 1780, 1720sh, 1705, 1660, 1610 and 1585 $cm^{-1}$; $\lambda_{max}$(EtOH) 307, 260 nm; δ ($d_6$ acetone) 1.24 br (3H, t, J 8 Hz), 1.62 br (2H), 2.3–3.4 (5H, m), 3.60 (3H, s), ca 3.9 (1H, m, C6-H), ca 4.4 (1H, m, C5-H), 5.50 and 5.56 (together 2H, centres of AB quartets for the sulphoxide epimers), 5.87 br (1H, d, J 15 Hz), 6.86 (1H, dt, J 15 and 6 Hz), 7.63 br and 7.85 br (4H, AA' BB', J 9 Hz).

EXAMPLE 28

Phthalidyl 3-ethylsulphinyl-6-(3-methoxycarbonyl prop-2-en-1-yl)-7-oxo-1-azabicyclo[3.2.0]hept-2-ene-2-carboxylate

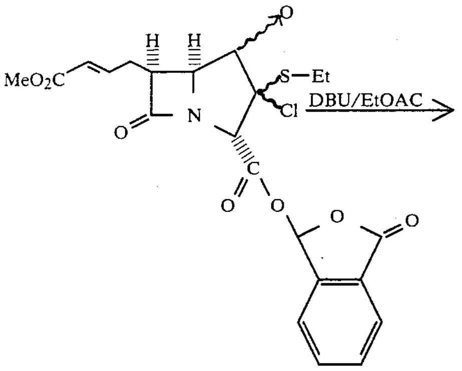

(77)
Isomer A

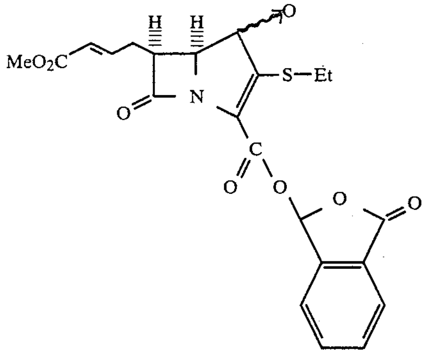

(78)

The major α-chlorosulphoxide (77; Isomer A) (Example 46) (0.026 g) in ethyl acetate, was treated with DBU (0.008 g) (1 equiv) at 0° in the manner previously described. Recovery in ethyl acetate afforded the $\Delta^2$-phthalide ester (78) (0.023 g) $\nu_{max}$($CHCl_3$) 1790, 1770sh, 1740sh, 1725, 1660 1620, 1045, 980 $cm^{-1}$; $\lambda_{max}$ (EtOH) 308 nm ($\epsilon$=2510), 281 (2700), 274 (2640), 225 infl. (17, 000), δ ($d_6$ acetone) 1.15 (3H, t, J 8 Hz), 1.65 br (ca 2H, C4-$H_2$), 2.3-3.3 (2H, m), 3.25 (q, J 8 Hz, —SO—C$\underline{H}_2$$CH_3$) 4.49 (1H, m, $W_{\frac{1}{2}}$ 13 Hz, C6-H), 5.90 (1H, m, $W_{\frac{1}{2}}$ 13 Hz, C5-H), 6.88 (1H, dt, J 15, 6 Hz), 7.52 (1H, s), 7.80 br (4H, m).

EXAMPLE 29

Benzyl 6-benzyl-3-ethylsulphinyl-7-oxo-1-azabicyclo[3.2.0-]hept-2-ene-2-carboxylate

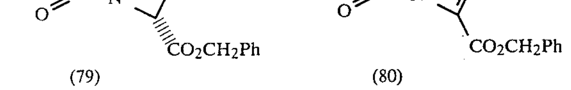

(79) (80)

A solution of benzyl 6-benzyl-3-chloro-3-ethylsulphinyl-7-oxo-1-azabicyclo[3.2.0]heptane-2-carboxylate (79) (0.020 g) in ethyl acetate (2 ml) was treated with 1,5-diazabicyclo[5.4.0]undec-5-ene (0.0069 g). It was stirred for 15 mins. at room temperature and then the solution was washed with brine and dried over sodium sulphate. Concentration of the solution gave benzyl 6-benzyl-3-ethylsulphinyl-7-oxo-1-azabicyclo[3.2.0-]hept-2-ene-2-carboxylate (80) (0.016 g) as a colourless gum; $\nu_{max}$($CHCl_3$) 2990, 1790, 1725 and 1590 $cm^{-1}$; $\lambda_{max}$ (ethanol) 308 nm; τ($CDCl_3$) 2.5-2.9 (10H, m, phenyls), 4.66 and 4.82 (2H, ABq J 12 Hz, $OCH_2$), 5.99 (1H, ddd J 10, 8 and 3 Hz, C5-H), 6.39 (1H, ddd J 9 6 and 3 Hz, C6-H), 6.6-7.2 (4H, m, C4-$H_2$ and C8-$H_2$), 7.20 (2H, q J 7½ Hz, $SCH_2$) and 8.76 (3H, t J 7½ Hz, $CH_3$); ($M^+$ at m/e 409.1333 $C_{23}H_{23}NO_4S$ requires 409.1348).

EXAMPLE 30

Benzyl trans-6-(1-hydroxyethyl)-7-oxo-3-phenylsulphinyl-1-azabicyclo[3.2.0]hept-2-ene-2-carboxylate

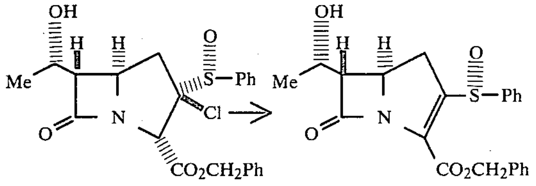

(81) (82)

A suspension of benzyl 3-chloro-trans-6-(1-hydroxyethyl)-7-oxo-3-phenylsulphinyl-1-azabicyclo[3.2.0]heptane-2-carboxylate (81) (0.031 g) in ethyl acetate (3 ml) was stirred at room temperature under argon and treated with 1,5-diazabicyclo[5.4.0]undec-5-ene (0.0106 g). After a period of 30 mins. the solution was washed with brine and dried over sodium sulphate. It was concentrated to a gum which was then crystallised from ethyl acetate/60°-80° petroleum ether to give benzyl trans-6-(1-hydroxyethyl)-7-oxo-3-phenylsulphinyl-1-azabicyclo[3.2.0]hept-2-ene-2-carboxylate (82) (0.015 g); m.p. 104°-109°; $\nu_{max}$($CHCl_3$) 3420, 2980, 1790, 1730, 1625 and 1590 $cm^{-1}$; $\lambda_{max}$ (ethanol) 302 nm; τ($CDCl_3$) 2.3-2.8 (10H, m, phenyls), 4.55 and 4.72 (2H, ABq J 12 Hz, benzyl $CH_2$), 5.7-6.1 (2H, m, C5-H and C8-H), 6.61 (1H, dd J 4 and 2 Hz, C6-H), 6.74 (1H, dd J 19 and 8 Hz, C4-H), 7.27 (1H, dd J 19 and 11 Hz, C4-H), 8.20 (1H, br, OH) and 8.68 (3H, d J 6 Hz, $CH_3$); ($M^+$-$H_2O$ at m/e 393.1058. $C_{22}H_{21}NO_5S$-$H_2O$ requires 393.1032).

EXAMPLE 31

Benzyl 3-ethylsulphinyl-trans-6-(2-hydroxy-2-propyl)-7-oxo-1-azabicyclo[3.2.0]hept-2-ene-2-carboxylate

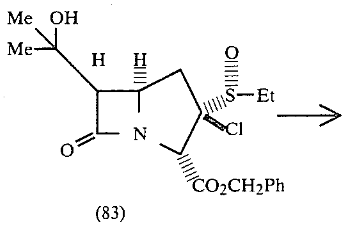

(83)

-continued

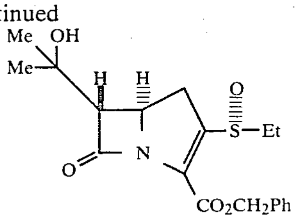

(84)

A solution of benzyl 3-chloro-3-ethylsulphinyl-trans-6-(2-hydroxy-2-propyl)-7-oxo-1-azabicyclo[3.2.0]heptane-2α-carboxylate (83) (0.030 g) in ethyl acetate (2 ml) was stirred under argon at room temperature and treated with 1,5-diazabicyclo[5,4,0]undec-5-ene (0.011 g). After 30 mins. the product was washed with brine and dried over sodium sulphate. The ethyl acetate solution was concentrated to a gum which was crystallized from chloroform/60°-80° petroleum ether to give benzyl 3-ethylsulphinyl-trans-6-(2-hydroxy-2-propyl)-7-oxo-1-azabicyclo[3.2.0]hept-2-ene-2-carboxylate (84) (0.017 g); m.p. 146°-9° dec; $\nu_{max}$($CHCl_3$) 3400, 2970, 1790, 1720 and 1595 $cm^{-1}$; $\lambda_{max}$ (ethanol) 308 nm; $\tau$($CDCl_3$) 2.69 (5H, s, phenyl), 4.68 and 4.86 (2H, ABq J 12 Hz, benzyl $CH_2$), 5.72 (1H, td J 9 and 3 Hz, C5-H), 6.66 (1H, d J 3 Hz, C6-H), 6.82 (2H, d J 9 Hz, C4-$H_2$), 7.15 (2H, q J 7 Hz slightly split, $SCH_2$), 7.85 (1H, brs, OH), 8.59 (3H, s, $CH_3$), 8.70 (3H, s, $CH_3$) and 8.73 (3H, t J 7 Hz, $CH_3$ of SEt); (Found; C, 60.1; H, 6.3; N, 3.6%. $C_{19}H_{23}NO_5S$ requires C, 60.5; H, 6.1 and N, 3.7%).

EXAMPLE 32

Benzyl 3-ethylsulphinyl-trans-6-(2-hydroxy-2-propyl)-7-oxo-1-aza-bicyclo[3.2.0]hept-2-ene-2-carboxylate

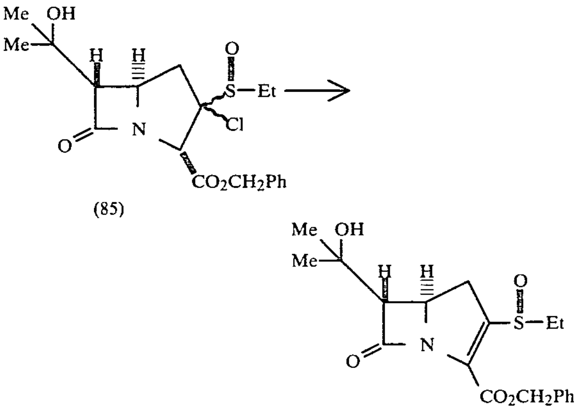

(85) (86)

A solution of benzyl 3-chloro-3-ethylsulphinyl-trans-6-(2-hydroxy-2-propyl)-7-oxo-1-azabicyclo[3.2.0]heptane-2β-carboxylate (85) (0.015 g) in ethyl acetate (2 ml) was stirred under argon at room temperature and treated with 1,5-diazabicyclo[5,4,0]undec-5-ene (0.0055 g). After 30 mins. the reaction mixture was washed with brine and dried over sodium sulphate. It was concentrated to a gum which was crystallized from ethyl acetate/60°-80° petroleum ether to give benzyl 3-ethylsulphinyl-trans-6-(2-hydroxy-2-propyl)-7-oxo-1-azabicyclo[3.2.0]hept-2-ene-2-carboxylate (86) (0.008 g); m.p. 128°-129°; $\nu_{max}$($CHCl_3$) 3400, 2980, 1790, 1725 and 1600 $cm^{-1}$; $\tau$($CDCl_3$) 2.70 (5H, s, phenyl), 4.79 (2H, s, benzyl $CH_2$), 5.66 (1H, ddd J 10, 8 and 3 Hz, C5-H), 6.48 (1H, dd J 19 and 10 Hz, C4-H), 6.71 (1H, d J 3 Hz, C6-H), 7.05 (1H, dd J 19 and 8 Hz, C4-H), 7.14 and 7.16 (2H, 2q J 7 Hz, centres of non-equivalent $SCH_2$), 7.47 (1H, brs, OH), 8.63 and 8.71 (6H, 2s, $C(CH_3)_2$) and 8.76 (3H, t J 7 Hz, $CH_3$ of SEt): (Found; C, 60.5; H, 6.2; N, 3.9%. $C_{19}H_{23}NO_5S$ requires C, 60.5; H, 6.1 and N, 3.7%).

EXAMPLE 33

Benzyl 3-ethylsulphinyl-cis-6-(2-hydroxy-2-propyl)-7-oxo-1-azabicyclo[3.2.0]hept-2-ene-2-carboxylate

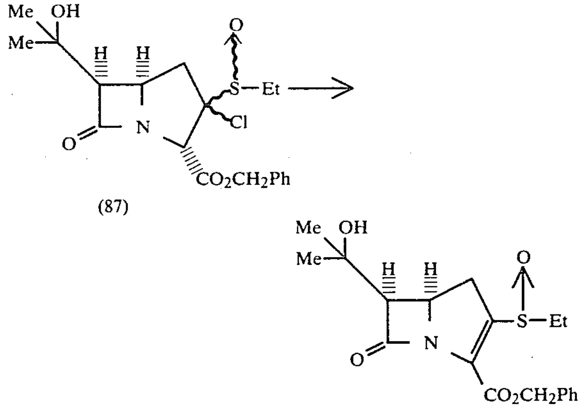

(87) (88)

A solution of benzyl 3-chloro-3-ethylsulphinyl-cis-6-(2-hydroxy-2-propyl)-7-oxo-1-azabicyclo[3.2.0]heptane-2-carboxylate (87) (0.013 g) in ethyl acetate (1 ml) was stirred under argon at room temperature and treated with 1,5-diazabicyclo[5.4.0]undec-5-ene (0.0048 g). After a period of 30 mins, further ethyl acetate (4 ml) was added and the solution washed with brine. The ethyl acetate solution was dried over sodium sulphate and then concentrated to give benzyl 3-ethylsulphinyl-cis-6-(2-hydroxy-2-propyl)-7-oxo-1-azabicyclo[3.2.0-]hept-2-ene-2-carboxylate (88) (0.011 g) as a gum; $\nu_{max}$ ($CHCl_3$) 3400, 2980, 1780 and 1730 $cm^{-1}$; $\lambda_{max}$(EtOH) 305 nm.

EXAMPLE 34

Benzyl 3-chloro-3-ethylsulphinyl-7-oxo-1-azabicyclo[3.2.0-]heptane-2α-carboxylate

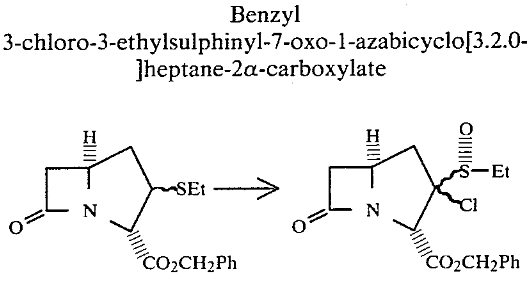

(14) and (15) (54)

A solution of the C3-diastereoisomers of benzyl 3-ethylthio-7-oxo-1-azabicyclo[3.2.0]heptane-2α-carboxylate (14) and (15) (0.038 g) in chloroform (4 ml) was stirred in an ice bath under argon. It was treated with water (0.003 g), pyridine (0.030 g) and iodobenzene dichloride (0.069 g) and stirred for 4 hours. The product was concentrated and then chromatographed on silica gel 60 (<230 mesh) eluting with ethyl acetate/60°-80° petroleum ether. This gave a mixture of two diastereoisomers which when crystallised from chloroform/60°-80° petroleum ether gave the pure major isomer of benzyl 3-chloro-3-ethylsulphinyl-7-oxo-1-azabicyclo[3.2.0]heptane-2α-carboxylate (54) (0.024 g); m.p. 123°-125°; $\nu_{max}(CHCl_3)$ 2980, 1780 and 1740 $cm^{-1}$; $\tau(CDCl_3)$ 2.70 (5H, s, phenyl), 4.88 (2H, s, benzyl $CH_2$), 4.97 (1H, s, C2-H), 5.6-5.9 (1H, m, C5-H), 6.52 (1H, dd J 16 and 5 Hz, C6-H), 6.79 (1H, dd, J 16 and 3 Hz, C6-H), 6.86 (2H, q J 7½ Hz, $SCH_2$), 6.90 (1H, dd J 15 and 7 Hz, C4-H), 7.61 (1H, dd J 15 and 2 Hz, C4-H) and 8.64 (3H, t J 7½ Hz, $CH_3$); (Found; C, 53.9; H, 5.0; N, 3.7%. $C_{16}H_{18}ClNO_4S$ requires C 54.0; H, 5.1; N, 3.9%).

EXAMPLE 35

Benzyl 3-chloro-3-ethylsulphinyl-7-oxo-1-azabicyclo[3.2.0-]heptane-2β-carboxylate

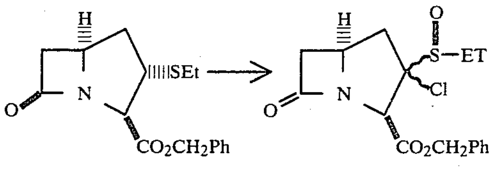

(16) (56)

A solution of benzyl 3α-ethylthio-7-oxo-1-azabicyclo[3.2.0]heptane-2β-carboxylate (16) (0.050 g) in methylene chloride (5 ml) was stirred in an ice bath under argon and treated with water (1 drop), pyridine (0.040 g) and iodobenzene dichloride (0.091 g). The ice-bath was removed and the reaction mixture stirred at room temperature for 3 hours. The solution was then concentrated and chromatographed on silica gel 60 (<230 mesh) eluting with ethyl acetate/60°-80° petroleum ether 7:3 to give benzyl 3-chloro-3-ethylsulphinyl-7-oxo-1-azabicyclo[3.2.0]heptane-2β-carboxylate (56) (0.037 g) as a gum; $\tau(CDCl_3)$ 2.61 (5H, s, phenyl), 4.75 (2H, s, benzyl $CH_2$), 5.55 (1H, s, C2-H), 5.6-5.9 (1H, m, C5-H), 6.5-8.0 (6H, m, C4-$H_2$, C6-$H_2$, $SCH_2$) and 8.64 (3H, t J 7 Hz, $CH_3$). This material was unstable and had to be progressed immediately as shown in example 17.

EXAMPLE 36 p-Nitrobenzyl 3-chloro-3-ethylsulphinyl-7-oxo-1-azabicyclo[3.2.0-]heptane-2α-carboxylate

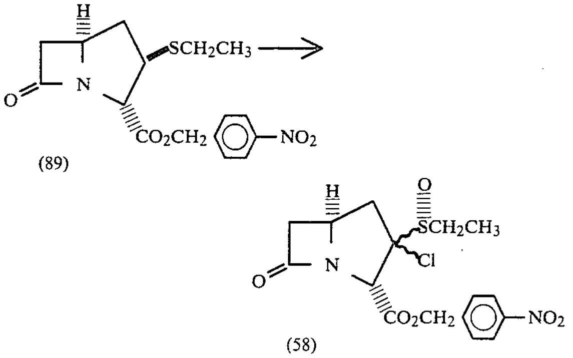

(89) (58)

p-Nitrobenzyl 3β-ethylthio-7-oxo-1-azabicyclo[3.2.0-]heptane-2α-carboxylate (89) (215 mg) was dissolved in chloroform (20 ml) and treated with pyridine (194 mg) and water (8 drops). The stirred mixture was cooled in a bath at −20° and treated with iodobenzene dichloride (506 mg). The reaction vessel was transferred to an ice-bath. After stirring at 0° for 45 mins. the clear solution obtained was dried over magnesium sulphate, filtered concentrated by evaporation, and chromatographed on silica gel (<230 mesh), eluting with 50-60% ethyl acetate in 60°-80° petroleum ether to give a single chlorosulphoxide isomer (58) as a white solid (147 mg). Crystallisation from ethyl acetate/60°-80° petroleum ether gave white needles m.p. 104°-8°; $\nu_{max}(CHCl_3)$ 1780, 1730, 1522, 1350 $cm^{-1}$; $\delta(CDCl_3)$ 1.37 (3H, t, J 7.5 Hz, $CH_3$), 2.41 (1H, dd, J 14 and 2 Hz, C4-H), 2.97 (1H partially obscurred dd, J 14 and 7 Hz, C4-H), 3.10 (2H, q, J 7.5 Hz, $\underline{CH_2}CH_3$), 3.23 (1H, dd, J16 and 3 Hz, C6-H), 3.50 (1H, dd, J 16 and 5.5 Hz, C6-H), 4.15-4.40 (1H, m, C5-H), 5.06 (1H, s, C2-H), 5.20 (2H, s, benzyl $CH_2$), 7.50 (2H, d, J 8 Hz, Ar), 8.15 (2H, d, J 8 Hz, Ar). (Found: C, 48.20; H, 4.26; N, 7.01. $C_{16}H_{17}N_2ClO_6S$ requires C, 47.94; H, 4.24; N, 6.99%).

EXAMPLE 37 p-Nitrobenzyl 3-chloro-3-ethylsulphinyl-7-oxo-1-azabicyclo[3.2.0-]heptane-2β-carboxylate

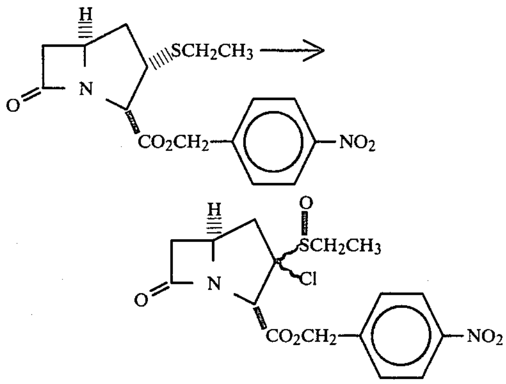

(90) (60)

p-Nitrobenzyl 3α-ethylthio-7-oxo-1-azabicyclo[3.2.0-]heptane-2β-carboxylate (90) (71.4 mg) in dry chloroform (7.1 ml) was treated with pyridine (63.2 mg) and water (2 drops). The stirred mixture was cooled in a bath at −20° and iodobenzene dichloride (165 mg) added. After allowing the reaction mixture to reach 0° over 30 minutes the yellow solution obtained was stood at 0° for 30 minutes then in the freezer for 30 minutes. Water was removed from the reaction mixture by filtration through phase-sep paper and the filtrate was reduced in volume by evaporation then chromatographed on silica gel (<230 mesh). Elution with 50-70% ethyl acetate in 60°-80° petroleum ether gave a single isomer of the chlorosulphoxide (60) as an unstable gum, (59.5 mg); $\nu_{max}(CHCl_3)$ 1775, 1742, 1522, 1345 $cm^{-1}$; $\delta(CDCl_3)$ 1.37 (3H, m, $CH_3$), 2.20-3.37 [6H including δ2.31 (1H, dd, J 13 and 5 Hz, C4-H), 2.59 (1H, dd, J 13 and 9 Hz, C4-H), 2.90 (1H, dd, J 16 and 2 Hz, C6-H), 3.24 (1H, dd, J 16 and 5 Hz, C6-H) obscurring (2H, m, unsymmetrical $\underline{CH_2}CH_3$)], 4.12-4.38 (1H, m, C3-H), 4.43 (1H, s, C2-H), 5.29 (2H, s, benzyl $CH_2$), 7.53 (2H, d, J 8 Hz, Ar), 8.05 (2H, d, J 8 Hz, Ar).

EXAMPLE 38

Benzyl 3-(2-acetamidoethylsulphinyl)-3-chloro-7-oxo-1-azabicyclo[3.2.0]heptane-2-carboxylate

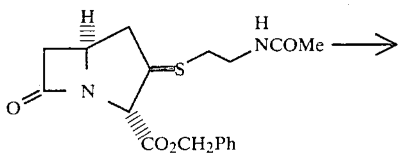

(91)

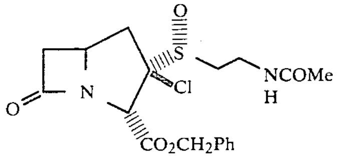

(62)

Benzyl 3-(2-acetamidoethylthio)-7-oxo-1-azabicyclo[3.2.0]heptane-2-carboxylate (91) (0.050 g) was dissolved in chloroform (5 ml) and stirred at 0° under argon. It was treated with water (0.010 g) and pyridine (0.022 g) followed by iodobenzene dichloride (0.038 g). A period of 2 hours was allowed to elapse and the solution was concentrated and the product chromatographed on silica gel 60 (<230 mesh) eluting with chloroform/ethanol 9:1. This gave benzyl 3-(2-acetamidoethylsulphinyl)-3-chloro-7-oxo-1-azabicyclo[3.2.0]heptane-2-carboxylate (62) (0.040 g); m.p. 89°-93°, $\nu_{max}$($CHCl_3$) 3450, 2980, 1780, 1745, 1670 and 1515 $cm^{-1}$; $\tau$($CDCl_3$) 2.70 (5H, s, phenyl), 3.70 (1H, br, NH) 4.88 (2H, s, benzyl $CH_2$) 4.97 (1H, s, C2-H), 5.6-5.9 (1H, m, C5-H), 6.40 (2H, q J 5 Hz, $NCH_2$), 6.6-7.0 (4H, m, $SCH_2$ and C6-$H_2$), 7.05 (1H, dd J 15 and 8 Hz, C4-H), 7.68 (1H, dd J 15 and 2 Hz, C4-H) and 8.07 (3H, s, $COCH_3$); (Found: C, 52.1; H, 5.4; N, 6.9%. $C_{18}H_{21}ClN_2O_5S$ requires C, 52.4; H, 5.1 and N, 6.8%).

EXAMPLE 39

Benzyl 3-p-acetamidophenylsulphinyl-3-chloro-7-oxo-1-azabicyclo[3.2.0]heptane-2α-carboxylate

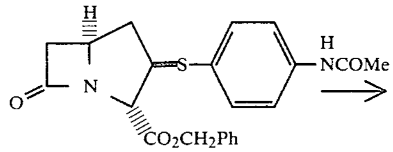

(92)

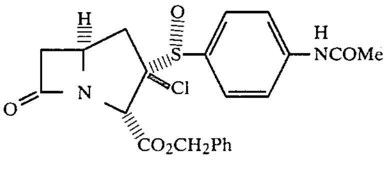

(64)

A solution of benzyl 3-p-acetamidophenylthio-7-oxo-1-azabicyclo[3.2.0]heptane-2α-carboxylate (92) (0.150 g) in chloroform (10 ml) was stirred under argon and treated successively with water (0.007 g), pyridine (0.102 g) and iodobenzene dichloride (0.251 g). After a period of 1 hour at room temperature, the solution was concentrated and then chromatographed on a column of silica gel 60 (<230 mesh) eluting with ethyl acetate. This gave benzyl 3-p-acetamidophenylsulphinyl-3-chloro-7-oxo-1-azabicyclo[3.2.0]heptane-2α-carboxylate (64) (0.120 g) as a colourless foam; $\nu_{max}$($CHCl_3$) 3460, 3340, 3000, 1785, 1745, 1700, 1590 and 1510 $cm^{-1}$; $\tau$($CDCl_3$) 1.52 (1H, brs, NH), 2.2-2.8 (9H, m, phenyls), 4.74 (2H, s, benzyl $CH_2$), 4.96 (1H, s, C2-H), 5.6-5.9 (1H, m, C5-H), 6.62 (1H, dd J 16 and 5 Hz, C6-H), 6.93 (1H, dd J 16 and 2½ Hz, C6-H), 7.16 (1H, dd J 15 and 8 Hz, C4-H), 7.86 (3H, s, $COCH_3$) and 8.22 (1H, d J 15 Hz, C4-H).

EXAMPLE 40

Benzyl 3-p-acetamidophenylsulphinyl-3-chloro-7-oxo-1-azabicyclo[3.2.0]heptane-2β-carboxylate

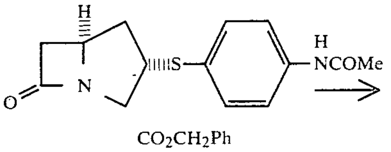

(93)

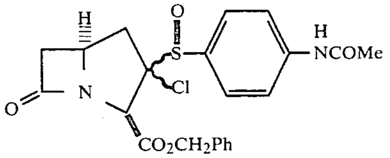

(66)

Benzyl 3-p-acetamidophenylthio-7-oxo-1-azabicyclo[3.2.0]heptane-2β-carboxylate (93) (0.150 g) was stirred in chloroform (10 ml) under an argon atmosphere. It was cooled to 0° and treated with water (0.007 g), pyridine (0.102 g) and iodobenzene dichloride (0.251 g). The cooling bath was removed and the reaction mixture was stirred at room temperature for 2 hours. The resulting solution was concentrated to small bulk and then chromatographed on silica gel 60 (<230 mesh) eluting with ethyl acetate to give benzyl 3-p-acetamidophenyl-sulphinyl-3-chloro-7-oxo-1-azabicyclo[3.2.0]heptane-2β-carboxylate (66) (0.066 g); m.p. 165°-175° dec (chloroform/60°-80° petroleum ether); $\nu_{max}$($CHCl_3$) 3450, 3350, 3000, 1780, 1740, 1700, 1590 and 1510 $cm^{-1}$; $\tau$($CDCl_3$) 2.2-2.8 (10H, m, phenyls and NH), 4.68 (2H, s, benzyl $CH_2$), 5.56 (1H, s, C2-H) 5.7-6.1 (1H, m, C5-H), 6.76 (1H, dd J 16 and 4 Hz, C6-H), 7.08 (1H, dd J 16 and 2½ Hz), 7.50 (1H, dd J 12 and 9 Hz, C4-H), 7.81 (3H, s, $COCH_3$) and 8.28 (1H, dd J 12 and 5 Hz, C4-H); (Found; C, 57.1; H, 4.3; N, 6.3%. $C_{22}H_{21}ClN_2O_5S$ requires C, 57.3; H, 4.6 and N, 6.1%).

EXAMPLE 41

Benzyl 3-chloro-6-(3-methoxycarbonylprop-2-ene-1-yl)-7-oxo-3-phenylsulphinyl-1-azabicyclo[3.2.0]heptane-2α-carboxylate

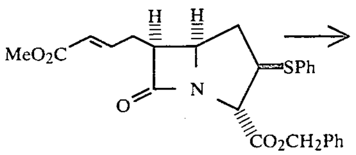

(94)

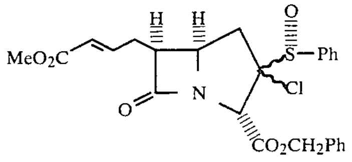

(68)

A solution of benzyl 6-(3-methoxycarbonylprop-2-en-1-yl)-7-oxo-3-phenylthio-1-azabicyclo[3.2.0]heptane-2-carboxylate (94) (0.050 g) in chloroform (3 ml) was stirred at 0° under argon and treated with water (0.002 g), pyridine (0.026 g) and iodobenzene dichloride (0.061 g). After 1 hour the solution was concentrated and then chromatographed on silica gel 60 (<230 mesh) eluting with ethyl acetate/60°-80° petroleum ether 1:1 This produced benzyl 3-chloro-6-(3-methoxycarbonylprop-2-en-1-yl)-7-oxo-3-phenylsulphinyl-1-azabicyclo[3.2.0]heptane-2α-carboxylate (68) (0.024 g); m.p. 144°-146° (ethylacetate/60°-80° petroleum ether); $\nu_{max}(CHCl_3)$ 3000, 2950, 1780, 1725 and 1660 $cm^{-1}$; $\tau(CDCl_3)$ 2.3-2.8 (10H, m, phenyls), 3.24 (1H, dt J 15 and 6 Hz, $CH_2$—C<u>H</u>=), 4.31 (1H, dt J 15 and 1 Hz, =CH—$CO_2$), 4.76 (2H, s, benzyl $CH_2$), 4.99 (1H, s, C2-H), 5.63 (1H, ddd J 9, 5½ and 2½ Hz, C5-H), 6.2-6.5 (1H, m, C6-H), 6.35 (3H, s, $OCH_3$), 7.17 (1H, dd J 15 and 9 Hz, C4-H), 7.3-7.6 (2H, m, C$\underline{H}_2$—CH=) and 8.29 (1H, dd J 15 and 2½ Hz, C4-H); (Found: C, 59.7; H, 4.9; N, 2.7%. $C_{25}H_{24}ClNO_6S$ requires C, 59.8; H, 4.8 and N, 2.8%).

EXAMPLE 42

Benzyl 3-chloro-6-(3-methoxycarbonylprop-2-ene-1-yl)-7-oxo-3-phenylsulphinyl-1-azabicyclo[3.2.0]heptane-2β-carboxylate

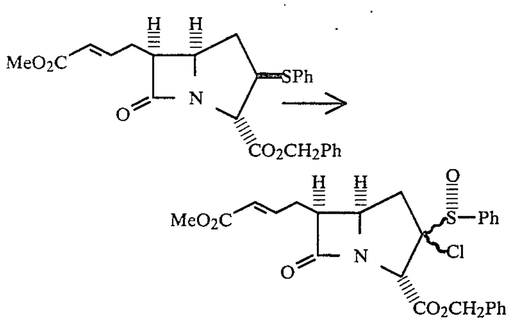
(95)
(70)

Benzyl 6-(3-methoxycarbonylprop-2-ene-1-yl)-7-oxo-3-phenylthio-1-azabicyclo[3.2.0]heptane-2β-carboxylate (95) (0.050 g) was dissolved in chloroform (3 ml) and stirred under argon at 0°. It was then treated with water (0.004 g) and pyridine (0.026 g) followed by iodobenzene dichloride (0.061 g). After a period of three hours, the solution was concentrated and then chromatographed on silica gel 60 (<230 mesh) eluting with ethyl acetate/60°-80° petroleum ether 1:1. This gave the product as a gum which could then be crystallised from chloroform/diethyl ether to give benzyl 3-chloro-6-(3-methoxycarbonylprop-2-ene-1-yl)-7-oxo-3-phenylsulphinyl-1-azabicyclo[3.2.0]heptane-2β-carboxylate (70) (0.038 g) as a chloroform solvate; m.p. 150°-160° (dec); $\nu_{max}(CHCl_3)$ 2980, 1780, 1730 and 1660 $cm^{-1}$; $\tau(CDCl_3)$ 2.3-2.8 (11H, m, phenyls and $CHCl_3$), 3.21 (1H, dt J 16 and 6 Hz, $CH_2$—C<u>H</u>=), 4.27 (1H, dt J 16 and 1 Hz, CH=C<u>H</u>—CO), 4.72 (2H, s, benzyl $CH_2$), 5.59 (1H, s, C2-H), 5.84 (1H, dt J 10 and 5 Hz, C5-H), 6.32 (3H, s, $OCH_3$), 6.57 (1H, dt J 11 and 5 Hz, C6-H), 7.3-7.6 (2H, m, C$\underline{H}_2$—CH=), 7.48 (1H, dd J 12 and 10 Hz, C4-H) and 8.46 (1H, dd J 12 and 5 Hz, C4-H); (Found: C, 50.1; H, 4.3; N, 2.2%. $C_{25}H_{24}ClNO_6S,CHCl_3$ requires C, 50.3; H, 4.1 and N, 2.3%).

EXAMPLE 43 p-Bromophenacyl 3-chloro-3-ethylsulphinyl-6-(3-methoxycarbonylprop-2-en-1-yl)-7-oxo-1-azabicyclo[3.2.0]heptane-2α-carboxylate

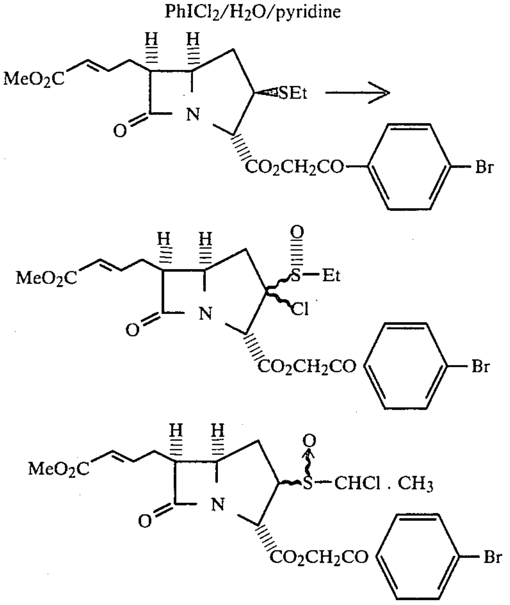

(25)
(72)
(96)

The p-bromophenacyl-3β-sulphide-2α-carboxylate (25) (0.192 g) in anhydrous chloroform (10 ml) was treated successively with water (0.007 g), pyridine (0.090 g) and iodobenzene dichloride (0.207 g) at 0° in an atmosphere of argon for 30 min. Evaporation and chromatography of the residue on Kieselgel (elution with ethyl acetate/light petroleum, 7:3) afforded a leading component as a gum (0.019 g), $\nu_{max}(CHCl_3)$ 1780, 1760, 1720 sh, 1710, 1660, 1590 $cm^{-1}$, shown (pmr spectrum) to be a mixture (ca 1:1) of side-chain chlorinated material (96) [δ1.88 (d, J 7 Hz)], together with minor epimers of structure (72). The major component was a single α-chlorosulphoxide (72) which gave microcrystals (ethyl acetate-diethyl ether-light petroleum) (0.143 g) m.p. 107°-8°, (Found: C 47.0; H, 4.3; N, 2.3; S, 5.6%. $C_{22}H_{23}BrClNO_7S$ requires C, 47.1; H, 4.1; N, 2.5; S, 5.7%); $\nu_{max}(CHCl_3)$ 1780, 1765sh, 1725sh, 1710, 1660, 1590 $cm^{-1}$; $\delta(CDCl_3)$ 1.40 (3H, t, J 7 Hz), 2.34 (1H, dd, J 16, 3 Hz, C4β-H), 2.6-3.4 (5H, m), 3.70 (3H, s), 3.80 (1H, m, $W_{1/2}$ 9 Hz, C6-H), 5.55 (1H, td, J 6, 3 Hz, C5-H), 5.09 (1H, s, C2β-H), 5.20 and 5.40 (2H, ABq, J 17 Hz) 5.84 (1H, dt, J 15, 1 Hz), 6.90 (1H, dt, J 15, 6 Hz), 7.56 and 7.72 (4H, AA'BB', J 8 Hz); irradiation at the frequency of the methyl protons located the —SO—C$\underline{H}_2$—$CH_3$ resonance at δ 3.08. Similarly, irradiation at the frequency of the C5-proton located the C4 α-proton signal (δ3.21, collapsed to dd, J 16, 3 Hz) and caused a simplification of the signal due to the C6-side chain methylene group centered ca δ2.8).

EXAMPLE 44 p-Bromophenacyl 3-chloro-3-ethylsulphinyl-6-(3-methoxycarbonylprop-2-en-1-yl)-7-oxo-1-azabicyclo[3.2.0]heptane -2β-carboxylate

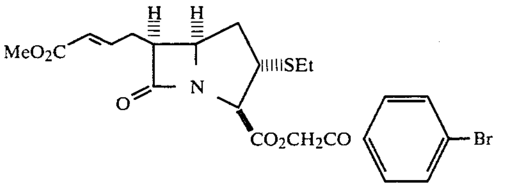
(27)

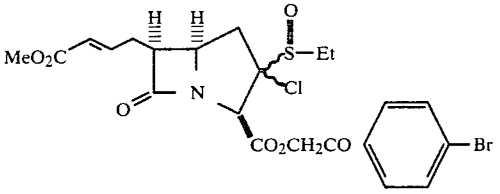
(74)

The p-bromophenacyl 3α-sulphide-2β-carboxylate (27) (0.125 g) in anhydrous chloroform (7 ml) was treated with water (0.005 g) (1 equiv), pyridine (0.060 g) (3 equiv) and iodobenzene dichloride (0.135 g) (2 equiv) in the manner described above (example 43). Recovery and chromatography as before gave a single (hplc analysis) α-chlorosulphoxide isomer (74) as a gum (0.104 g) (Found: C, 46.9; H, 3.9; N, 2.3; S, 6.2%. $C_{22}H_{23}BrClNO_7S$ requires C, 47.1; H, 4.1; N, 2.5; S, 5.7%); $\nu_{max}$ ($CHCl_3$) 1780, 1740sh, 1725, 1720, 1660, 1590 $cm^{-1}$; δ($CDCl_3$) 1.38 (3H, t, J 7 Hz), 2.15 (1H, dd, J 14, 6 Hz, C4α-H), 2.5–3.3 (5H, m, C4β-H, C6-side chain CH, —SC$\underline{H}_2$CH$_3$), ca 3.5 br (1H, m, C6-H), 3.67 (3H, s), 4.34 br (1H, m, C5-H), 4.49 (1H, s, 2α-H), 5.25 and 5.46 (2H, ABq, J 17 Hz), 5.83 br (1H, d, J 15 Hz), 6.87 (1H, dt, J 15, 6 Hz), 7.54 and 7.72 (4H, AA'BB', J 7 Hz).

EXAMPLE 45 p-Bromophenacyl 3-chloro-3-ethylsulphinyl-6-(3-methoxycarbonylprop-2-en-1-yl)-7-oxo-1-azabicyclo[3.2.0]heptane-2α-carboxylate

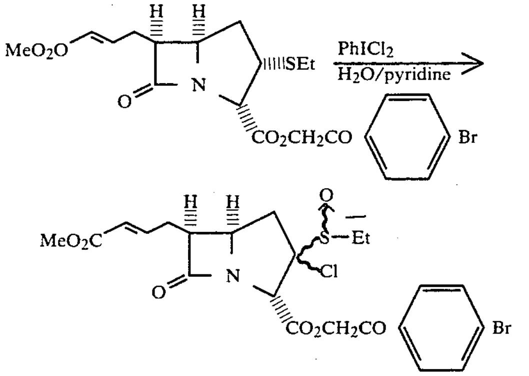

(26)
(76)

Mixture

The p-bromophenacyl 3α-sulphide-2α-carboxylate (26) (0.114 g) in anhydrous chloroform (7 ml) was treated with water (0.005 g) (1 equiv), pyridine (0.056 g) (3 equiv), and iodobenzene dichloride (0.130 g) (2 equiv) as described above (example 43) (30 mins.). Recovery and chromatography as previously described afforded minor components (0.021 g), consisting of isomers of structure (76), together with side chain-chlorinated material (cf structure 96) (nmr spectra). The major product, a single C3-isomer, which proved to be a mixture of R and S sulphoxide epimers (76), was eluted as a gum (0.067 g) which foamed in vacuo and slowly solidified, m.p. 55°–60° (Found; C, 46.9; H, 4.1; N, 2.6; S, 5.3%. $C_{22}H_{23}BrClNO_7S$ requires; C, 47.1; H, 4.1; N, 2.5; S, 5.7%); $\nu_{max}$($CHCl_3$) 1775, 1720sh, 1710, 1660, 1585 $cm^{-1}$; δ($CDCl_3$) 1.39 (3H, t, J 8 Hz), 1.78 (2H, m), 2.33 (1H, dd, J 16, 3 Hz, C4α-H), 2.7 br (2H, m, C6-side chain CH$_2$), 2.9–3.4 (3H, m, C4-H+—SO—C$\underline{H}_2$CH$_3$), 3.67 (3H, s), 3.70 br (1H, C6-H), 4.46 (1H, m, $W_{\frac{1}{2}}$ 13 Hz, C5-H), 5.02** (1H, s, 2β-H), 5.30 br* (2H), 5.85 br(1H, d, J 15 Hz), 7.87 (1H, dt, J 15,6 Hz), 7.53 and 7.69 (4H, AA'BB', J 8 Hz).

* Doubling of the resonances supports a mixture of R+S sulphoxides
** A single resonance indicates that the compound is of a single C3-configuration.

EXAMPLE 46

Phthalidyl 3-chloro-3-ethylsulphinyl-6-(3-methoxycarbonylprop-2-en-1-yl)-7-oxo-1-azabicyclo[3.2.0]heptane-2α-carboxylates

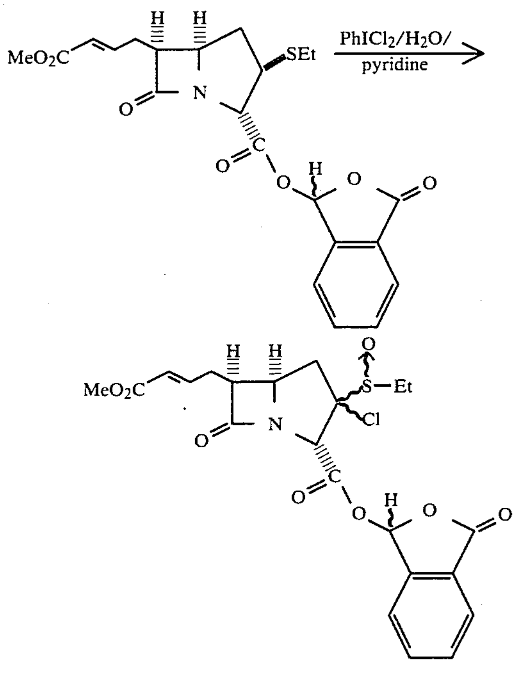

(97)
(77)

Isomers A,B & C.

The phthalidyl 3β-sulphide-2α-carboxylate (97) (0.060 g) in anhydrous chloroform (3 ml) was treated successively with water (0.0025 g) (1 equiv), pyridine (0.032 g) (3 equiv) and iodobenzene dichloride (0.075 g) (2 equiv) at 0° in an atmosphere of argon for 30 min. Recovery in ethyl acetate in the manner previously described (example 43) gave the products, which were shown to be a mixture of 3 components (t.l.c. analysis). Chromatography on Kieselgel (<230 mesh) (4×2.5 cm); (elution with ethyl acetate-light petroleum; 7:3) afforded a pure α-chlorosulphoxide of structure (77) (isomer A) as the major product (0.028 g), $\nu_{max}$($CHCl_3$) 1785, 1775sh, 1720, 1660, 980 $cm^{-1}$; δ($CDCl_3$) 1.49 (3H, t, J 8 Hz), 2.41 (1H, dd, J 16, 2 Hz, C4β-H), 2.6–2.9 (2H, m), 3.05–3.45 (3H, m, —SO.C$\underline{H}_2$$CH_3$+C4α-H), 3.70 (3H, s), 3.73 br (1H, m, C6-H), 4.25 (1H, m, C5-H), 5.05 (1H, s, 2β-H), 5.82 br (1H, d, J 15 Hz), 6.85 (1H, dt, J 15, 6 Hz), 7.27 (1H, s), 7.5–7.9 (4H, m).

Further elution of the column afforded a minor component, Isomer B (0.009 g), $\nu_{max}$($CHCl_3$) 1785, 1775sh, 1720, 1660 and 980 $cm^{-1}$.

Finally, a third isomer of the title compound, Isomer C, was obtained as a crystalline solid (ex chloroform-ethyl acetate-light petroleum) (0.021 g), m.p. 150°–152°; gas evolution, $\nu_{max}$($CHCl_3$) 1790, 1775sh, 1720, 1660 and 980 $cm^{-1}$. (Found: C, 53.4; H, 4.8; N, 2.9. $C_{22}H_{22}NO_8S$ requires C, 53.3; H, 4.5; N, 2.8%).

EXAMPLE 47

Benzyl 6-benzyl-3-chloro-3-ethylsulphinyl-7-oxo-1-azabicyclo[3.2.0]heptane-2-carboxylate (98)

(79)

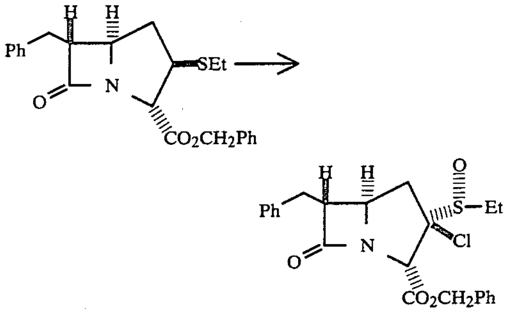

A solution of benzyl 6-benzyl-3-ethylthio-7-oxo-1-azabicyclo[3.2.0]heptane-2-carboxylate (98) (0.047 g) in chloroform (5 ml) was treated with water (0.005 g), pyridine (0.033 g) and iodobenzene dichloride (0.082 g) at 0° under argon. The solution was concentrated after 2 hours and then chromatographed on silica gel 60 (<230 mesh) eluting with ethyl acetate/60°–80° petroleum ether 7:3 to give benzyl 6-benzyl-3-ethylsulphinyl-7-oxo-1-azabicyclo[3.2.0]heptane-2-carboxylate (79) (0.030 g); m.p. 118°–123° (ethyl acetate/60°–80° petroleum ether); $\nu_{max}$($CHCl_3$) 2980, 1775 and 1745 $cm^{-1}$; τ($CDCl_3$) 2.6–2.9 (10H, m, phenyls), 4.89 (2H, s, $OCH_2$) 4.98 (1H, s, C2-H), 5.92 (1H, ddd J 8, 3 and 2 Hz, C5-H), 6.26 (1H, ddd J 9, 6 and 3 Hz, C6-H), 6.6–7.3 (5H, m, C4-H, C8-$H_2$, $SCH_2$), 7.72 (1H, dd J 15 and 2 Hz, C4-H) and 8.68 (3H, t J 7½ Hz, $CH_3$).

EXAMPLE 48

Benzyl 3-chloro-trans-6-(1-hydroxyethyl)-7-oxo-3-phenylsulphinyl-1-azabicyclo[3.2.0]heptane-2-carboxylate

(99) and (100)

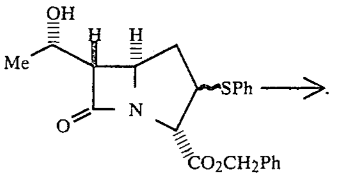

-continued (81).

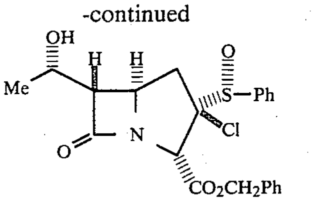

The 2:1 mixture of diastereoisomers of benzyl trans-6-(1-hydroxyethyl)-7-oxo-3-phenylthio-1-azabicyclo[3.2.0]heptane-2α-carboxylate (99) and (100) (0.047 g) was dissolved in chloroform (4 ml) and stirred in an ice bath under argon. It was treated with water (0.005 g), pyridine (0.038 g) and then iodobenzene dichloride (0.097 g). After a period of 2 hours the solution was concentrated and applied to a column of silica gel 60 (<230 mesh). Elution with ethyl acetate/60°–80° petroleum ether 7:3 gave benzyl 3-chloro-trans-6-(1-hydroxyethyl)-7-oxo-3-phenylsulphinyl-1-azabicyclo[3.2.0]heptane-2-carboxylate (81) (0.015 g); m.p. 154°–159° (chloroform/60°–80° petroleum ether); $\nu_{max}$($CHCl_3$) 3480, 2980, 1780, and 1745 $cm^{-1}$; τ($CDCl_3$) 2.3–2.9 (10H, m, phenyls), 4.75 (2H, s, benzyl $CH_2$), 4.95 (1H, s, C2-H), 5.7–6.1 (2H, m, C5-H and C8-H), 6.58 (1H, dd J5 and 3 Hz, C6-H), 7.08 (1H, dd J 15 and 9 Hz, C4-H), 8.13 (1H, brs, OH), 8.23 (1H, brd J 15 Hz, C4-H) and 8.72 (3H, d J 6 Hz, $CH_3$); (Found: C, 58.9; H, 4.7; N, 3.2%. $C_{22}H_{22}ClNO_5S$ requires C, 59.0; H, 5.0 and N, 3.1%).

EXAMPLE 49

Benzyl 3-chloro-3-ethylsulphinyl-6-(2-hydroxy-2-propyl)-7-oxo-1-azabicyclo[3.2.0]heptane-2α-carboxylate (101) and (102)

(83)

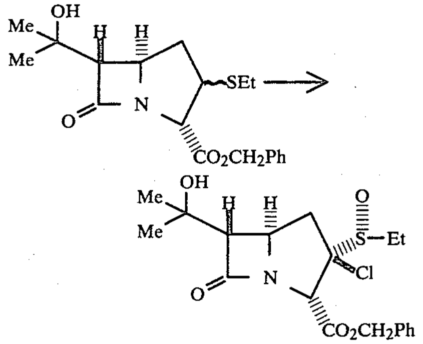

The 3:1 mixture of isomers of benzyl 3-ethylthiotrans-6-(2-hydroxy-2-propyl)-7-oxo-1-azabicyclo[3.2.0]heptane-2α-carboxylate (101) and (102) (0.040 g) was dissolved in chloroform (3 ml) and stirred at 0° under argon. It was treated with water (0.004 g), pyridine (0.026 g) and then iodobenzene dichloride (0.061 g). After a period of 2 hours the solution was concentrated and applied to a column of silica gel 60 (<230 mesh). Elution with ethyl acetate/60°–80° petroleum ether 4:1 gave benzyl 3-chloro-3-ethylsulphinyltrans-6-(2-hydroxy-2-propyl)-7-oxo-1-azabicyclo[3.2.0]heptane-2α-carboxylate (83) (0.031 g) as a gum; $\nu_{max}$($CHCl_3$) 3450, 2980, 1775 and 1750sh $cm^{-1}$; τ($CDCl_3$) 2.71 (5H, s, phenyl), 4.88 (2H, s, benzyl $CH_2$), 4.97 (1H, s, C2-H), 5.73 (1H, ddd J 8, 3 and 1 Hz, C5-H), 6.51 (1H, d J 3 Hz, C6-H), 6.7–7.3 (2H, m, $SCH_2$), 6.92 (1H, dd J 15 and 8 Hz, C4-H), 7.64 (1H, dd J 15 and 1 Hz, C4-H), 7.97 (1H, brs, OH), 8.62 (3H, s, $CH_3$), 8.66 (3H, t J 7 Hz, $CH_3$ of SEt) and 8.69 (3H, s, $CH_3$).

EXAMPLE 50

Benzyl 3-chloro-3-ethylsulphinyl-trans-6-(2-hydroxy-2-propyl)-7-oxo-1-azabicyclo[3.2.0]heptane-2β-carboxylate (103)

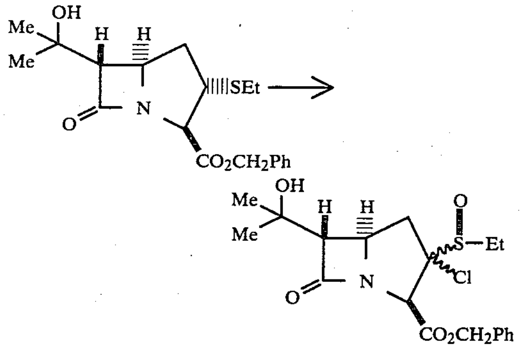

(85)

A solution of benzyl 3-ethylthio-trans-6-(2-hydroxy-2-propyl)-7-oxo-1-azabicyclo[3.2.0]heptane-2β-carboxylate (103) (0.030 g) in chloroform (2 ml) was cooled to 0° under argon and treated with water (0.003 g), pyridine (0.020 g) and iodobenzene dichloride (0.046 g). It was stirred for 2 hours and then concentrated to give a residue which was chromatographed on silica gel 60 (<230 mesh) eluting with ethyl acetate. This gave benzyl 3-chloro-3-ethylsulphinyl-trans-6-(2-hydroxy-2-propyl)-7-oxo-1-azabicyclo[3.2.0]heptane-2β-carboxylate (85) (0.015 g) as a gum; $\nu_{max}(CHCl_3)$ 3450, 2980, 1775 and 1740 $cm^{-1}$; $\tau(CDCl_3)$ 2.69 (5H, s, phenyl), 4.74 and 4.89 (2H, ABq J 12 Hz, benzyl $CH_2$), 5.60 (1H, s, C2-H), 5.76 (1H, ddd J 9, 5 and 2½ Hz, C5-H), 6.82 (1H, d J 2½ Hz, C6-H), 6.7–7.3 (2H, m, $SCH_2$), 7.34 (1H, dd J 13 and 9 Hz, C4-H), 7.71 (1H, dd J 13 and 5 Hz, C4-H), 8.22 (1H, brs, OH), 8.60 (3H, s, $CH_3$), 8.66 (3H, t J 7½ Hz, $CH_3$ of SEt) and 8.70 (3H, s, $CH_3$).

EXAMPLE 51

Benzyl 3-chloro-3-ethylsulphinyl-cis-6-(2-hydroxy-2-propyl)-7-oxo-1-azabicyclo[3.2.0]heptane-2-carboxylate (104)

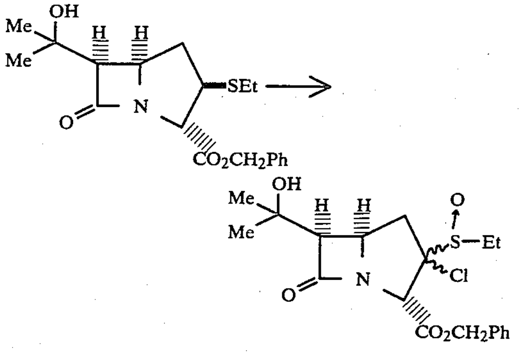

(87)

Benzyl 3-ethylthio-cis-6-(2-hydroxy-2-propyl)-7-oxo-1-azabicyclo[3.2.0]heptane-2-carboxylate (104) (0.040 g) was dissolved in chloroform (3 ml) and stirred in an ice bath under argon. It was treated successively with water (0.004 g), pyridine (0.026 g) and iodobenzene dichloride (0.061 g). After a period of 1 hour the solution was concentrated and applied to a column of silica gel 60 (<230 mesh) and eluted with ethyl acetate/60°-80° petroleum ether 7:3. The second compound to be eluted was benzyl 3-chloro-3-ethylsulphinyl-cis-6-(2-hydroxy-2-propyl)-7-oxo-1-azabicyclo[3.2.0]heptane-2-carboxylate (87) (0.015 g); m.p. 137°–143° dec (ethyl acetate/60°–80° petroleum ether); $\nu_{max}(CHCl_3)$ 3460 and 1770 $cm^{-1}$; $\tau(CDCl_3)$ 2.71 (5H, s, phenyl), 4.85 (2H, s, benzyl $CH_2$), 4.89 (1H, s, C2-H), 5.72 (1H, dt J 8 and 5 Hz, C5-H), 6.01 (1H, dd J 13 and 8 Hz, C4-H), 6.53 (1H, d J 5 Hz, C6-H), 7.14 (2H, q J 7½ Hz, $SCH_2$), 7.55 (1H, dd J 13 and 5 Hz, C4-H), 7.95 (1H, s, OH), 8.56 (3H, s, $CH_3$), 8.70 (3H, t J 7½ Hz, $CH_3$ of SEt) and 8.81 (3H, s, $CH_3$).

EXAMPLE 52 p-Nitrobenzyl 3-ethylthio-7-oxo-1-azabicyclo[3.2.0]heptane-2-carboxylate (105)

(106)

(89)

(107)

(90)

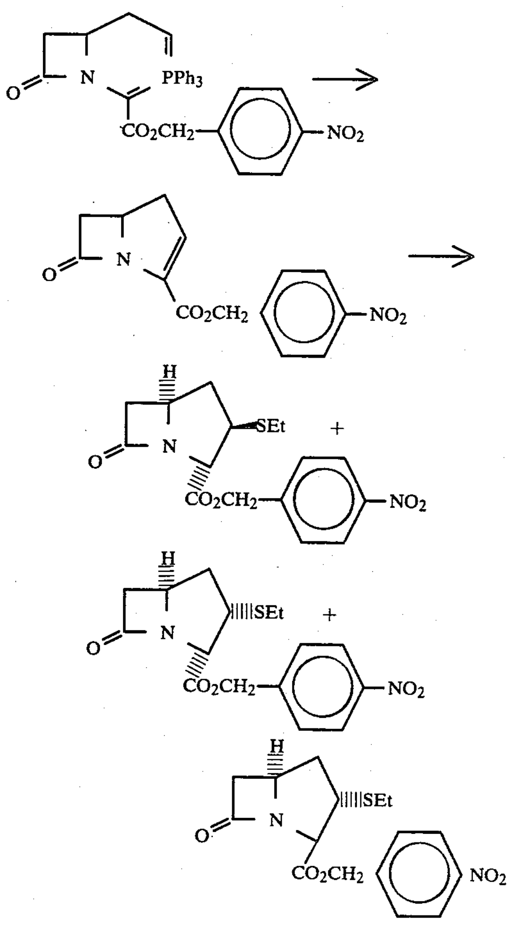

Method(i)—not isolating intermediate (106)

A stirred suspension of the phosphorane (105) (1.066 g) in ethyl acetate (100 ml) under argon at ambient temperature was treated with trifluoroacetic acid (3.08 ml). The clear solution obtained was cooled (−70°) and treated with ozonised oxygen until pale blue. Argon was passed through to remove excess ozone and then a solution of triphenylphosphine (575 mg) in ethyl acetate (10 ml) was added.

After 10 minutes below −50° the reaction vessel was transferred to an ice-bath. When the internal temperature reached −10°, a saturated aqueous solution of sodium bicarbonate (100 ml) was added. After vigorous agitation for 15 minutes below 5°, the organic phase was separated washed with brine, dried over magnesium sulphate, filtered and stood at ambient temperature for 1.5 hrs. The solution, shown by t.l.c. to contain mainly the intermediate bicyclic compound (106) along with triphenylphosphine oxide, was evaporated to dryness and the residue immediately taken up in dry dimethylformamide (5 ml). The stirred solution was treated at ambient temperature with ethanethiol (0.15 ml), followed by powdered potassium carbonate (0.027 g). After 1.5 hours the red reaction mixture was diluted with ethyl acetate (100 ml), washed with water then brine, dried over magnesium sulphate, filtered and evaporated. The crude material was chromatographed on silica gel 60 (<230 mesh) eluting with 60°–80° petroleum ether/ethyl acetate mixtures to give the three isomers (89), (107) and (90).

The first product (89) (0.147 g) was obtained as white crystals from ethyl acetate/60°–80° petroleum ether m.p. 79°–80.5°; $\nu_{max}(CHCl_3)$ 1765, 1755 (shoulder), 1522, 1350 cm$^{-1}$; δ ppm ($CDCl_3$) 1.23 (3H, t, J 7 Hz, $CH_3$), 2.20 (2H, dd, J 8, 6.5 Hz C4-H) 2.56 (2H, q, J 7 Hz, $C\underline{H}_2CH_3$), 2.75 (1H, dd, J 16, 2 Hz, C6-H), 3.38 (1H, dd, J 16, 5 Hz, C6-H), 3.62 (1H, t d, J8, 6.5 Hz, C3-H), 3.96–4.25 (1H, m, C5-H), 4.78 (1H, d, J6.5 Hz, C2-H), 5.25 (2H, s, $C\underline{H}_2$ Ar), 7.51 (2H, d, J7.5 Hz, Ar), 8.17 (2H, d, J 7.5 Hz, Ar). (Found: C, 55.00, H, 5.26, N. 7.81%. $C_{16}H_{18}N_2O_5S$ requires C, 54.86; H, 5.14, N, 8.00%).

The second product (107) (0.084 g) was obtained as a gum; $\nu_{max}(CHCl_3)$ 1760, 1750, 1520, 1325 cm$^{-1}$; δ ppm ($CDCl_3$) 1.21 (3H, t, J7 Hz), 1.63 (1H, ddd, J13, 9, 8 Hz, C4-H), 2.35–2.90 [4H, including: 2.56 (2H, q, J7 Hz, $CH_2C\underline{H}_3$), 2.77 (1H, dd, J16 2 Hz, C6-H) plus 1C4-H] 3.29 (1H, dd, J16, 4.5 Hz, C6-H), 3.55–3.97 (2H, complex pattern, C3 and C5-H), 4.33 (1H, d, J6 Hz, C2-H), 5.24 (2H, s, $CH_2Ar$), 7.47 (2H, d, J8 Hz, Ar), 8.15 (2H, d, J8 Hz, Ar). (Found: M+ at 350.0952. $C_{16}H_{18}N_2O_5S$ requires M+ at 350.0936).

The third product (90) (0.090 g) was obtained as white crystalline plates from ether, which were recrystallized from ethyl acetate/petroleum ether m.p. 97°–8°; $\nu_{max}(CHCl_3)$, 1765, 1745, 1520, 1345 cm$^{-1}$; δ ppm ($CDCl_3$) 1.21 (3H, t, J7 Hz, $CH_3$), 1.91 (1H, ddd, J12, 12, 10 Hz, C4-H), 2.30 (1H, ddd, J12, 6, 6 Hz, C4-H), 2.55 (2H, q, J7 Hz, $C\underline{H}_2CH_3$), 2.79 (1H, dd, J16, 2 Hz, C6-H), 3.11 (1H, dd, J16, 4 Hz, C6-H), 3.50–3.85 (2H, complex pattern, C3-H and C5-H), 4.14 (1H, d, J7 Hz, C2-H), 5.26 (2H, s, $C\underline{H}_2Ar$), 7.52 (2H, d, J8 Hz, Ar), 8.14 (2H, d, J8 Hz, Ar). (Found: C, 54.85; H, 5.34; N, 7.80%. $C_{16}H_{18}N_2O_5S$ requires C, 54.86, H, 5.14; N, 8.00%).

Method (ii) from purified (106)

To a stirred suspension of p-nitrobenzyl 7-oxo-1-azabicyclo[3.2.0]hept-2-ene-2-carboxylate (106) (1.15 g), prepared as in (i) but isolated by chromatograpy, in dry dimethylformamide (10 ml) at ambient temperature was added ethanethiol (0.29 ml), followed by potassium carbonate (0.055 g). The starting material (106) immediately dissolved. After stirring the orange mixture for 30 mins. a further 2 drops of ethanethiol were added. After 10 mins. the reaction mixture was diluted with ethyl acetate (200 ml). Work up and chromatography as in (i) gave (89)(0.681 g), (107)(0.078 g) and (90)(0.362 g).

EXAMPLE 53

Benzyl 3-(2-acetamidoethylthio)-7-oxo-1-azabicyclo[3.2.0]heptane-2-carboxylate

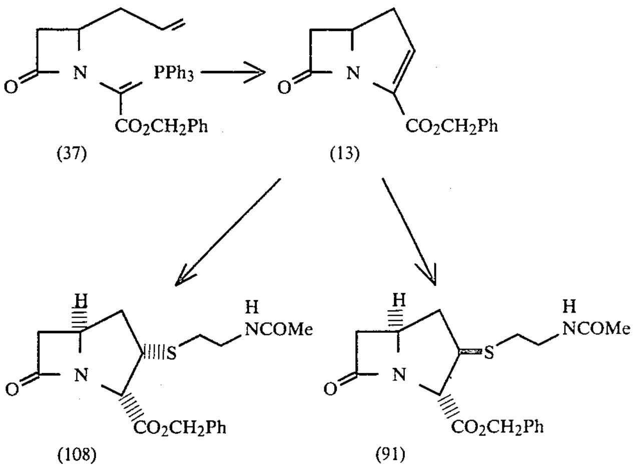

(37) (13) (108) (91)

A solution of 4-allyl-1-(1-benzyloxycarbonyl-1-triphenylphosphoranylidenemethyl)azetidine-2-one (37) (1.00 g) in ethyl acetate (70 ml) was treated with trifluoroacetic acid (3 ml) and then cooled to −78°. Ozone was passed through the solution until it just became blue and the excess of ozone was removed by bubbling argon through. An ethylacetate solution of triphenylphosphine (0.51 g) was then added, and the flask was transferred to an ice bath after 30 mins. The reaction mixture was neutralized by addition of saturated aqueous sodium bicarbonate (90 ml) with vigorous stirring. After 30 mins the organic phase was separated and dried over sodium sulphate. The solvent was then stripped off and the residue dissolved in dry dimethylformamide. This solution was treated with 2-acetamidoethanethiol (0.30 g) and potassium carbonate (0.13 g). It was stirred at room temperature for 1½ hours and then concentrated under high vacuum. The residue was partitioned between ethyl acetate and brine and the ethyl acetate solution was separated, dried over sodium sulphate and then concentrated. The residue was chromatographed on silica gel 60 (<230 mesh) eluting with ethyl acetate grading to ethyl acetate/ethanol 19:1 to give two isomers of benzyl 3-(2-acetamidoethylthio)-7-oxo-1- azabicyclo[3.2.0]heptane-2-carboxylate (108) and (91). The least polar isomer was the 2α, 3α-compound (108) (0.25 g); $\nu_{max}$($CHCl_3$) 3480, 3000, 1765, 1745sh, 1670 and 1520 $cm^{-1}$; τ($CDCl_3$) 2.71 (5H, s, phenyl), 3.78 (1H, br, NH), 4.87 (2H, s, benzyl $CH_2$), 5.66 (1H, d J5 Hz, C2-H), 6.0–6.4 (1H, m, C5-H), 6.6–6.9 (3H, m, $NCH_2$ and C6-H), 7.1–7.6 (5H, m, $SCH_2$, C6-H, C4-H and C3-H), 8.10 (3H, s, $COCH_3$) and 8.41 (1H, dt J13 and 7 Hz, C4-H). The more polar isomer was the 2α,3β-compound (91) (0.055 g); $\nu_{max}$3460, 3000, 1765, 1745sh, 1665 and 1515 $cm^{-1}$; τ($CDCl_3$) 2.71 (5H, s, phenyl), 3.80 (1H, br, NH), 4.86 (2H, s, benzyl $CH_2$), 5.30 (1H, d J7 Hz, C2-H), 5.97 (1H, qd J5 and 2½ Hz, C5-H), 6.43 (1H, broadened q J 8 Hz, C3-H), 6.5–6.8 (3H, m, $NCH_2$ and C6-H), 7.1–7.5 (3H, m, $SCH_2$ and C6-H), 7.84 (2H, dd J8 and 5 Hz, C4-$H_2$) and 8.10 (3H, s, $COCH_3$).

EXAMPLE 54

Preparation of p-nitrobenzyl 3-(2-acetamidoethylthio)-7-oxo-1-azabicyclo[3.2.0]heptane-2-carboxylate brine, dried over magnesium sulphate, filtered and evaporated. Chromatography of the residual gum on silica gel (<230 mesh) (20 g) eluting with ethyl acetate followed by 10% ethanol in ethyl acetate gave the three products (109) (110) and (111).

The first fractions obtained gave a gum (183 mg) shown by n.m.r. to be a mixture of the C-2α isomers (109) and (110) in the ratio 2:1. These compounds could be separated by rechromatography on silica gel eluting with chloroform/ethanol mixtures. The 2α, 3α isomer (109) was obtained as a gum; $\nu_{max}$ ($CHCl_3$) 1768, 1755 (shoulder), 1675, 1522, 1345 $cm^{-1}$; δppm ($CDCl_3$) 1.65(1H, ddd J 13, 8.5 and 7.5 Hz, C4-H), 1.96(3H, s, $CH_3$), 2.50–3.10[4H, including 2.69 and 2.75(2H, 2t's, J6 Hz, side chain $CH_2$), 2.81(1H, dd, J 16 and 2 Hz, C6-H) with a C4-H obscured] 3.28–3.52 (3H, overlapping m's side-chain $CH_2$ and C6-H), 3.70–4.01(2H, overlapping m's C3-H and C5-H), 4.39(1H, d, J 6 Hz, C2-H), 5.29(2H, s, benzyl $CH_2$) 6.12(1H, broad signal, NH), 7.53(2H, d, J8.5 Hz, Ar), 8.21(2H, d, J 8.5 Hz, Ar).

The 2α, 3β isomer (110) was also obtained as a gum;

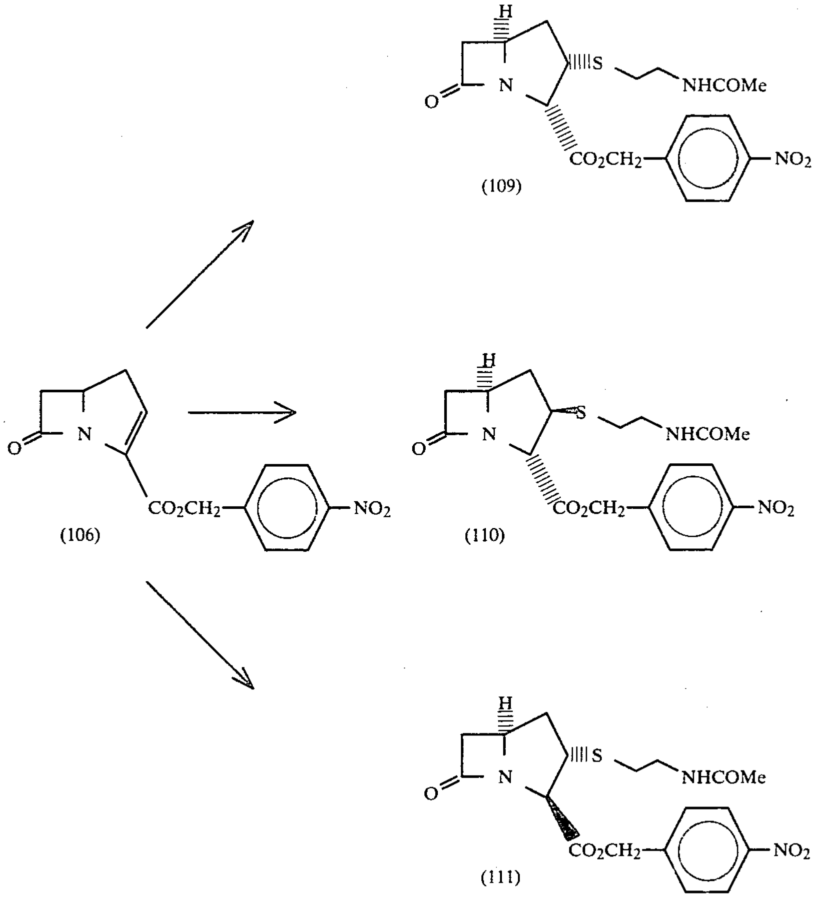

(109) (106) (110) (111)

To p-nitrobenzyl 7-oxo-1-azabicyclo[3.2.0]hept-2-ene-2-carboxylate (106) (284 mg) under argon, was added with stirring 2-acetamidoethanethiol (131 mg) in dry dimethylformamide. A clear yellow solution was obtained to which was added powdered potassium carbonate (7 mg). After stirring at ambient temperature for 45 minutes, to the by now red reaction mixture, was added further thiol (26 mg) and potassium carbonate (7 mg). After a total of 1 hour the reaction solution was reduced in volume by evaporation and was then diluted with ethyl acetate (100 ml) washed with water, then $\nu_{max}$ ($CHCl_3$) 1775, 1758(shoulder), 1678, 1522, 1350 $cm^{-1}$; δ ppm ($CDCl_3$) 1.95(3H, s, $CH_3$), 2.20(2H, dd, J 8.5 and 6.5 Hz, C4-H's), 2.69 and 2.72(2H, 2t's, J 6 Hz, side chain $CH_2$), 2.76(1H, dd, J16 and 2.5 Hz, C6-H), 3.2–3.8[4H, comprising 3.33(2H, t, J 6 Hz, side chain $CH_2$), 3.65(1H, td, J8.5 and 6.5 Hz, C3-H) and an obscured C6-H], 3.93–4.20(1H, m, C5-H), 4.78(1H, d, J 6.5 Hz, C2-H), 5.27(2H, s, benzyl $CH_2$), 6.03(1H, broad signal, NH), 7.54(2H, d, J8.5 Hz, Ar), 8.21(2H, d, J 8.5 Hz, Ar).

The next fractions from the first column, contained a mixture of isomers (109), (110) and (111) [t.l.c. analysis] as a gum (36 mg) and further elution with 10% ethanol in ethyl acetate gave the 2β, 3α-isomer (111) contaminated with more polar material (t.l.c. analysis, 10% ethanol in chloroform), as a gum (71 mg). Rechromatography on silica gel (<230 mesh) eluting with chloroform/ethanol mixtures gave (111) as a gum $\nu_{max}$ ($CHCl_3$) 1770, 1745, 1675, 1522, 1350 $cm^{-1}$; δppm ($CDCl_3$) 1.89(1H, ddd, J 12,12 and 10 Hz, C4-H), 1.96(3H, s, $CH_3$) 2.34(1H, ddd, J12, 6 and 6 Hz, C4-H), 2.69(2H, td, J 6 and 3 Hz, side-chain $CH_2$), 2.77(1H, dd, J 16 and 3 Hz, C6-H), 3.13(1H, dd, J 16 and 4.5 Hz, C6-H), 3.33(2H, t, J 6 Hz, side-chain $CH_2$), 3.60–3.89(2H, overlapping m's C3-H and C5-H) 4.16(1H, d, J7 Hz, C2-H), 5.29(2H, s, benzyl $CH_2$), 6.07(1H, broad signal, NH), 7.57(2H, d, J8.5 Hz, Ar), 8.20(2H, d, J 8.5 Hz, Ar).

EXAMPLE 55

Preparation of p-nitrobenzyl 3-(2-p-nitrobenzyloxycarbonyl-aminoethylthio)-7-oxo-1-azabicyclo[3.2.0]heptane-2-carboxylate

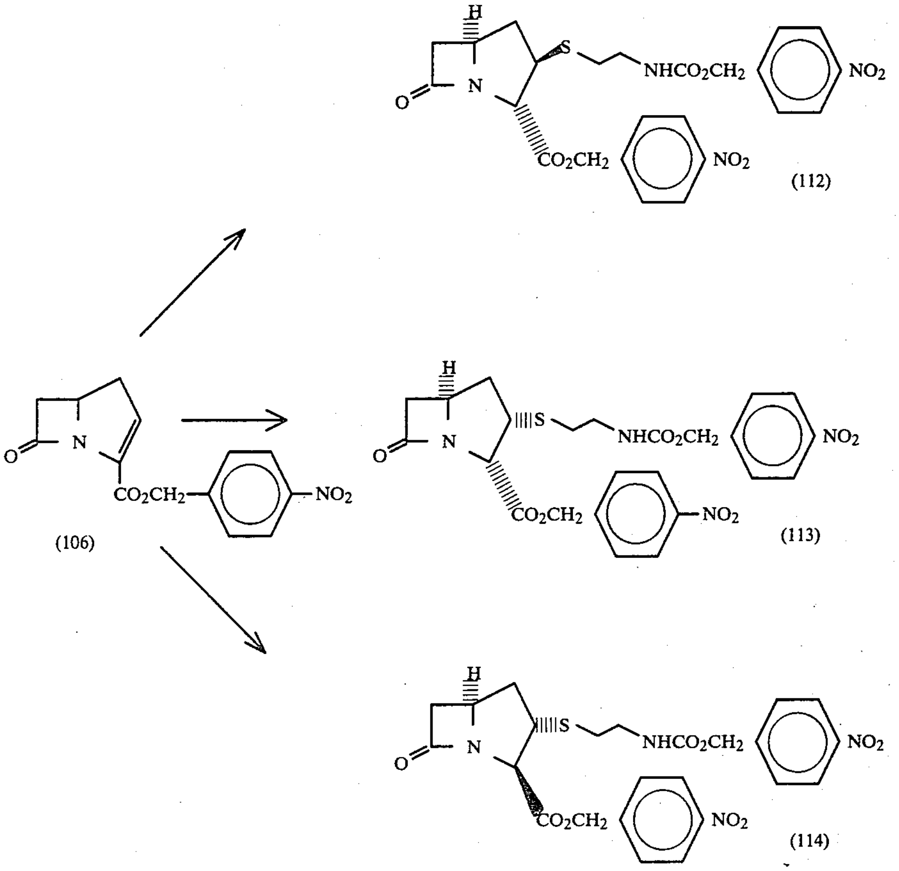

(106) (112) (113) (114)

To a stirred suspension of p-nitrobenzyl-7-oxo-1-azabicyclo[3.2.0]hept-2-ene-2-carboxylate (106) (576 mg) in dry dimethyl formamide (5 ml) at ambient temperature was added p-nitrobenzyloxycarbonylaminoethanethiol (512 mg) followed by powdered potassium carbonate (27.6 mg). Stirring was continued and the starting material (106) dissolved. A further 43 mg of the thiol was added after 30 minutes and after a total of 40 minutes the orange solution was diluted with ethyl acetate, washed with water then brine, dried over magnesium sulphate, filtered and evaporated. The crude material was chromatographed on silica gel 60 (<230 mesh) (30 g), eluting with 50–70% ethyl acetate in 60°–80° petroleum ether to give the three isomers (112), (113) and (114).

The first fractions obtained gave a gum (765 mg) shown by n.m.r. to be a mixture of the C-2α isomers (112) and (113) in the ratio 5:7; $\nu_{max}$($CHCl_3$) 3460, 1770, 1730, 1520, 1350 $cm^{-1}$; δ ppm ($CDCl_3$) 1.47–2.91 (5H, C4-$CH_2$, side-chain $CH_2$, C6-H), 2.19–4.21 (5H, side-chain $CH_2$, C6-H, C5-H, C3-H), 4.39 [7/12H, d, J 6 Hz, C2-H of (113)], 4.79 [5/12H, d, J 7 Hz, C2-H of (112)], 5.18 and 5.27 (4H, 2 singlets, benzyl $CH_2$'s, obscurring 1H, NH), 7.40–7.60 (4H, Ar), 8.15 and 8.18 (4H, 2 doublets J8 Hz, Ar).

The third, more polar product (114) was obtained as a foam (180 mg); $\nu_{max}$($CHCl_3$) 3460, 1770, 1740, 1730, 1520, 1350 $cm^{-1}$; δppm ($CDCl_3$) 1.89 (1H, ddd, J 12, 12 and 9.5 Hz, C4-H), 2.32 (1H, ddd, J12, 6 and 6 Hz, C4-H), 2.72 (2H, t, J6 Hz, side-chain $CH_2$), 2.80 (1H, dd, J 16 and 3 Hz, C6-H), 3.13 (1H, dd, J 16 and 4.5 Hz, C6-H), 3.31 (2H, t, J6 Hz, side-chain $CH_2$), 3.57–3.87 (2H, m, C3-H and C5-H), 4.16 (1H, d, J 7.5 Hz, C2-H), 5.19 and 5.30 (4H, 2 singlets, benzyl $CH_2$'s) obscurring 1H, NH, 7.48, 7.56, 8.17 and 8.18 (8H, 4 doublets J 8 Hz, Ar).

EXAMPLE 56

Benzyl 7-oxo-3-(2-tritylaminoethylthio)-1-azabicyclo[3.2.0-]heptane-2-carboxylate

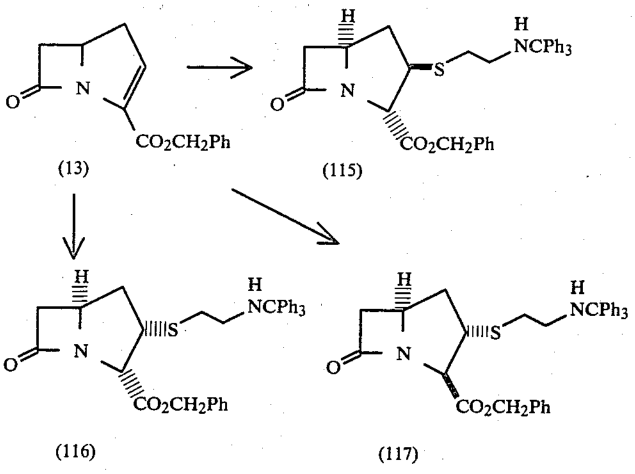

(13) (115) (116) (117)

A solution of benzyl 7-oxo-1-azabicyclo[3.2.0]hept-2-ene-2-carboxylate (13) (0.075 g) in dry dimethylformamide (2 ml) was treated with 2-tritylaminoethanethiol (0.200 g) and potassium carbonate (0.021 g) The reaction was stirred at room temperature for 20 hours, and the solvent was then distilled off in vacuo. The residue was partitioned between ethyl acetate and brine and the separated organic phase was dried over sodium sulphate and concentrated. It was chromatographed on silica gel 60, eluting with ethyl acetate/60°-80° petroleum ether 7:3 grading to 6:4. This gave three isomers of benzyl 7-oxo-3-(2-tritylaminoethylthio)-1-azabicyclo[3.2.0-]heptane-2-carboxylate which are described below an increasing order of polarity. The 2α, 3β-isomer (115) (0.043 g) showed $\nu_{max}$ ($CHCl_3$) 3020, 2940, 2850, 1770, 1745 and 1600 $cm^{-1}$; τ($CDCl_3$) 2.4–3.0(20H, m, phenyls), 4.90(2H, s, benzyl $CH_2$), 5.39(1H, d, J 6 Hz, C2-H), 5.8–6.1(1H, m, C5-H), 6.69(1H, td, J9 and 6 Hz, C3-H), 6.71(1H, dd, J16 and 4 Hz, C6-H), 7.36(1H, dd J16 and 2½ Hz, C6-H), 7.3–7.8(4H, m, $SCH_2CH_2N$), 7.8–8.1(2H, m, C4-$H_2$) and 8.13(1H, br s, NH). The 2α, 3α-isomer (116) (0.017 g) showed $\nu_{max}$ ($CHCl_3$) 3000, 2860, 1775, 1745 and 1600 $cm^{-1}$; τ ($CDCl_3$) 2.3–3.2(20H, m, phenyl), 4.91(2H, s, benzyl $CH_2$), 5.69(1H, d, J6 Hz, C2-H), 6.1–6.4(1H, m, C5-H), 6.52(1H, dt J8 and 6 Hz, C3-H), 6.76(1H, dd J 15 and 4½ Hz, C6-H), 7.32(1H, dd J15 and 2 Hz, C6-H), 7.3–7.8(5H, m, $SCH_2CH_2N$ and C4-H), 8.10(1H, br s, NH) and 8.53(1H, ddd J13, 8 and 7 Hz, C4-H); ($M^+$ at m/e 562. $C_{35}H_{34}N_2O_3S$ requires 562). The 2β, 3α-isomer (117) (0.040 g) showed $\nu_{max}$ ($CHCl_3$) 3010, 2860, 1775, 1745 and 1600 $cm^{-1}$; τ ($CDCl_3$) 2.4–3.0(20H, m, phenyls), 4.87(2H, s, benzyl $CH_2$), 6.07(1H, d J7Hz, C2-H), 6.3–6.6 (1H m, C5-H), 6.66(1H, ddd J13, 7 and 5 Hz, C3-H), 6.93 (1H, dd J16 and 4 Hz, C6-H), 7.24(1H, dd J16 and 2½ Hz, C6-H), 7.3–7.8(4H m, $SCH_2CH_2N$) and 7.8–8.4(3H, m, C4-$H_2$ and NH); ($M^+$ at m/e 562. $C_{35}H_{34}N_2O_3S$ requires 562).

EXAMPLE 57

Preparation of p-nitrobenzyl 3-(2-triphenylmethylaminoethylthio)-7-oxo-1-azabicyclo[3.2.0]heptane-2-carboxylate

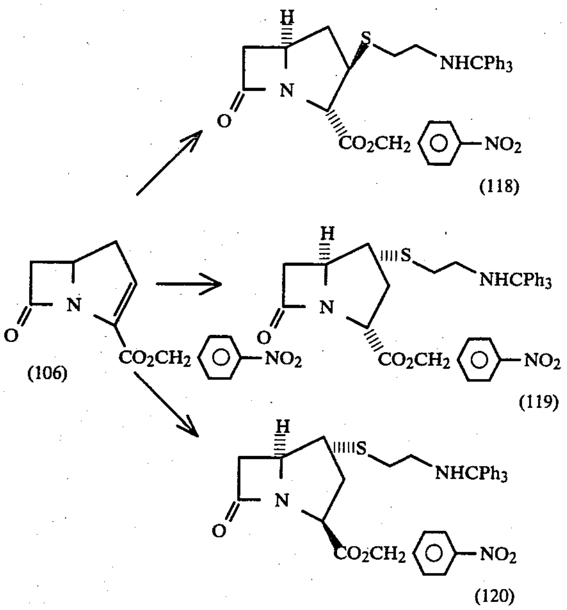

(118) (106) (119) (120)

To p-nitrobenzyl 7-oxo-1-azabicyclo[3.2.0]hept-2-ene-2-carboxylate (106) (450 mg) was added with stirring under an argon atmosphere, a solution of triphenylmethylaminoethanethiol (1.02 g) in dry dimethylformamide (4.3 ml) followed by powdered potassium carbonate (21 mg). Stirring was continued at ambient temperature and the starting material (106) gradually dissolved over an hour to give a red-orange solution. After 3.5 hours a further 0.12 g of the thiol in dry dimethylformamide (0.5 ml) was added. After a total of 4.5 hours the volume of the solution was reduced by evaporation and the residue was taken up in ethyl acetate, washed with water, then brine, dried over magnesium sulphate, filtered and evaporated. The residual oil was taken up in toluene and chromatographed on silica gel (<230 mesh). Elution with 30% ethyl acetate in petroleum ether (60°-80°) almost completely separated the three products (118) (119) and (120).

The first fractions contained the 2α, 3β-isomer (118) as a gum (275 mg) which crystallised from ethyl acetate/petroleum ether (60°-80°) to give rectangular plates m.p. 81°-7°; $\nu_{max}$ ($CHCl_3$) 1765m 1750, 1522, 1350 $cm^{-1}$; δppm ($CDCl_3$) 1.95(1H, s, NH), 2.08(2H, dd, J 8 and 6 Hz, C4-$H_2$), 2.33(2H, t, J6 Hz, side-chain $CH_2$), 2.56-2.80(3H, m, side chain $CH_2$ and C6-H), 3.20-3.51 [2H, including δ3.32(1H, dd J 16 and 5 Hz, C6-H)+C3-H], 3.93-4.16(1H, m, C5-H), 4.66(1H, d, J 7 Hz, C2-H), 5.18 (2H, s, benzyl $CH_2$), 7.05-7.50(17H, m, Ar), 8.12(2H, d, J8 Hz, Ar), (Found: C, 69.21; H, 5.80; N, 6.65%. $C_{35}H_{33}N_3O_5S$ requires C, 69.19; H, 5.44; N, 6.92%).

Further elution gave 54 mg of (118) contaminated by a trace of (119) followed by 28 mg of a 1:1 mixture of (118) and (119) [t.l.c. analysis] and then 130 mg of the 2α, 3α-isomer (119) as a gum. $\nu_{max}$ ($CHCl_3$) 1768, 1750 1522, 1345 $cm^{-1}$. δppm ($CDCl_3$) 1.50(1H, ddd, J 12, 9.5 and 8 Hz, C4-H), 1.85 (1H, centre broad signal, NH), 2.33 (2H, t, J6 Hz, side chain $CH_2$)-obscuring IC4-H, 2.69 (2H, t, J6 Hz, side-chain $CH_2$), 2.70(1H, dd, J 16 and 2.5 Hz, C6-H), 3.27(1H, dd, J 16 and 4.5 Hz, C6-H), 3.43-3.90(2H, two multiplets, C3 and C5-H's), 4.31(1H, d, J 6.5 Hz, C2-H), 5.18(2H, s, benzyl $CH_2$), 7.10-7.50(17H, Ar), 8.14(2H, d, J 8 Hz, Ar).

A fraction containing a mixture of (119) and (120) (19 mg) was then obtained followed by the 2β, 3α-isomer (120) as a foam (411 mg); $\nu_{max}$ ($CHCl_3$) 1765, 1740, 1522, 1345 $cm^{-1}$; δppm ($CDCl_3$) 1.70-2.90[8H, including 2.32(2H, t, J 6 Hz, side chain $CH_2$), 2.67(2H, t, J6 Hz, side chain $CH_2$), 2.76(1H, dd, J16 and 2.5 Hz, C6-H), obscuring C4-$H_2$ and NH] 3.08(1H, dd, J 16 and 4.5 Hz, C6-H), 3.18-3.70(2H, overlapping m's, C3-H and C5-H), 3.95(1H, d, J7.5 Hz, C2-H), 5.12 and 5.30(2H, ABq, J, 13 Hz, benzyl $CH_2$), 7.10-7.54(17H, Ar), 8.13(2H, d, J8 Hz, Ar).

EXAMPLE 58

Benzyl 3-p-acetamidophenylthio-7-oxo-1-azabicyclo[3.2.0]heptane-2-carboxylate

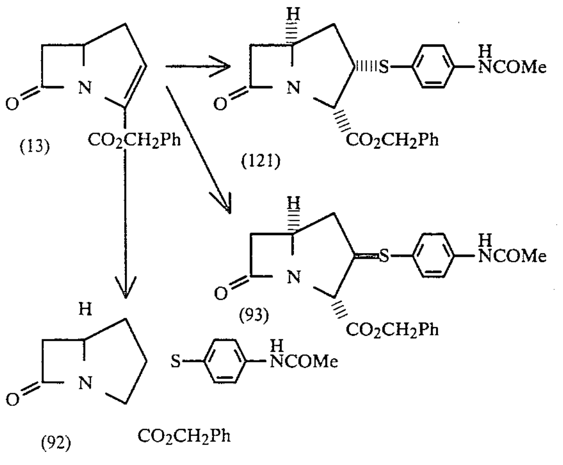

(13) (121) (93) (92)

A solution of benzyl 7-oxo-1-azabicyclo[3.2.0]hept-2-ene-3-carboxylate (13) (0.700 g) in dry dimethylformamide (5 ml) was treated with p-acetamidophenylthiol (0.480 g) and powdered potassium carbonate (0.199 g) The reaction mixture was stirred at room temperature for 1 hour and the solvent was then removed under reduced pressure at <30°. The residue was partitioned between ethyl acetate and brine and the organic phase was separated, dried over sodium sulphate and then concentrated. This was then chromatographed on silica gel 60 (<230 mesh) eluting with ethyl acetate/60°-80° petroleum ether 7:3 grading to 1:0, in order to separate the three isomers of benzyl 3-p-acetamidophenylthio-7-oxo-1-azabicyclo[3.2.0]heptane-2-carboxylate. The first compound to be eluted was the 2α, 3α-isomer (121) (0.109 g); $\nu_{max}$ ($CHCl_3$) 3470, 3350, 3000, 1770, 1745, 1690, 1590 and 1500 $cm^{-1}$; τ($CDCl_3$) 2.05(1H, br s, NH), 2.4-3.0(9H, m, phenyls), 4.94(2H, s, benzyl $CH_2$), 5.63(1H, d, J 5 Hz, C2-H), 5.9-6.2(2H, m, C3-H and C5-H), 6.70(1H, dd J16 and 5 Hz, C6-H), 7.19(1H, dd, J16 and 2½ Hz, C6-H), 7.47(1H, dt J14 and 7 Hz, C4-H), 7.90(3H, s, $COCH_3$) and 8.31(1H, dt J14 and 7 Hz, C4-H); ($M^+$ at m/e 410.1301. $C_{22}H_{22}N_2O_4S$ requires 410. 1298). The next fractions contained the 2α, 3β-isomer (92) (0.280 g); $\nu_{max}$ ($CHCl_3$) 3470, 3000, 1770, 1750 sh, 1695, 1590 and 1500 $cm^{-1}$; τ($CDCl_3$) 2.18(1H, br s, NH), 2.5-2.8(9H, m, phenyls), 4.83(2H, s, benzyl $CH_2$), 5.29 (1H, d J 7 Hz, C2-H), 5.8-6.0(1H, m, C5-H), 6.14(1H, td J8 and 7 Hz, C3-H), 6.69(1H, dd J16 and 5½ Hz, C6-H), 7.31 (1H, dd J16 and 2½ Hz, C6-H), 7.6-8.1(2H, m, C4-$H_2$) and 7.89(3H, s, $COCH_3$); ($M^+$ at m/e 410.1290. $C_{22}H_{22}N_2O_4S$ requires 410.1298). The final compound to be eluted was the 2β, 3α-isomer (93) (0.334 g); m.p. 171°-4° (acetone/60°-80° petroleum ether); $\nu_{max}$ ($CHCl_3$) 3470, 3350, 3000, 1770, 1740, 1695, 1590 and 1500 $cm^{-1}$; τ($CDCl_3$) 1.39(1H, br s, NH), 2.4-2.8(9H, m, phenyls), 4.80(2H, s, benzyl $CH_2$), 5.89(1H, d J 7 Hz, C2-H), 6.07(1H, ddd J12 7 and 5 Hz, C3-H), 6.2-6.5(1H, m, C5-H), 6.89(1H, dd J16 and 4 Hz, C6-H), 7.20(1H, dd J16 and 2½ Hz, C6-H), 7.5-8.2(2H, m, C4-$H_2$) and 7.88(3H, s, $COCH_3$); (Found: C, 64.2; H, 5.4; N, 6.9%. $C_{22}H_{22}N_2O_4S$ requires C, 64.4; H, 5.4 and N, 6.8%).

EXAMPLE 59

Benzyl 3-(2-nitroethylthio)-7-oxo-1-azabicyclo[3.2.0]heptane-2-carboxylate

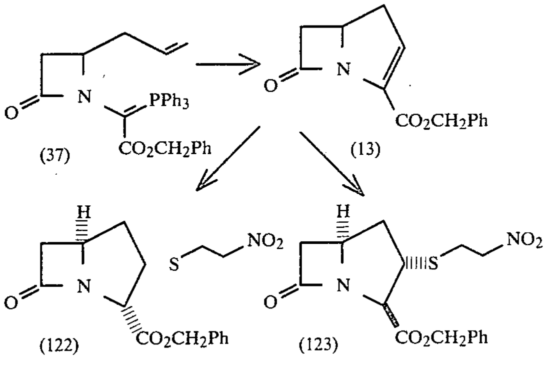

(37) (13) (122) (123)

An ethyl acetate solution of 4-allyl-1-(1-benzyloxycarbonyl-1-triphenylphosphoranylidenemthyl)azetidin-2-one (37) (1.46 g) was ozonolysed and cyclized as described in Example 53. The crude product (13) was dissolved in dry dimethylformamide (5 ml) and a solution of 2-nitroethanethiol (0.30 g) in dimethylformamide (2 ml) was added, followed by powdered potassium carbonate (0.19 g). The reaction was stirred at room temperature for 2 hours and the solvent was then stripped off under high vacuum. The residue was partitioned between ethyl acetate and brine and the organic phase was separated, dried over sodium sulphate and concentrated. It was chromatographed on silica gel 60 (<230 mesh) eluting with ethyl acetate/60°-80° petroleum ether 3:7 grading to 7:3, and fractions containing the required products were rechromatographed on the same support using ethyl acetate/60°-80° petroleum ether 4:6. This gave two isomers of benzyl 3-(2-nitroethylthio)-7-oxo-1-azabicyclo[3.2.0]heptane-2-carboxylate (122) and (123). The less polar compound was the 2α, 3α-isomer (122) (0.025 g); $\nu_{max}$ ($CHCl_3$) 3020, 2960, 1770, 1750sh and 1560 $cm^{-1}$; τ($CDCl_3$) 2.66(5H, s, phenyl), 4.82(2H, s, benzyl $CH_2$), 5.60(2H, t J7 Hz, $CH_2NO_2$), 5.65(2H, d, J6½ Hz, C2-H), 5.9-6.4(2H, m, C3-H and C5-H), 6.70(1H, dd J15 and 4½ Hz, C6-H), 6.94 and 6.96(2H, 2t J7 Hz, $SCH_2$), 7.26(1H, dd J15 and 2 Hz, C6-H), 7.41(1H, dt J13 and 6 Hz, C4-H), and 8.44(1H, ddd J13, 9 and 7 Hz, C4-H); ($M^+$ at m/e 350. $C_{16}H_{18}N_2O_5S$ requires 350). The more polar product was the 2β, 3α-isomer (123) (0.010 g); $\nu_{max}$ ($CHCl_3$) 3000, 2940, 1770, 1740 and 1560 $cm^{-1}$; τ($CDCl_3$) 2.65(5H, s, phenyl), 4.72 and 4.89 (2H, ABq J12 Hz, benzyl $CH_2$) 5.64(2H, t J6½ Hz, $CH_2NO_2$), 5.89(1H, d J7 Hz, C2-H), 6.1-6.5(2H, m, C3-H and C5-H), 6.7-7.1(3H, m, C6-H and $SCH_2$), 7.18(1H, dd J15 and 2½ Hz, C6-H), 7.73(1H, dt J12 and 6 Hz, C4-H) and 8.09(1H, td J12 and 10 Hz, C4-H); $M^+$ m/e 350. $C_{16}H_{18}N_2O_5S$ requires 350).

EXAMPLE 60

Benzyl 3-(2-hydroxyethylthio)-7-oxo-1-azabicyclo[3.2.0]heptane-2-carboxylate

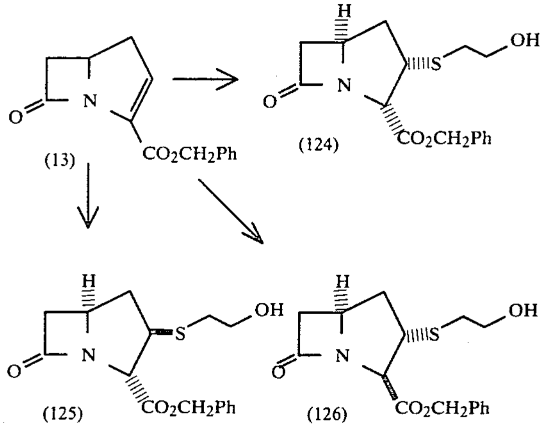

(13) (124) (125) (126)

The benzyl ester (13) (0.175 g) in dimethylformamide (2 ml) was treated with mercaptoethanol (0.085 g; 77 μl; 1.5 equivalent) in the presence of finely-ground anhydrous potassium carbonate (0.10 g; 1 equiv.) at 0° for 1 h. The reaction mixture was diluted with ethyl acetate, washed with saturated aqueous sodium chloride solution (×3) and the ethyl acetate dried over $MgSO_4$. Recovery gave a gum which was chromatographed on Kieselgel (<230 mesh) (10×2 cm). Elution with ethyl acetate-chloroform (1:1) (4 ml fractions) gave (fractions 14–17) benzyl 3α-(2-hydroxyethylthio)-7-oxo-1-azabicyclo[3.2.0]heptane-2α-carboxylate (124) as a gum (0.068 g), $\nu_{max}$ ($CHCl_3$) 3500 br, 1760 and 1745 sh $cm^{-1}$; δ ($CDCl_3$) 1.61(1H, 5 lines, J 14, 8 and 7 Hz, C4α-H), 2.22br(1H, $D_2O$ exchangeable), 2.53 (1H, q, J 14 and 7 Hz, C4β-H), 2.69(2H, m), 2.77(1H, dd, J 15 and 3 Hz, 6β-H), 3.28(1H, dd, J 15 and 5 Hz, 6α-H), 3.62br (2H, sharpening to q, J 3.5 Hz on $D_2O$ exchange), 3.77(2H m, w½ 15 Hz, 3β-H+5α-H), 4.46 (1H, d, J 5.6 Hz, C2β-H), 5.13(2H, s), and 7.29(5H, s). (Found: $M^+$, 321.1055. $C_{16}H_{19}NO_4S$ requires M, 321.1035).

Fractions 18–20 contained isomers (124) and (125) (0.031 g) in the ratio 7:3 (n.m.r. spectrum).

Further elution of the column (fractions 21–27) gave benzyl 3β-(2-hydroxyethylthio)-7-oxo-1-azabicyclo[3.2.0]heptane-2α-carboxylate (125) as a gum (0.031 g), $\nu_{max}$ ($CHCl_3$) 3500br, 1760, 1745 $cm^{-1}$; δ2.18(2H, dd, J9 and 6 Hz, C4-$H_2$), 2.25br(1H, $D_2O$ exchangeable), 2.70(1H, dd, J 16 and 4 Hz, C6β-H), 2.69(2H, m), 3.32(1H, dd, J 16 and 5 Hz, C6α-H), 3.65(3H, m, sharpening on $D_2O$ exchange, —S-$CH_2$-$C\underline{H}_2$-OH+C3α-H), 4.05(1H, m, W½ 10 Hz, C5α-H), 6.74 (1H, d, J 7. 1 Hz, C2β-H), 5.14(2H, s) and 7.30(5H, s); on irradiation at the frequency of the C5α-proton, the signals of the C6-proton resonances simplified to doublets J 16 Hz, and C4-$H_2$ resonance sharpened to a doublet J 9 Hz (Found: $M^+$ at m/e 321.1102. $C_{16}H_{19}NO_4S$ requires 321.1035).

Finally fractions 33–38 yielded benzyl 3α-(2-hydroxyethylthio)-7-oxo-1-azabicyclo[3.2.0]heptane-2β-carboxylate (126) (0.020 g) $\nu_{max}$ ($CHCl_3$) 3500br, 1755, 1730 $cm^{-1}$; δ($CDCl_3$) 2.30(3H, m, C4-$H_2$ and OH), 2.65–3.1 (3H, m, —S-$C\underline{H}_2$-$CH_2OH$+C6α-H), 3.5–4.05(4H, m, —S-$CH_2$-$C\underline{H}_2OH$+C5α-H+C6β-H), 4.22(1H, d, J 7.5 Hz), 5.28(2H, s) and 7.38(5H, s).

EXAMPLE 61

Benzyl 7-oxo-3-tert-butylthio-1-azabicyclo[3.2.0]heptane-2-carboxylate

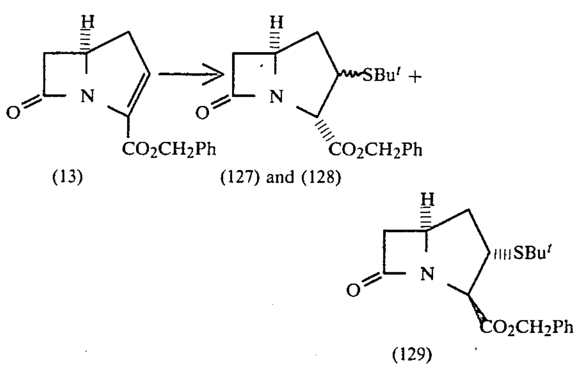

(13) (127) and (128) (129)

Benzyl 7-oxo-1-azabicyclo[3.2.0]hept-2-ene-2-carboxylate (13) (0.05 g) was stirred in dry dimethylformamide (1 ml) with tert.-butyl mercaptan (0.1 ml) and powdered potassium carbonate (0.016 g). After 0.5 h at room temperature excess thiol was removed with a stream of argon. The reaction mixture was diluted with ethyl acetate (30 ml) and washed with 0.1 N HCl and then water. The dried ($MgSO_4$) organic phase was evaporated (in vacuo) and the crude material (0.075 g) chromatographed on silica gel 60 (<230 mesh) eluting with 3:7 ethyl acetate/60°-80° petroleum ether. Initially eluted, was a mixture of isomers (127) and (128) (0.026 g) of the α-carboxylate in a ratio of ca 8:1, $\nu_{max}$ ($CHCl_3$) 1765 and 1745 $cm^{-1}$; δ ($CDCl_3$) for major isomer 1.25(9H, s, $Bu^t$), 2.19(2H, dd, J 9 and 6 Hz, CH-$H_2$), 2.68(1H, dd, J 16 and 3 Hz, C6-H trans), 3.29(1H, dd, J 16 and 6 Hz, C6-H cis), 3.45(1H, td, J 9 and 8 Hz, C3-H), 4.10-3.86(1H, m, C5-H), 4.66(1H, d, J 8 Hz, C2-H), 5.10(2H, s, $CH_2Ph$), 7.26(5H, s, Ar). (Found: M+, 333.1396. $C_{18}H_{23}NO_3S$ requires M, 333.1399).

The β-carboxylate (129) (0.017 g) was obtained as a single isomer, m.p. 85°-87° (diethyl ether/60°-80° petroleum ether), $\nu_{max}$ ($CHCl_3$) 1765 and 1740 $cm^{-1}$, δ ($CDCl_3$) 1.25(9H, s, $Bu^t$), 1.70-2.35(2H, m, C4-$H_2$), 2.72(1H, dd, J 16 and 2½ Hz, C6-H trans), 3.05(1H, dd, J 16 and 5 Hz, C6-H cis), 3.45-3.74(2H, m, C3-H, C5-H), 4.00(1H, d, J 8 Hz, C2-H), 5.13(2H, s, C$\underline{H}_2$Ph), 7.28 (5H, s, Ar). (Found: C, 64.4; H, 6.8; N, 3.9; S, 9.8 M+, 333.1378. $C_{18}H_{23}NO_3S$ requires C, 64.8; H, 6.9; N, 4.2; S, 9.6%. M, 333.1399).

EXAMPLE 62 p-Nitrobenzyl 7-oxo-3-triphenylmethylthio-1-azabicyclo[3.2.0]heptane-2-carboxylate

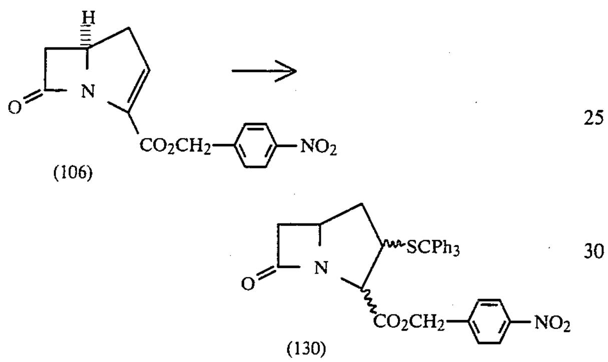

(106)

(130)

p-Nitrobenzyl 7-oxo-1-azabicyclo[3.2.0]hept-2-ene-2-carboxylate (106) (0.1 g) was stirred in dry dimethylformamide (2 ml) with triphenylmethyl mercaptan (0.3 g) and potassium carbonate (0.024 g). After 1½ h at room temperature the dimethylformamide was removed under high vacuum and the residue dissolved in ethyl acetate and washed with brine. The dried ($MgSO_4$) organic phase was evaporated to dryness and the residue chromatographed on Kieselgel 60 (230-400 mesh ASTM) eluting initially with 1:10 ethyl acetate/60°-80° petroleum ether and then 3:7 ethyl acetate/60°-80° petroleum ether to give two isomers of the product (130).

Isomer (i), (foam, 0.05 g) (less polar isomer), $\nu_{max}$ ($CHCl_3$) 1765 and 1750 (sh) $cm^{-1}$; δ ($CDCl_3$) 1.97(1H, ddd, J 12, 9 and 3 Hz, C4-H), 2.20-2.70(2H, m, C6-H and C4-H). 2.80-3.05(1H, m, C3-H), 3.22(1H, dd, J 15 and 6 Hz, C6-H cis), 3.63(1H, d, J 8 Hz, C2-H), 3.75-4.00 (1H, m, C5-H), 5.06 and 5.35(2H, ABq, J 13 Hz, $\underline{C}H_2$-$C_6H_4$-p-$NO_2$), 7.10-7.40(15H, Ar), 7.49(2H, d, J 9 Hz, Ar), 8.09(2H, d, J 9 Hz, Ar).

Isomer (ii), was obtained as a crystalline solid (0.06 g) m.p. ca 200° (decomp.), $\nu_{max}$ ($CHCl_3$) 1765 and 1745 $cm^{-1}$; δ ($CDCl_3$) 1.84-2.17(2H, m, C4-$H_2$), 2.66(1H, dd, J 16 and 3 Hz, C6-H trans), 3.00(1H, dd, J 16 and 6 Hz, C6-H cis), 3.00-3.50(m, C2-H, C3-H and C5-H), 5.13 and 5.39(2H, ABq, J 12 Hz, $CH_2$-$C_6H_4$-p-$NO_2$), 7.10-7.40(15H, Ar), 7.53(2H, d, J 9 Hz, Ar), 8.06(2H, d, J 9 Hz, Ar). (Found: C, 70.7; H, 5.1; N, 4.9; S, 5.9. $C_{33}H_{28}N_2O_5S$ requires C, 70.2; H, 5.0; N, 5.0; S, 5.7%).

EXAMPLE 63

Benzyl 6-(3-methoxycarbonylprop-2-en-1-yl)-7-oxo-3-phenylthio-1-azabicyclo[3.2.0]heptane-2-carboxylate

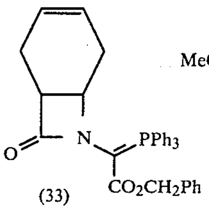

(33)

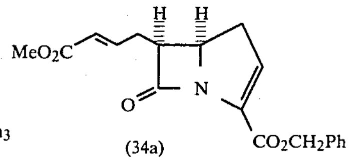

(34a)

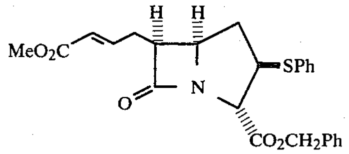

(94)

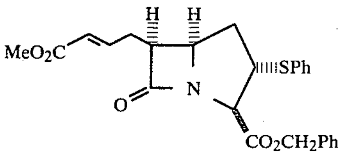

(95)

The phosphorane (33) (1.00 g) was ozonolysed and cyclized to the diester (34a) as described in Example 12. However the crude product was not chromatographed but was immediately dissolved in dry dimethylformamide (8 ml). This solution was stirred at room temperature and treated with thiophenol (0.20 ml) followed by powdered potassium carbonate (0.13 g). After a period of 1 hour the solvent was removed under high vacuum and the residue partitioned between ethyl acetate and brine. The organic phase was separated, dried over sodium sulphate and then concentrated. The residue was chromatographed on silica gel (60) (<230 mesh) eluting with ethyl acetate/60°-80° petroleum ether 3:7 to give two products. The least polar product was benzyl 6-(3-methoxycarbonylprop-2-en-1-yl)-7-oxo-3β-phenylthio-1-azabicyclo[3.2.0]heptane-2α-carboxylate (94) (0.202 g) contaminated with a trace of the 2α, 3α-isomer It was a gum; $\nu_{max}$ ($CHCl_3$) 3000, 2960, 1765, 1740, 1725 and 1660 $cm^{-1}$; τ($CDCl_3$) 2.6-2.9 (10H, m, phenyls), 3.16 (1H, dt J15 and 6 Hz, C$\underline{H}_2$-CH=), 4.20(1H, dt J15 and 1 Hz =C$\underline{H}$-$CO_2$), 4.88(2H, s, benzyl $CH_2$), 5.30(1H, d J7 Hz, C2-H), 5.78(1H, q J6 Hz, C5-H), 5.9-6.6(2H, m, C3-H and C6-H), 6.33(3H, s, $OCH_3$), 7.3-7.7(2H, m, C$\underline{H}_2$-CH=) and 7.82 (2H, dd J9 and 6 Hz, C4-$H_2$); (M+ at m/e 451.1462. $C_{25}H_{25}NO_5S$ requires 451.1453). The more polar product was the 2β, 3α-isomer (95) (0.191 g); $\nu_{max}$($CHCl_3$) 3000, 2950, 1770, 1730 and 1660 $cm^{-1}$; τ($CDCl_3$) 2.6-2.9(10H, m, phenyls), 3.22(1H, dt J 16 and 6 Hz, $CH_2$-C$\underline{H}$=), 4.30(1H, dt J16 and 1 Hz, =C$\underline{H}$-$CO_2$), 4.84(2H, s, benzyl $CH_2$), 5.86 (1H, d 7 Hz, C2-H), 5.9-6.4(2H, m, C3-H and C5-H), 6.32(3H, s, $OCH_3$), 6.70(1H, ddd J10, 6 and 5 Hz, C6-H), 7.4-8.1(4H, m, C4-$H_2$ and C$\underline{H}_2$-CH=); (M+ at m/e 451.1473 $C_{25}H_{25}NO_5S$ requires 451.1453).

EXAMPLE 64

Sodium
3-ethylthio-6-(3-methoxycarbonylprop-2-en-1-yl)-7-oxo-1-azabicyclo[3.2.0]heptane-2α-carboxylate

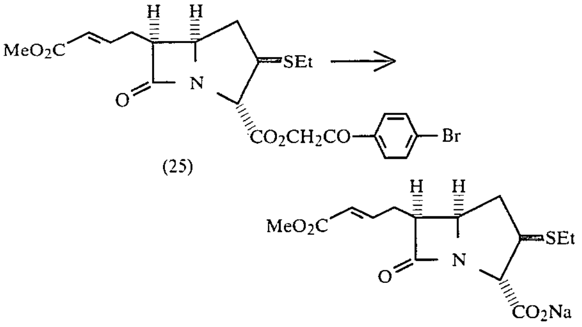

(25)

(131)

The p-bromophenacyl ester (25) (0.125 g) in anhydrous dimethylformamide (0.25 ml) was treated with an excess of sodium thiophenoxide (0.020 g; ca 1.5 equiv.) at 0° in an atmosphere of argon. The solution was stirred at room temperature for 3.5 hour at which time all the ester (25) had been consumed. Cold ether (10 ml) was added dropwise, and the solution stirred at 0° for 30 minutes. The solution was decanted, and the precipitate washed well with further portions of cold, dry ether, to give the 2α, 3β-isomer (131) (0.074 g) as the dimethylformamide hemi-solvate, m.p. 215°-218°. (Found: C, 49.8; H, 5.5; N, 5.3%. $C_{14}H_{18}NNaO_5S$. ½ DMF requires C, 50.0; H, 5.8; N, 5.7%; $\nu_{max}$ ($CHCl_3$) 1750, 1720, 1665 (DMF), 1655sh, 1605 $cm^{-1}$; δ ($D_2O$) 1.09 (3H, t, J 8 Hz), 1.98 (2H, t, J 7 Hz, C4-$H_2$), 2.3-2.6(2H, m), 2.53(2H, q, J 8 Hz), 2.71 (s) and 2.87 (s) (together 3H, DMF), 3.60 (3H, s), 3.67(1H, q, J ca 6 Hz, C6-H), 4.12 (1H, q, J ca 6 Hz, C5-H), 4.32 (2H, d, J 7 Hz, C2-H), 5.85 br (1H, d, J 16 Hz), 6.89 (1H, dt, J 16, 6 Hz). 7.84 (0.5 H, DMF).

EXAMPLE 65

Sodium
3-ethylthio-6-(3-methoxycarbonylprop-2-en-1-yl)-7-oxo-1-azabicyclo[3.2.0]heptane-2β-carboxylate

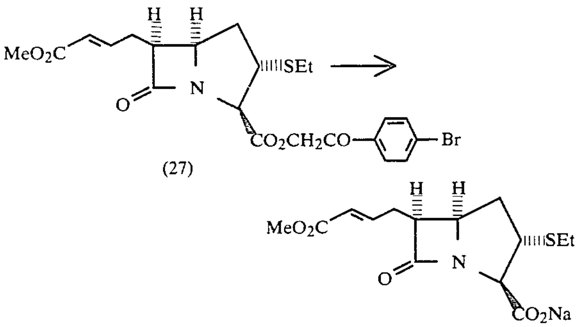

(27)

(132)

The p-bromophenacyl ester (27) (0.077 g) in anhydrous dimethylformamide (0.5 ml) was treated with an excess of sodium thiophenoxide (0.03 g; 1.5 equiv.) in an atmosphere of argon at 0°. The solution was stirred at room temperature for 2 hours. Precipitation, and recover of the crude sodium salt (132) as in Example 64 gave a gum (0.045 g); $\nu_{max}$ ($CHCl_3$) 1750, 1720 and 1610 $cm^{-1}$.

EXAMPLE 66

Benzyl
3-ethylthio-6-(3-methoxycarbonylprop-2-en-1-yl)-7-oxo-1-azabicyclo[3.2.0]heptane-2α-carboxylate

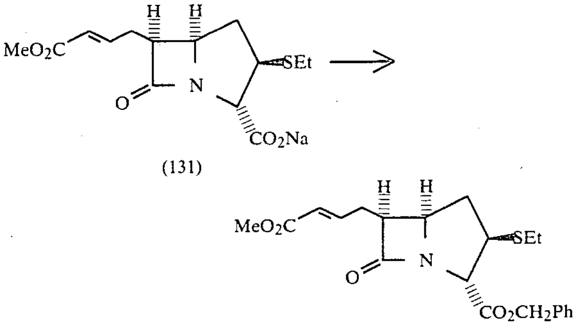

(131)

(134)

The sodium salt (131) (0.02 g) in anhydrous dimethylformamide (0.2 ml), was treated with an excess of benzyl bromide (0.05 ml) overnight. Removal of the solvent in vacuo (oil pump, room temperature), chromatography of the residue (0.04 g) on Kieselgel 60 (Merck; <230 mesh), followed by elution with ethyl acetate-petroleum ether (1:4) afforded benzyl 6-(3-methoxycarbonylprop-2-en-1-yl)-3β-ethylthio-7-oxo-1-azabicyclo[3.2.0]heptane-2α-carboxylate (133) as a gum (0.019 g), $\nu_{max}$ ($CHCl_3$) 1760, 1735, 1720, 1660 $cm^{-1}$; δ ($CDCl_3$) 1.18 ( 3H, t, J 7 Hz), 2.0-2.30(2H, m, C4-$H_2$), 2.3-2.75(2H, m, C6 side-chain $CH_2$), 2.56(2H, q, J 7 Hz, —$SC\underline{H}_2CH_3$), 3.2-3.7(2H, m, C3-H and C6-H), 3.72(3H, s), ca. 4.1 br (1H, m, C5-H), 4.69(1H, d, J 7 Hz, C2-H), 5.15 (2H, s), 5.82 br (1H, d, J 15 Hz), 6.85(1H, dt, J 15, 6 Hz), 7.33(5H, s). (Found: m/e 403.1450. $C_{21}H_{25}NO_5S$ requires $M^+$ 403.1453).

EXAMPLE 67

Benzyl
3-ethylthio-6-(3-methoxycarbonylprop-2-en-1-yl)-7-oxo-1-azabicyclo[3.2.0]heptane-2β-carboxylate

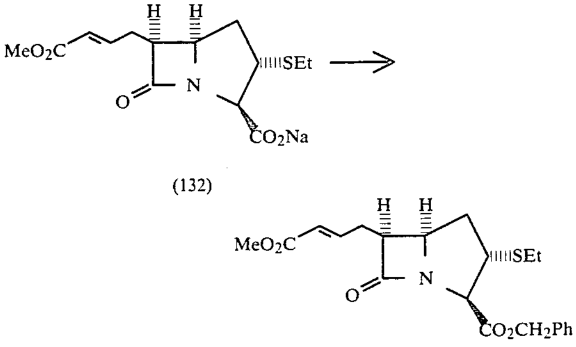

(132)

(134)

Benzylation of the sodium salt (132) (0.045 g) with benzyl bromide (0.2 ml) in anhydrous dimethylformamide (0.5 ml) overnight as previously described, gave an oil (0.080 g) which was chromatographed on silica gel 60. Elution with ethyl acetate/60°-80° petroleum ether (3:7) gave benzyl 3α-ethylthio-6-(3-methoxycarbonylprop-2-en-1-yl)-7-oxo-1-azabicyclo[3.2.0]heptane-2β-carboxylate (134) as a gum (0.085 g) which crystallised (ethyl acetate-light petroleum) as needles (0.029 g) m.p. 117°; $\nu_{max}$ ($CHCl_3$) 1765, 1735, 1720, 1655 $cm^{-1}$; δ ($CDCl_3$) 1.17 (3H, t, J 7 Hz), 1.9–2.1(2H, m, C4-$H_2$), 2.3–2.6(2H, m), 2.54(2H, q, J 7 Hz), 3.28(1H, m, C6-H), 3.5–3.9(2H, m, C3-H and C5-H), 3.67(3H, s), 4.09(1H, d, J 8 Hz, C2α-H), 5.13(2H, s), 5.69(1H, dt, J 15, 1 Hz), 6.78(1H, dt, J 15, 6 Hz), and 7.30(5H, s). (Found: C; 62.1; H, 6.5; N, 3.4%; M+ 403.1453. $C_{21}H_{25}NO_5S$ requires C, 62.5: H, 6.2; N, 3.5%; M+, 403.1453)

EXAMPLE 68

Phthalidyl 3-ethylthio-6-(3-methoxycarbonylprop-2-en-1-yl)-7-oxo-1-azabicyclo[3.2.0]heptane-2α-carboxylate

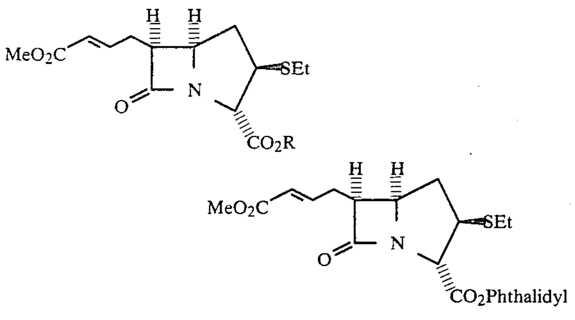

(97)

(25) R = p-bromophenacyl
(131) R = Na

The C2α, C3β-ester (25) (0.20 g) in dimethylformamide (2 ml, anhydrous) was treated with sodium thiophenoxide (0.055 g) as described above (Example 64). After 6 h. the C2α, C3β-sodium salt (131) was precipitated with ether in the usual way, and washed with a further portion of cold ether. The purified salt was redissolved in dimethylformamide (2 ml) and treated with bromophthalide (0.084 g) at room temperature in an atmosphere of argon overnight. The solution was diluted with ethyl acetate (50 ml), washed with saturated aqueous sodium chloride solution (3×15 ml) and dried ($Na_2SO_4$). Recovery gave an oil which was chromatographed on Kieselgel (5×2 cm) [elution with ethyl acetate-light petroleum (3:7)]. Fractions 23–31 afforded an oil which, on trituration with diethyl ether, followed by rapid removal of the solvent in vacuo gave a mixture of phthalide epimers of the C2α, C3β-isomer (97) of the title compound as a foam, which crystallised on standing at 0° overnight. The material (0.126 g) (72% overall from p-bromophenacyl ester) had m.p. 48°–50°. (Found: C, 59.1: H, 5.2; N, 3.1; S, 7.2. $C_{22}H_{23}NO_7S$ requires C, 59.3; H, 5.2; N, 3.1; S, 7.2%; $\nu_{max}$ ($CHCl_3$) 1790, 1770, 1750sh, 1720, 1660 $cm^{-1}$; δ ($CDCl_3$) 1.14(t, J7 Hz, minor epimer) and 1.25(t, j 7 Hz, major epimer) (together, 3H), 2.0–2.25(2H, m, C4-$H_2$), 2.3–2.8(4H, m), 3.46(1H, m, W½ 20 Hz, C3α-H), 3.70(3H, s), 4.19(1H, m, W½ 14 Hz, C5α-H), 4.73(d, J 7.5 Hz) and 4.75(d, J 7.5 Hz) (together 1H, C2β-H), 5.85 (1H, dd, J 16, 1 Hz), 6.89(1H, dt, J 16, 6 Hz), 7.47(1H, s), 7.70br, (3H, s), 7.92(1H, m); $\nu_{max}$ (EtOH) 282 nm (ε 2,240), 2.74 (2500), 228sh (17,700).

Careful crystallisation of the material ($CHCl_3$/EtOAC/$Et_2O$) deposited rosettes of one phthalide epimer m.p. 140°–142°.

EXAMPLE 69

Phthalidyl 3-ethylthio-6-(3-methoxycarbonylprop-2-en-1-yl)-7-oxo-1-azabicyclo[3.2.0]heptane-2β-carboxylate

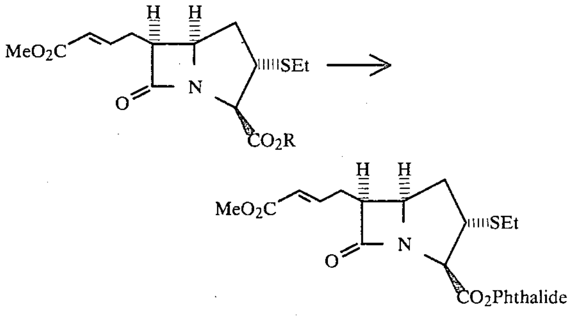

(135)

(27) R = p-bromophenacyl
(132) R = Na

The C2β, C3α-ester (27) (0.2 g) in dimethylformamide was treated with sodium thiophenoxide (0.055 g) (3h). Purification of the sodium salt (132) was followed by treatment with bromophthalide (0.1 g) in dimethylformamide as in example 68. Recovery and chromatography gave phthalide epimers of the C2β, C3α-isomer (135) (0.092 g); $\nu_{max}$ ($CDCl_3$) 1785, 1770, 1740sh, 1720, 1660 $cm^{-1}$; δ ($CDCl_3$) 1.24 (3H, t J 7 Hz), 1.8–2.7(6H, m), 3.3(1H, m, W½ 10 Hz, C6α-H), 3.67(3H, s), 3.8(1H, m, W½ 10 Hz, C5α-H), 4.08(d, J 5 Hz), and 4.17(d, J 5Hz), (together 1H, C2α-H), 5.69(dt, J15, 1 Hz) and 5.78(dt, J 15, 1 Hz) (together 1H), 6.90 (1H, m, W½ 20 Hz), 7.43(s) and 7.46(s) (together, 1H), 7.5–7.9 (4H, m).

EXAMPLE 70 p-Bromophenacyl 3-t-butylthio-6-(3-methoxycarboxylprop-2-en-1-yl)-7-oxo-1-azabicyclo[3.2.0]heptane-2-carboxylate

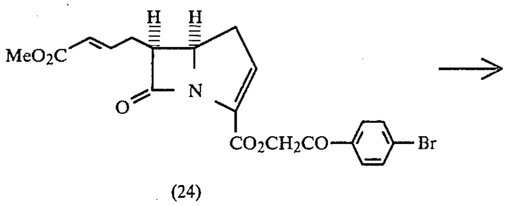

(24)

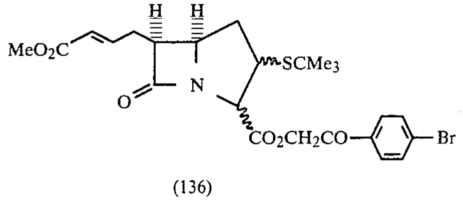

(136)

-continued

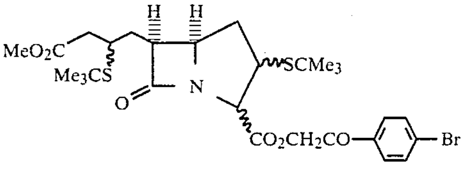

(137)

A solution of lithium t-butyl thiolate was prepared as follows: To a solution of t-butyl thiol (0.30 g; 375 ml) in tetrahydrofuran (3 ml) was added n-butyl lithium (0.94 ml of a 2.4 M solution in hexane) at −70° in an atmosphere of argon. The solution was stirred for 5 min. and allowed to warm to 0°. To the p-bromophenacyl ester (24) (0.050 g) in dimethylformamide (0.5 ml) was added one equivalent of the lithium t-butyl thiolate solution (130 μl) at −65° in an atmosphere of argon. After 10 minutes none of the p-bromophenacyl ester (24) remained [t.l.c. analysis; development with ethyl acetate-light petroleum (7:3)]. Recovery of the product in ethyl acetate indicated that a mixture of isomeric thiol-adducts (136) had been formed; $\nu_{max}$ ($CHCl_3$) 1760, 1740, 1725sh, 1690, 1660 and 1590 $cm^{-1}$. (no Δ-2 double bond present at $\nu_{max}$ 1610 $cm^{-1}$). Treatment of the product (136) with a second equivalent amount of lithium t-butyl thiolate reagent at −20° for 15 min. effected thiol addition across the acrylate double bond of the C6-side chain. The reaction was quenched with saturated aqueous ammonium chloride solution, and the mixture extracted with ethyl acetate. Recover, and chromatography of the products [elution with ethyl acetate-light petroleum (7:13)] gave an isomeric mixture of bisthioether adducts (137) (0.048 g) $\nu_{max}$($CHCl_3$) 1760, 1740 st, 1685, 1590 $cm^{-1}$; δ($CDCl_3$) 1.32 (18H, s), 2.6–3.5 (10H, m), 3.71 (3H, s), 5.37 (2H, s), 7.45 and 7.83 (4H, AA'BB', J 9 Hz).

EXAMPLE 71

Benzyl 6-benzyl-3-ethylthio-7-oxo-1-azabicyclo[3.2.0]heptane-2-carboxylate

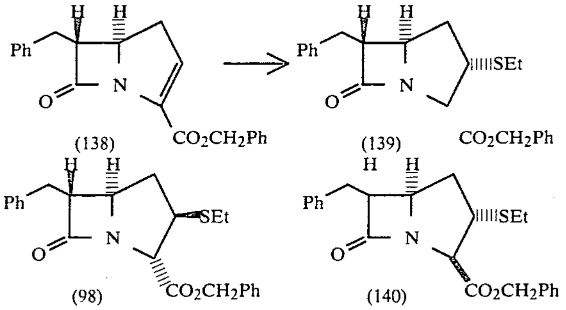

(138) (139) (98) (140)

Benzyl 6-benzyl-7-oxo-1-azabicyclo[3.2.0]hept-2-ene-2-carboxylate (138) (0.420 g) was dissolved in dry dimethylformamide (5 ml) and treated with ethanethiol (0.12 ml) and potassium carbonate (0.087 g). It was stirred at ambient temperature for 1 hour and the solvent was then distilled off under high vacuum. The residue was partitioned between ethyl acetate and brine, and the ethyl acetate solution was dried over sodium sulphate and concentrated. The residue was carefully chromatographed on a column of silica gel 60 (<230 mesh) eluting with ethyl acetate/60°–80° petroleum ether 3:7 to give three diastereoisomers of benzyl 6-benzyl-3-ethylthio-7-oxo-1-azabicyclo[3.2.0]heptane-2-carboxylate as gums. The first compound in increasing order of polarity was the 2α, 3α-isomer (139) (0.054 g); $\nu_{max}$ ($CHCl_3$) 2950, 1765 and 1745 sh; τ($CDCl_3$) 2.6–2.9 (10H, m, phenyls), 4.86 (2H, s, $OCH_2$), 5.59 (1H, d J 5 Hz, C2-H), 6.1–6.5 (2H, m, C3-Hand C5-H), 6.6–7.2 (3H, m, C6-H), 7.50 (2H, q J 7 Hz, $SCH_2$), 7.55 (1H, dt J 14 and 7 Hz, C4-H), 8.41 (1H, dt J 14 and 7 Hz, C4-H) and 8.84 (3H, t J 7 Hz, $CH_3$); (M+ at m/e 395.1554. $C_{23}H_{25}NO_3S$ requires 395.1553). Next was the 2α, 3β-isomer (98) (0.260 g); $\nu_{max}$($CHCl_3$) 2960, 1765 and 1750 sh $cm^{-1}$; τ($CDCl_3$) 2.6–2.9 (10H, m, phenyls), 4.87 (2H, s, $OCH_2$), 5.26 (1H, d, J 7 Hz, C2-H), 6.10 (1H, td, J $5\frac{1}{2}$ & $2\frac{1}{2}$ Hz, C5-H), 6.52 (1H, td J9 and 7 Hz, C3-H), 6.7–7.2 (3H, m, C6-H, C8-$H_2$), 7.47 (2H, q, J7 Hz, $SCH_2$), 7.89 (2H, dd J9 and $5\frac{1}{2}$ Hz, C4-$H_2$) and 8.85 (3H, t J7 Hz, $CH_3$); (M+ at m/e 395.1553. $C_{23}H_{25}NO_3S$ requires 395.1553). Lastly was obtained the 2β, 3α-isomer (140) (0.112 g); $\nu_{max}$($CHCl_3$) 2960, 1770 and 1745 $cm^{-1}$; τ($CDCl_3$) 2.6–2.9 (10H, m, phenyls), 4.82 (2H, s, $OCH_2$), 5.94 (1H, d J8 Hz, C2-H), 6.2–7.2 (5H, m, C3-H, C5-H, C6-H and C8-$H_2$), 7.51 (2H, d J7 Hz, $SCH_2$), 7.83 (1H, dt J12 and 6 Hz, C4-H), 8.10 (1H, td J12 and 9 Hz, C4-H) and 8.86 (3H, t J7 Hz, $CH_3$); ($M^{30}$ at m/e 394/1560. $C_{23}H_{25}NO_3S$ requires 395.1553).

EXAMPLE 72

Benzyl trans-6-(1-hydroxyethyl)-7-oxo-3-phenylthio-1-azabicyclo[3.2.0]heptane-2-carboxylate

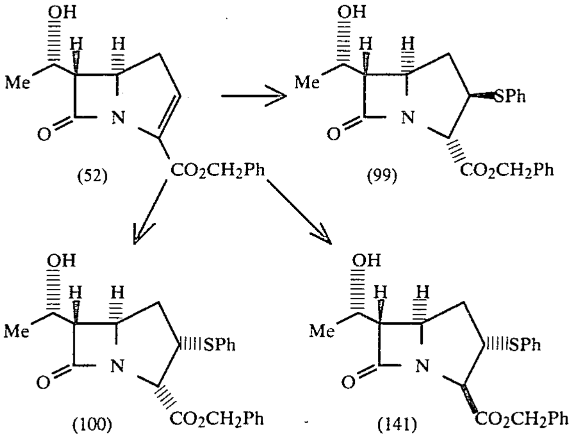

(52) (99) (100) (141)

A solution of benzyl trans-6-(1-hydroxyethyl)-7-oxo-1-azabicyclo[3.2.0]hept-2-ene-3-carboxylate (52) (0.300 g) in dry dimethylformamide (3 ml) was treated with thiophenol (0.12 ml) and finely ground potassium carbonate (0.072 g). It was stirred at room temperature for 1 hour and the solvent was then stripped off under high vacuum. The residue was dissolved in a mixture of ethyl acetate and brine, and the organic phase was separated, dried over sodium sulphate and concentrated. This was chromatographed on silica gel 60 (<230 mesh) eluting with ethyl acetate/60°–80° petroleum ether 1:1 grading to 7:3, to give two main fractions containing isomers of benzyl trans-6-(1-hydroxyethyl)-7-oxo-3-phenylthio-1-azabicyclo[3.2.0]heptane-2-carboxylate. The less polar fraction was a mixture (0.204 g) of the 2α, 3β isomer (99) and the 2α, 3α-isomer (100) in a 2:1 ratio; $\nu_{max}$($CHCl_3$) 3470, 3000, 1760, 1740 and 1585 $cm^{-1}$; τ($CDCl_3$) 2.5–2.9 (10H, m, phenyls), 4.85 ($1\frac{1}{3}$H, s, 3β- isomer, benzyl $CH_2$), 4.94 ($\frac{2}{3}$H, s, 3α-isomer, benzyl $CH_2$), 5.24 ($\frac{2}{3}$H, d J7 Hz, 3β-isomer, C2-H), 5.57 ($\frac{1}{3}$H, d J4 Hz, 3α-isomer, C2-H), 5.7–6.3 (3H, m, C3-H, C5-H and C8-H), 6.79 ($\frac{1}{3}$H, dd J6 and $2\frac{1}{2}$ Hz, 3α-isomer, C6-H), 6.98 ($\frac{2}{3}$H, dd J6 and 3 Hz, 3β-isomer, C6-H), 7.4–8.3 (3H, m, C4-$H_2$ and OH) and 8.72 (3H, d J7 Hz, $CH_3$); ($M^+$ at m/e 397.1364. $C_{22}H_{23}NO_4S$ requires 397.1346). The more polar fraction was crystallized from ethyl acetate/60°–80° petroleum ether to give the 2β, 3α-isomer (141) (0.055 g); m.p. 111°–112°; $\nu_{max}$($CHCl_3$) 3480, 2980, 1765, 1740 and 1585 $cm^{-1}$; τ($CDCl_3$) 2.6–2.9 (10H, m, phenyls), 4.80 (2H, s, benzyl $CH_2$), 5.82 (1H, d J7 Hz, C2-H), 5.8–6.2 (2H, m, C3-H and C8-H), 6.34 (1H, ddd, J10, 5 and $2\frac{1}{2}$ Hz, C5-H), 6.84 (1H, dd J$4\frac{1}{2}$ and $2\frac{1}{2}$ Hz, C6-H), 7.62 (1H, dt J12 and 5 Hz, C4-H), 7.86 (1H, s, OH), 7.93 (1H, td J12 and 10 Hz, C4-H) and 8.70 (3H, d J6 Hz, $CH_3$); (Found: C, 66.4; H, 6.1; N, 3.4%. $C_{22}H_{23}NO_4S$ requires C, 66.5; H, 5.8 and N, 3.5%.

EXAMPLE 73

Benzyl 3-ethylthio-trans-6-(2-hydroxy-2-propyl)-7-oxo-1-azabicyclo[3.2.0]heptane-2-carboxylate

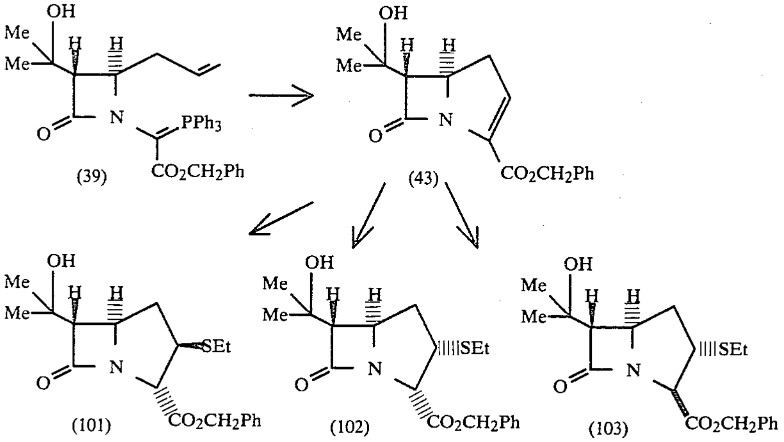

(39) (43) (101) (102) (103)

A solution of 4-allyl-1-(1-benzyloxycarbonyl-1-triphenylphosphoranylidenemethyl)-trans-3-(2-hydroxy-2-propyl)azetidin-2-one (39) (0.800 g) in ethylacetate (50 ml) was treated with trifluoroacetic acid (3 ml) and then cooled to −78°. Ozone was passed through the solution until it just became blue and excess ozone was then blown off in a stream of argon. An ethyl acetate solution of triphenylphosphine (0.363 g) was added and after 30 mins the reaction flask was transferred to an ice bath. The solution was vigorously stirred and neutralized by addition of saturated aqueus sodium bicarbonate (90 ml). After 30 mins the organic phase was separated washed with brine and dried over sodium sulphate. It was then concentrated under reduced pressure to give a crude preparation of the bicyclic compound (43). This was dissolved in dry dimethylformamide (6 ml) and the stirred solution treated with ethanethiol (0.15 ml) and powdered potassium carbonate (0.096 g). After a period of 1 hour the solvent was stripped off under vacuum at room temperature and the residue partitioned between ethyl acetate and brine. The ethyl acetate solution was separated and dried over sodium sulphate and then concentrated. It was chromatographed on a column of silica gel 60 (<230 mesh) eluting with ethyl acetate/60°–80° petroleum ether 1:1 to give three isomers of benzyl 3-ethylthio-trans-6-(2-hydroxy-2-propyl)-7-oxo-1-azabicyclo[3.2.0]heptane-2-carboxylate. The 2α, 3β-isomer (101) and 2α, 3α-isomer (102) were obtained as a 3:1 mixture (0.171 g); $\nu_{max}$($CHCl_3$) 3450, 2970 and 1755 $cm^{-1}$; τ($CDCl_3$) for (101) 2.69 (5H, s, phenyl), 4.88 (2H, s, benzyl $CH_2$), 5.28 (1H, d J7 Hz, C2-H), 5.97 (1H, td J5 and $2\frac{1}{2}$ Hz, C5-H), 6.53 (1H, td J9 and 7 Hz, C3-H), 7.03 (1H, d J$2\frac{1}{2}$ Hz, C6-H), 7.46 (2H, q J7 Hz, $SCH_2$), 7.82 (2H, dd J9 and 5 Hz, C4-$H_2$), 7.99 (1H, br s, OH), 8.66 (3H, s, $CH_3$), 8.71 (3H, s, $CH_3$) and 8.84 (3H, t J7 Hz, $CH_3$ or SEt); τ($CDCl_3$) for (102) 5.60 (d J4 Hz, C2-H) and 6.91 (d, J2 Hz, C6-H). The 2β, 3α-isomer (103) was obtained as a crystalline solid (0.087 g); m.p. 89°–91° (EtOAc/60°–80° petrol); $\nu_{max}$($CHCl_3$) 3480, 2970, 1765 and 1740 $cm^{-1}$; τ($CDCl_3$) 2.71 (5H, s, phenyl), 4.85 (2H, s, benzyl $CH_2$), 5.91 (1H, d J$7\frac{1}{2}$ Hz, C2-H), 6.2–6.5 (2H, m, C3-H and C5-H), 6.95 (1H, d J2 Hz, C6-H), 7.48 (2H, q J7 Hz, $SCH_2$), 7.75 (1H, dt J12 and 6 Hz, C4-H), 7.99 (1H, br s, OH), 8.08 (1H, td J12 and 10 Hz, C4-H), 8.65 and 8.73 (6H, 2s, $C(CH_3)_2$) and 8.85 (3H, t J7 Hz, $CH_3$ of SEt); (Found: C, 63.1; H, 7.0; N, 3.8%. $C_{19}H_{25}NO_4S$ requires C, 62.8; H, 6.9 and N, 3.8%).

EXAMPLE 74

Benzyl 3-ethylthio-cis-6-(2-hydroxy-2-propyl)-7-oxo-1-azabicyclo[3.2.0]heptane-2-carboxylate

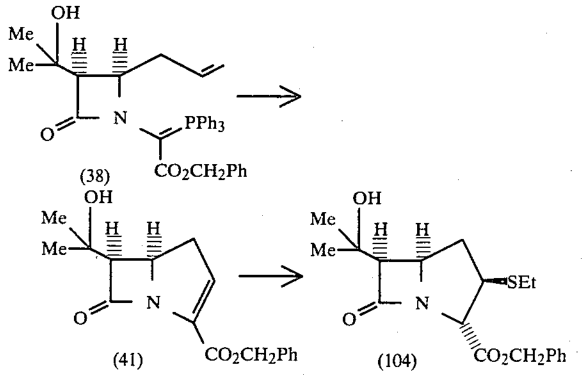

(38) (41) (104)

A solution of 4-allyl-1-(1-benzyloxycarbonyl-1-triphenylphosphoranylidenemethyl)-cis-3-(2-hydroxy-2-propyl)azetidine-2-one (38) (0.512 g) in ethyl acetate (40 ml) was treated with trifluoroacetic acid (2 ml) and then cooled to −78°. Ozone was passed through this solution until a permanent blue colour was just formed and the excess ozone was then removed by bubbling argon through the solution. The ozonide was reduced by addition of an ethyl acetate solution of triphenylphosphine (0.233 g). The reaction vessel was transferred to an ice bath after 30 mins and saturated aqueous sodium bicarbonate (60 ml) added with vigorous stirring. The ethyl acetate solution was separated after 30 mins and then dried over sodium sulphate. The solution was allowed to stand at room temperature for 24 hours to allow cyclization to the bicyclic compound (41) to go to completion. The solvent was removed and the residue taken up in dry dimethylformamide (5 ml). This solution was stirred at room temperature and treated with ethanethiol (0.1 ml) and powdered potassium carbonate (0.061 g). After 1 hour the solvent was distilled off under high vacuum and the residue partitioned between ethyl acetate and brine. The ethyl acetate phase was separated, dried over sodium sulphate and then concentrated. The residue was chromotagraphed on silica gel 60 (<230 mesh) eluting with ethyl acetate/60°-80° petroleum ether (3:7 to give benzyl 3-ethylthio-cis-6-(2-hydroxy-2-propyl)-7-oxo-1-azabicyclo[3.2.0]heptane-2-carboxylate (104) (0.089 g) as a gum; $\nu_{max}(CHCl_3)$ 3600, 2980 and 1755 $cm^{-1}$; $\tau(CDCl_3)$ 2.72 (5H, s, phenyl), 4,89 (2H, s, benzyl $CH_2$), 5.31 (1H, d J7½ Hz, C2-H), 5.88 (1H, ddd J9, 6 and 3 Hz, C5-H), 6.36 (1H, dt J10 and 7½ Hz, C3-H), 6.65 (1H, d J6 Hz, C6-H), 7.05 (1H, ddd J13, 7½ and 3 Hz, C4-H), 7.48 (2H, q J7 Hz, $SCH_2$), 8.04 (1H, ddd J13, 10 and 9 Hz, C4-H), 8.29 (1H, s, OH), 8.56 (3H, s, $CH_3$) and 8.74 (3H, s, $CH_3$) and 8.87 (3H, t J7 Hz, $CH_3$ of SEt); $M^+$ at m/e 363.1518. $C_{19}H_{25}NO_4S$ requires 363.1504).

β-Lactamase inhibition results

Method was automated hydroxyamine assay except for compounds marked + which were tested using the automated chromagenic substrate assay.

Results are presented as concentration of compounds in μg/ml for 50% inhibition of enzyme, except a percentage indicates amount of inhibition at maximum concentration of 20 μg/ml (50 μg/ml for asterisked figures).

| Comp. No. | *Ent. Cloacae* P99 | *Ps aerug* A | *P. Mirab* C889 | *Kleb aerog* E70 | *E. Coli* JT4 | *Staph aureus* Russel |
|---|---|---|---|---|---|---|
| 55 | NA | NA | 4 | | 28% | 3.7 |
| 57+ | 19%* | 47%* | 3.5 | 17% | 9 | 12.5 |
| 63 | 16% | NA | 3.3 | | 29% | 16.5 |
| 65+ | 47%* | | | NA | 0.35 | 35%* |
| 67+ | 50 | | | NA | 0.78 | 30%* |
| 68 | 25% | NA | 0.6 | | 8.0 | 2.0 |
| 69 | 23% | 44% | 2.4 | | 12.2 | 0.22 |
| 71 | | NA | 2.0 | | 8.5 | 10.0 |
| 73 | 31% | NA | 1.2 | | NA | 0.055 |
| 78 | 8.8 | 38% | 40% | | 16% | 7.6 |
| 80+ | 21.3 | | | 24 | 8.5 | 11.5 |
| 82+ | 19 | | | 2 | 13 | 20%* |
| 84 | 3.9 | 12.1 | NA | | 16% | NA |
| 86 | 2.5 | | NA | | NA | NA |
| 88 | 8.2 | 23% | 13% | | 8 | 19% |

Antibacterial activity in vivo

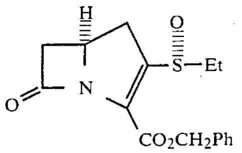

(55)

Experimental model: Mouse intraperitoneal infection
Micro-organism: *Escherichia coli* 8 suspended in 3% AL1 mucin plus 1% carboxymethylcellulose
Dosing route: Subcutaneous
Dosing schedule: 1, 1.5, 2, 2.5 hours after infection

| Expt No | CD50 Value mg/kg (total dose) Compound 55 |
|---|---|
| R21 | 5.2 |
| R23 | 8.8 |

Maximum total dose was 100 mg/kg and this time was tolerated by the mice.

I claim:

1. A compound of the formula:

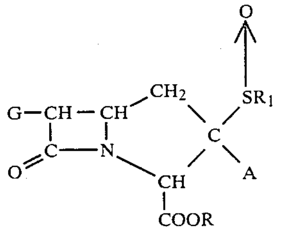

wherein

A is chloro, bromo or iodo;

$R_1$ is alkyl of 1 to 6 carbon atoms, unsubstituted or substituted with hydroxy, amino, alkanoylamido of 1 to 6 carbon atoms, benzyloxycarbonylamido or p-nitrobenzyloxycarbonylamido; phenyl; or phenyl substituted by one or more members selected from the group consisting of halo, alkyl of 1 to 6 carbon atoms, alkoxy of 1 to 6 carbon atoms, amino, alkanoylamido of 1 to 6 carbon atoms, benzyloxycarbonylamido or p-nitrobenzyloxycarbonylamido;

R is alkyl of 1 to 6 carbon atoms, benzyl, p-nitrobenzyl, p-methoxybenzyl, phenacyl, p-bromophenacyl, 2,2,2-trichloroethyl, phthalidyl, phthalimidomethyl, α-ethoxycarbonyloxyethyl or alkanoyloxymethyl of 1 to 6 carbon atoms, and G is hydrogen, alkyl or alkenyl, said alkyl and alkenyl being unsubstituted or substituted with hydroxy, oxy, methoxycarbonyl, phenyl or phenyl substituted with alkyl of 1 to 6 carbon atoms, alkoxy of 1 to 6 carbon atoms, nitro or halo.

2. A compound according to claim 1 wherein G is prop-2-en-1yl, 3-methylbut-2-en-1-yl or pent-2-en-1-yl.

3. A compound according to claim 1 wherein G is 4-oxopent-2-en-1-yl or 3-methoxy-carbonylprop-2-enyl.

4. A compound according to claim 1 wherein $R_1$ is alkanoylamido of 1 to 6 carbon atoms, benzyloxycarbonylamido or p-nitrobenzyloxycarbonylamido.

5. A compound according to claim 1 wherein $R_1$ is 2-acetylamidoethyl, phenyl, p-acetamidophenyl, ethyl, propyl, butyl or tertiary alkyl.

6. A compound according to claim 1 wherein G is hydrogen.

7. A compound according to claim 1 wherein R is alkyl of 1 to 6 carbon atoms, benzyl, p-nitrobenzyl, p-methoxybenzyl, phenacyl, p-bromophenacyl, 2,2,2-trichloroethyl, pthalidyl, pthalimidomethyl, α-ethoxycarbonyloxyethyl, pivaloyloxymethyl or acetoxymethyl.

8. A compound according to claim 1 wherein A is chloro.

9. The compound according to claim 1 which is benzyl 3-chloro-7-oxo-3-phenylsulphinyl-1-azabicyclo[3.2.0]heptane-2-carboxylate.

10. The compound according to claim 1 which is benzyl 3-chloro-3-ethylsulphinyl-7-oxo-1-azabicyclo[3.2.0]heptane-2-carboxylate.

11. The compound according to claim 1 which is p-nitrobenzyl 3-chloro-3-ethylsulphinyl-7-oxo-1-azabicyclo[3.2.0]heptane-2-carboxylate.

12. The compound according to claim 1 which is benzyl 3-(2-acetamidoethylsulphinyl)-3-chloro-7-oxo-1-azabicyclo[3.2.0]heptane-2-carboxylate.

13. The compound according to claim 1 which is benzyl 3-p-acetamidophenylsulphinyl-3-chloro-7-oxo-1-azabicyclo[3.2.0]heptane-2-carboxylate.

14. The compound according to claim 1 which is benzyl 3-chloro-6-(3-methoxycarbonylprop-2-ene-1-yl)-7-oxo-3-phenylsulphinyl-1-azabicyclo[3.2.0]heptane-2-carboxylate.

15. The compound according to claim 1 which is p-bromophenacyl 3-chloro-3-ethylsulphinyl-6-(3-methoxycarbonylprop-2-en-1-yl)-7-oxo-1-azabicyclo[3.2.0]heptane-2-carboxylate.

16. The compound according to claim 1 which is phthalidyl 3-chloro-3-ethylsulphinyl-6-(3-methoxycarbonylprop-2-en-1-yl)-7-oxo-1-azabicyclo[3.2.0]heptane-2-carboxylate.

17. The compound according to claim 1 which is benzyl 6-benzyl-3-chloro-3-ethylsulphinyl-7-oxo-1-azabicyclo[3.2.0]heptane-2-carboxylate.

18. The compound according to claim 1 which is benzyl 3-chloro-trans-6-(1-hydroxyethyl)-7-oxo-3-phenylsulphinyl-1-azabicyclo[3.2.0]heptane-2-carboxylate.

19. The compound according to claim 1 which is benzyl 3-chloro-3-ethylsulphinyl-6-(2-hydroxy-2-propyl)-7-oxo-1-azabicyclo[3.2.0]heptane-2-carboxylate.

* * * * *

UNITED STATES PATENT AND TRADEMARK OFFICE

CERTIFICATE OF CORRECTION

PATENT NO. : 4,289,696

DATED : September 15, 1981

INVENTOR(S) : TERENCE CHARLES SMALE

It is certified that error appears in the above-identified patent and that said Letters Patent are hereby corrected as shown below:

ON THE TITLE PAGE,

Change the foreign application priority data to show a priority date of November 12, 1977.

Signed and Sealed this

*Ninth* Day of *November 1982*

[SEAL]

*Attest:*

GERALD J. MOSSINGHOFF

*Attesting Officer* *Commissioner of Patents and Trademarks*